(12) United States Patent
Kim et al.

(10) Patent No.: US 8,921,412 B2
(45) Date of Patent: Dec. 30, 2014

(54) C-ARYL ANSA SGLT2 INHIBITORS

(75) Inventors: Min Ju Kim, Yongin-si (KR); Suk Ho Lee, Yongin-si (KR); Soongyu Choi, Yongin-si (KR)

(73) Assignee: Green Cross Corporation, Yongin-si (KR)

(*) Notice: Subject to any disclaimer, the term of this patent is extended or adjusted under 35 U.S.C. 154(b) by 0 days.

(21) Appl. No.: 14/123,793

(22) PCT Filed: Jun. 14, 2012

(86) PCT No.: PCT/KR2012/004703
§ 371 (c)(1),
(2), (4) Date: Feb. 28, 2014

(87) PCT Pub. No.: WO2012/173410
PCT Pub. Date: Dec. 20, 2012

(65) Prior Publication Data
US 2014/0213642 A1    Jul. 31, 2014

Related U.S. Application Data

(60) Provisional application No. 61/496,805, filed on Jun. 14, 2011.

(51) Int. Cl.
*A61K 31/335* (2006.01)
*C07D 491/056* (2006.01)
*C07D 493/08* (2006.01)

(52) U.S. Cl.
CPC .......... *C07D 491/056* (2013.01); *C07D 493/08* (2013.01)
USPC .......................... 514/450; 549/349; 549/348

(58) Field of Classification Search
USPC .................. 549/385, 349, 348; 514/455, 450
See application file for complete search history.

(56) References Cited

U.S. PATENT DOCUMENTS 5,589,473 A    12/1996  Geiwiz et al.
2008/0096923 A1    4/2008  Girach

OTHER PUBLICATIONS

International Searching Authority, International Search Report of PCT/KR2012/004703 dated Dec. 6, 2012.

*Primary Examiner* — Kristin Vajda
(74) *Attorney, Agent, or Firm* — Sughrue Mion, PLLC

(57) ABSTRACT

Disclosed is a novel C-aryl ansa compound having an inhibitory activity against sodium-dependent glucose cotransporter 2 (SGLT2) being present in the intestine and kidney, and a pharmaceutical composition comprising the same as an active ingredient, which is useful for preventing or treating metabolic disorders, particularly diabetes. Also provided are a method for preparing the compound, and a method for preventing or treating metabolic disorders, particularly diabetes, by using the compound.

11 Claims, 1 Drawing Sheet

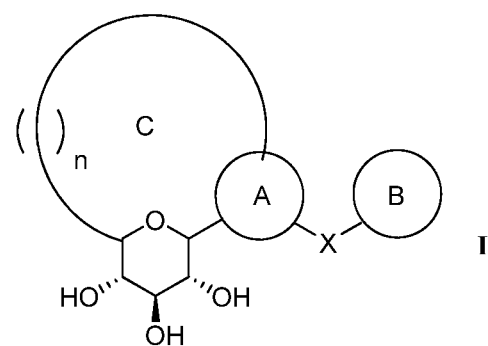

C-ARYL ANSA SGLT2 INHIBITORS

CROSS REFERENCE TO RELATED APPLICATIONS

This application is a National Stage of International Application No. PCT/KR2012/004703, filed on Jun. 14, 2012, the contents of all of which are incorporated herein by reference in their entirety.

FIELD OF THE INVENTION

The present invention relates to a novel C-aryl ansa compound having an inhibitory activity against sodium-dependent glucose cotransporter 2 (SGLT2) being present in the intestine and kidney, and a pharmaceutical composition comprising the same as an active ingredient, which is useful for preventing or treating diabetes.

BACKGROUND OF THE INVENTION

The prevalence of diabetes has become an increasing concern to the world's population. An estimated 285 million people, corresponding to 6.4% of the world's adult population, will live with diabetes in 2010. The number is expected to grow to 438 million by 2030, corresponding to 7.8% of the adult population. Diabetes is characterized by a chronic metabolic disorder that is caused by failure of the body to produce insulin and/or an inability of the body to respond adequately to circulating insulin. Secreted by the pancreas, insulin increases the ability of tissue to absorb blood glucose. Accordingly, disruption of insulin function results in the high level of blood glucose that is commonly associated with diabetic patients. There are two generally recognized form of diabetes: Type 1 diabetes, or insulin-dependent diabetes mellitus (IDDM), is characterized as an autoimmune disease involving pancreatic β-cells, while type 2 diabetes, or noninsulin-dependent diabetes mellitus (NIDDM), is characterized by β-cell dysfunction and insulin resistance. Type 2 diabetes is the most prevalent abnormality of glucose homeostasis, accounting for approximately 90-95% of all cases of diabetes. The diabetes has been widespread throughout the whole world due to ageing populations and rapid cultural changes such as increasing urbanization, dietary change, decreased physical activity and other unhealthy behavioral patterns.

The burden of diabetes is driven by vascular complications such as cardiovascular disease, stroke, nephropathy, retinopathy, renal failure, and lower limb infection and gangrene. Although these complications result from multiple metanolic disorders, hyperglycemia is considered as the main cause of both the vascular consequences of the disease and the progressive nature of diabetes itself. Most harmful of all is that high glucose levels aggravate insulin resistance, impair β-cell function and finally contribute to β-cell apoptosis. The loss of β-cell function exacerbates hyperglycemia, resulting in a vicious cycle that culminates in the object destruction of the β-cells. The United Kingdom Prevention of Diabetes Study (UKPDS) showed that incremental reductions in glycosylated hemoglobin (HbA1C) lowered the risk of diabetes-related events [Stratton, I. M. et al. *Br. Med. J.* 2000, 321, 405-412]. Thus, it is recommended that patients with type 2 diabetes should reduce HbA1C values to 7% and less.

The most important strategy for treatment of type 2 diabetes involves lifestyle interventions that promote body weight loss, leading to an improvement in glycemic control. In case lifestyle interventions are not enough for the management of diabetes, an extensive range of antidiabetic drugs might be considered for the treatment of the condition (monotherapies and combination therapies). These therapies target the liver to reduce glucose output, small intestine to decrease glucose absorption, adipose deposits or muscle to elevate glucose cellular uptake or to promote glucose metabolism, serum proteases to prolong incretin action, and the pancreas to enhance insulin release. Despite the wide range of antihyperglycemic agent, it is difficult for many patients to achieve HbA1C target level. In a study reviewing diabetic patients for control of vascular risk factors, only 37.0% of participants achieved the target goal of HbA1C level of less than 7.0% [Saydah, S. H. et al. *J. Am. Med. Assoc.* 2004, 291, 335-342]. In addition, current therapies have limited durability and/or are associated with significant side effects such as gastrointestinal intolerance, hypoglycemia, weight gain, lactic acidosis and edema. Thus, significant unmet medical needs still remain for the treatment of diabetes. In particular, safer, better tolerated medications which provide increased efficacy and long-term durability are desired.

The obvious need for new approaches to treat patients with uncontrolled type 2 diabetes has promoted continuous exploration of alternative targets in organs involved in maintenance of glucose homeostasis. In the context of type 2 diabetes, renal glucose reabsorption contributes to plasma glucose levels and the concomitant microvascular complications. Evaluation of molecular targets available in the kidney (a major unexploited contributor to glucose homeostasis) stimulated interest in the development of a new class of antihyperglycemic agents that promote urinary glucose excretion. Inhibitors of the SGLT2 prevent renal glucose reabsorption from the glomerular filtrate and provide an insulin-independent way of controlling hyperglycemia.

Sodium-dependent glucose cotransporters (SGLTs) couple the transport of glucose against a concentration gradient with the simultaneous transport of Na$^+$ down a concentration gradient. Two important SGLT isoforms have been cloned and identified as SGLT1 and SGLT2. SGLT1 is located in the gut, kidney, and heart where its expression regulates cardiac glucose transport. SGLT1 is a high-affinity, low-capacity transporter and therefore accounts for only a small fraction of renal glucose reabsorption. In contrast, SGLT2 is a low-affinity, high-capacity transporter located exclusively at the apical domain of the epithelial cells in the early proximal convoluted tubule. In healthy individuals, greater than 99% of the plasma glucose that filtered in the kidney glomerulus is reabsorbed, resulting in less than 1% of the total filtered glucose being excreted in urine. It is estimated that 90% of renal glucose reabsorption is facilitated by SGLT2; the remaining 10% is likely mediated by SGLT1 in the late proximal straight tubule. Genetic mutations in SGLT2 lead to increased renal glucose excretion of as much as 140 g/day depending on the mutation with no apparent adverse effects on carbohydrate metabolism. Since SGLT2 appears to be responsible for the majority of renal glucose reabsorption based on human mutation studies, it has become a target of therapeutic interest [Lee, J. et al. *Bioorg. Med. Chem.* 2010, 18, 2178-2194; van den Heuvel, L. P. et al. *Hum. Genet.* 2020, 111, 544-547].

Phlorizin was isolated from the root bark of the apple tree and evaluated as the first SGLT inhibitor. Despite antidiabetic potency of phlorizin, its metabolic instability due to β-glucosidase cleavage in the intestinal tract has prevented its development as a drug for the treatment of diabetes. Subsequently, T-1095, by Tanabe Seiyaku, was reported as the first orally absorbable SGLT2 inhibitor, overcoming the disadvantage of phlorizin. T-1095 was absorbed in the intestine and converted to an active form, T-1095A. Following the discovery of T-1095, O-aryl glucosides such as sergliflozin and remogliflozin advanced furthest in clinical trials. Again, concern regarding gut β-glucosidase-mediated degradation, resulted in developing sergliflozin A and remogliflozin A being administered as the ethyl carbonate prodrugs sergliflozin and remogliflozin, respectively. Subsequent endeavors to identify SGLT2 inhibitors suitable for oral administration without the need for a prodrug led to the discovery of C-aryl glucoside-derived SGLT2 inhibitors. C-aryl glucosides appear to have drug-like properties with enhanced chemical stability of the glucosidic bond. Extensive SAR studies by Bristol-Myers Squibb identified dapagliflozin, a potent, selective SGLT2 inhibitor for the treatment of type 2 diabetes. At present, dapagliflozin is the most advanced SGLT2 inhibitor in clinical trials and is believed to be the first SGLT2 inhibitor to go to market [Meng, W. et al. *J. Med. Chem.* 2008, 51, 1145-1149]. On the other hand, Mitsubishi Tanabe Pharma, in collaboration with Johnson & Johnson, is developing canagliflozin, another novel C-aryl glucoside-derived SGLT2 inhibitor [Tanabe Seiyaku, WO2008013321].

Considering the important impact of diabetes on public health and unmet medical needs of current therapy, it is no surprise that SGLT2 inhibitors are currently interesting topics of studies, which were published in the following review articles [Washburn, W. N. *Expert Opin. Ther. Patents,* 2009, 19, 1485-1499; Washburn, W. N. *J. Med. Chem.* 2009, 52, 1785-1794].

SUMMARY OF THE INVENTION

It is an object of the present invention to provide a novel C-aryl ansa compound of formula I, or a pharmaceutically acceptable salt thereof, or a prodrug thereof, which is effective as an SGLT2 inhibitor, and is useful for the prevention and/or treatment of metabolic disorders, particularly diabetes.

It is other object of the present invention to provide a method for preparing the inventive compound.

It is another object of the present invention to provide a pharmaceutical composition for preventing or treating metabolic disorders, particularly diabetes.

It is yet another object of the present invention to provide a method for preventing or treating a metabolic disorder, particularly diabetes, in a mammal.

It is still another object of the present invention to provide a method for inhibiting sodium-dependent glucose cotransporter 2 (SGLT2) in a mammal.

It is a further object of the present invention to provide a use of the inventive compound.

In accordance with one aspect of the present invention, there is provided a compound of formula I, or a pharmaceutically acceptable salt thereof, or a prodrug thereof, wherein formula I is as defined herein.

In accordance with other aspect of the present invention, there is provided a method for preparing the compound of formula I, especially a compound of formula II-3 or II-6.

In accordance with another aspect of the present invention, there is provided a pharmaceutical composition for preventing or treating a metabolic disorder, comprising as an active ingredient the compound of formula I, or a pharmaceutically acceptable salt or a prodrug thereof, and a pharmaceutically acceptable carrier.

In accordance with yet another aspect of the present invention, there is provided a method for preventing or treating a metabolic disorder in a mammal, which comprises administering the compound of formula I or a pharmaceutically acceptable salt or a prodrug thereof to the mammal.

In accordance with still another aspect of the present invention, there is provided a method for inhibiting sodium-dependent glucose cotransporter 2 (SGLT2) in a mammal, which comprises administering the compound of formula I or a pharmaceutically acceptable salt or a prodrug thereof to the mammal.

In accordance with a further aspect of the present invention, there is provided a use of the compound of formula I or a pharmaceutically acceptable salt or a prodrug thereof for the manufacture of a medicament for preventing or treating a metabolic disorder.

DETAILED DESCRIPTION OF THE INVENTION

As used herein, the term "alkyl" refers to a straight or branched chain saturated hydrocarbon radical. Examples of "alkyl" as used herein include, but are not limited to, methyl, ethyl, n-propyl, isopropyl, n-butyl, isobutyl, t-butyl, n-pentyl, isopentyl and hexyl.

As used herein, the term "substituted alkyl" refers to a straight or branched chain saturated hydrocarbon radical, which is optionally substituted by one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heteroaryloxy, heterocyclic, aminosulfonyl, sulfonylamino, carboxyamide, ureido, nitro, cyano and halogen.

As used herein, the term "alkenyl" refers to a straight or branched chain hydrocarbon radical having at least one carbon-carbon double bond. Examples of "alkenyl" as used herein include, but are not limited to, ethenyl and propenyl.

As used herein, the term "substituted alkenyl" refers to a straight or branched chain hydrocarbon radical having at least one carbon-carbon double bond, which has optional substituents selected from the group consisting of $C_{1-3}$ alkyl optionally having one to three fluorine substituents, amino, aryl, cyano and halogen.

As used herein, the term "alkynyl" refers to a straight or branched chain hydrocarbon radical having at least one carbon-carbon triple bond. Examples of "alkynyl" as used herein include, but are not limited to, acetylenyl and 1-propynyl.

As used herein, the term "substituted alkynyl" refers to a straight or branched chain hydrocarbon radical having at least one carbon-carbon triple bond, optionally having one or more substituents selected from the group consisting of $C_{1-3}$ alkyl optionally having one to three fluorine substituents, amino, aryl and halogen.

As used herein, the term "halogen" refers to fluorine (F), chlorine (Cl), bromine (Br), or iodine (I).

As used herein, the term "carbocycle" refers to a non-aromatic cyclic hydrocarbon radical composed of three to seven carbon atoms. Five- to seven-membered rings may contain a double bond in the ring structure. Exemplary "carbocycle" groups include, but are not limited to, cyclopropyl, cyclobutyl, cyclopentyl, cyclopentenyl, cyclohexyl and cycloheptyl.

As used herein, the term "substituted carbocycle" refers to a non-aromatic cyclic hydrocarbon radical composed by three to seven carbon atoms, which is optionally substituted with one or more substituents selected from the group consisting of $C_{1-3}$ alkyl optionally having one to three fluorine substituents, $C_{2-3}$ alkenyl, $C_{2-3}$ alkynyl, $C_{1-2}$ alkoxy optionally having one to three fluorine substituents, sulfanyl, sulfinyl, sulfonyl, oxo, hydroxy, mercapto, amino, guanidino, carboxy, aminocarbonyl, aryl, aryloxy, heteroaryl, heterocyclic, aminosulfonyl, sulfonylamino, carboxyamide, nitro, ureido, cyano and halogen.

As used herein, the term "aryl" refers to an optionally substituted benzene ring or refers to a ring system which may result by fusing one or more optional substituents. Exemplary optional substituents include substituted $C_{1-3}$ alkyl, substituted $C_{2-3}$ alkenyl, substituted $C_{2-3}$ alkynyl, heteroaryl, heterocyclic, aryl, alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen, or ureido. Such a ring or ring system may be optionally fused to aryl rings (including benzene rings) optionally having one or more substituents, carbocycle rings or heterocyclic rings. Examples of "aryl" groups include, but are not limited to, phenyl, naphthyl, tetrahydronaphthyl, biphenyl, indanyl, anthracyl or phenanthryl, as well as substituted derivatives thereof.

As used herein, the term "heteroaryl" refers to an optionally substituted monocyclic five to six-membered aromatic ring containing one or more heteroatomic substitutions selected from S, SO, $SO_2$, O, N, or N-oxide, or refers to such an aromatic ring fused to one or more rings such as heteroaryl rings, aryl rings, heterocyclic rings, or carbocycle rings (e.g., a bicyclic or tricyclic ring system), each having optional substituents.

Examples of optional substituents are selected from the group consisting of substituted $C_{1-3}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, aminosulfonyl, sulfonylamino, carboxyamide, aminocarbonyl, carboxy, oxo, hydroxy, mercapto, amino, nitro, cyano, halogen or ureido. Examples of "heteroaryl" groups used herein include, but are not limited to, benzoimidazolyl, benzothiazolyl, benzoisothiazolyl, benzothiophenyl, benzopyrazinyl, benzotriazolyl, benzo[1,4]dioxanyl, benzofuranyl, 9H-a-carbolinyl, cinnolinyl, furanyl, furo[2,3-b]pyridinyl, imidazolyl, imidazolidinyl, imidazopyridinyl, isoxazolyl, isothiazolyl, isoquinolinyl, indolyl, indazolyl, indolizinyl, naphthyridinyl, oxazolyl, oxothiadiazolyl, oxadiazolyl, phthalazinyl, pyridyl, pyrrolyl, purinyl, pteridinyl, phenazinyl, pyrazolyl, pyridyl, pyrazolopyrimidinyl, pyrrolizinyl, pyridazyl, pyrazinyl, pyrimidyl, 4-oxo-1,2-dihydro-4H-pyrrolo[3,2,1-ij]-quinolin-4-yl, quinoxalinyl, quinazolinyl, quinolinyl, quinolizinyl, thiophenyl, triazolyl, triazinyl, tetrazolopyrimidinyl, triazolopyrimidinyl, tetrazolyl, thiazolyl, thiazolidinyl, and substituted versions thereof.

As used herein, the term "heterocyclic" refers to a three to seven-membered ring containing one or more heteroatomic moieties selected from S, SO, $SO_2$, O, N, or N-oxide, optionally substituted with one or more substituents selected from the group which includes substituted $C_{1-3}$ alkyl, substituted $C_{2-3}$ alkenyl, substituted $C_{2-3}$ alkynyl, heteroaryl, heterocyclic, aryl, $C_{1-3}$ alkoxy optionally having one to three fluorine substituents, aryloxy, aralkoxy, acyl, aroyl, heteroaroyl, acyloxy, aroyloxy, heteroaroyloxy, sulfanyl, sulfinyl, sulfonyl, amino sulfonyl, sulfonylamino, carboxyamide, aminocarbonyl, carboxy, oxo, hydroxy, mercapto, amino, nitro, cyano, halogen, and ureido. Such a ring can be saturated or have one or more degrees of unsaturation. Such a ring may be optionally fused to one or more "heterocyclic" ring(s), aryl ring(s), heteroaryl ring(s) or carbocycle ring(s), each having optional substituents.

Examples of "heterocyclic" moieties include, but are not limited to, 1,4-dioxanyl, 1,3-dioxanyl, pyrrolidinyl, pyrrolidin-2-onyl, piperidinyl, imidazolidine-2,4-dionepiperidinyl, piperazinyl, piperazine-2,5-dionyl, morpholinyl, dihydropyranyl, dihydrocinnolinyl, 2,3-dihydrobenzo[1,4]dioxinyl, 3,4-dihydro-2H-benzo[b][1,4]-dioxepinyl, tetrahydropyranyl, 2,3-dihydrofuranyl, 2,3-dihydrobenzofuranyl, dihydroisoxazolyl, tetrahydrobenzodiazepinyl, tetrahydroquinolinyl, tetrahydrofuranyl, tetrahydronaphthyridinyl, tetrahydropurinyl, tetrahydrothiopyranyl, tetrahydrothiophenyl, tetrahydroquinoxalinyl, tetrahydropyridinyl, tetrahydrocarbolinyl, 4H-benzo[1,3]-dioxinyl, benzo[1,3]dioxonyl, 2,2-difluorobenzo-[1,3]-dioxonyl, 2,3-dihydro-phthalazine-1,4-dionyl, and isoindole-1,3-dionyl.

As used herein, the term "alkoxy" refers to the group —$OR_a$, where $R_a$ is alkyl as defined above. Exemplary alkoxy groups useful in the present invention include, but are not limited to, methoxy, difluoromethoxy, trifluoromethoxy, ethoxy, n-propoxy, isopropoxy, n-butoxy and t-butoxy.

As used herein the term "aralkoxy" refers to the group —$OR_aR_b$, wherein $R_a$ is alkyl and $R_b$ is aryl as defined above.

As used herein the term "aryloxy" refers to the group —$OR_b$, wherein $R_b$ is aryl as defined above.

As used herein, the term "mercapto" refers to the group —SH.

As used herein, the term "sulfanyl" refers to the group —$SR_c$, wherein $R_c$ is substituted alkyl, substituted carbocycle, aryl, heteroaryl or heterocyclic, as defined above.

As used herein, the term "sulfinyl" refers to the group —S—(O)$R_c$, wherein $R_c$ is substituted alkyl, substituted carbocycle, aryl, heteroaryl or heterocyclic, as defined above.

As used herein, the term "sulfonyl" refers to the group —$S(O)_2R_c$, wherein $R_c$ is substituted alkyl, substituted carbocycle, aryl, heteroaryl or heterocyclic, as defined above.

As used herein, the term "oxo" refers to the group =O.

As used herein, the term "hydroxy" refers to the group —OH.

As used herein, the term "amino" refers to the group —$NH_2$. The amino group is optionally substituted by substituted alkyl, substituted carbocycle, aryl, heteroaryl or heterocyclic, as defined above.

As used herein, the term "cyano" refers to the group —CN.

As used herein, the term "aminosulfonyl" refers to the group —$S(O)_2NH_2$. The aminosulfonyl group is optionally substituted by substituted alkyl, substituted carbocycle, aryl, heteroaryl or heterocyclic, as defined above.

As used herein, the term "sulfonylamino" refers to the group —$NHS(O)_2R_c$ wherein $R_c$ is substituted alkyl, substituted carbocycle, aryl, heteroaryl or heterocyclic, as defined above.

As used herein, the term "carboxyamide" refers to the group —$NHC(O)R_c$ wherein $R_c$ is substituted alkyl, substituted carbocycle, aryl, heteroaryl or heterocyclic, as defined above.

As used herein, the term "carboxy" refers to the group —C(O)OH. The carboxy group is optionally substituted by substituted alkyl, substituted carbocycle, aryl, heteroaryl or heterocyclic, as defined above.

As used herein, the term "aminocarbonyl" refers to the group —$C(O)NH_2$. The aminocarbonyl group is optionally substituted by substituted alkyl, substituted carbocycle, aryl, heteroaryl or heterocyclic, as defined above.

As used herein, the term "ureido" refers to the group —$NHC(O)NHR_d$ wherein $R_d$ is hydrogen, alkyl, carbocycle or aryl as defined above.

As used herein, the term "guanidino" refers to the group —NHC(=NH)$NH_2$.

As used herein, the term "acyl" refers to the group —C(O)R$_e$, wherein R$_e$ is alkyl, carbocycle, or heterocyclic as defined herein.

As used herein, the term "aroyl" refers to the group —C(O)R$_b$, wherein R$_b$ is aryl as defined herein.

As used herein, the term "heteroaroyl" refers to the group —C(O)R$_f$, wherein R$_f$ is heteroaryl as defined herein.

As used herein, the term "acyloxy" refers to the group —OC(O)R$_e$, wherein R$_e$ is alkyl, carbocycle, or heterocyclic as defined herein.

As used herein, the term "aroyloxy" refers to the group —OC(O)R$_b$, wherein R$_b$ is aryl as defined herein.

As used herein, the term "heteroaroyloxy" refers to the group —OC(O)R$_f$, wherein R$_f$ is heteroaryl as defined herein.

It is to be understood that the present invention also includes a pharmaceutically acceptable salt and an addition salt of the inventive compound, such as a hydrochloride, hydrobromide or trifluoroacetate addition salt and a sodium, potassium and magnesium salt.

Further, it should be construed that the present invention also includes prodrugs of the inventive compound. The term "prodrug" refers to a pharmacologically inactive compound that is converted to an active drug by a metabolic biotransformation. Examples of the prodrug include carrier-linked prodrugs (e.g., ester analogs), and bioprecursor prodrugs. Those skilled in the art can easily design and prepare suitable prodrugs based on the inventive compound.

The compounds of the present invention may contain one or more asymmetric carbon atoms and may exist in racemic and optically active forms. All of these compounds and diastereomers are incorporated within the scope of the present invention.

In one aspect of the present invention, the compound of the present invention has the following structure:

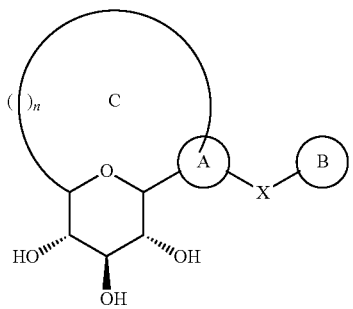

I wherein,

X is methylene or cyclopropane;

ring A is benzene, naphthalene, or indole;

ring B is

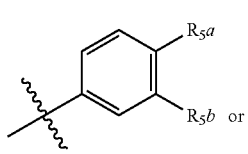

B-1

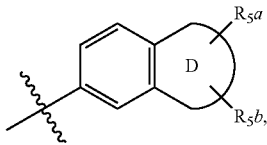

B-2 said ring D being C$_{3-10}$ cycloalkyl, C$_{5-10}$ cycloalkenyl, C$_{6-14}$ aryl, 5 to 13-membered heteroaryl, or 5 to 10-membered heterocycloalkyl;

ring C is a macrocycle formed by connecting ansa bridge between the tetrahydropyran ring and ring A; and n is an integer of 5 to 10, wherein, said ring A and ring B are each independently optionally substituted with at least one selected from the group consisting of hydrogen, halogen, hydroxy, mercapto, cyano, nitro, amino, carboxy, C$_{1-7}$ alkyl, C$_{2-7}$ alkenyl, C$_{2-7}$ alkynyl, hydroxy-C$_{1-7}$ alkyl, C$_{1-7}$ alkoxy, C$_{1-7}$ alkoxy-C$_{1-7}$ alkyl, C$_{2-7}$ alkenyl-C$_{1-7}$ alkyloxy, C$_{2-7}$ alkynyl-C$_{1-7}$ alkyloxy, C$_{3-10}$ cycloalkyl, C$_{5-10}$ cycloalkenyl, C$_{3-10}$ cycloalkyloxy, phenyl-C$_{1-7}$ alkoxy, mono- or di-C$_{1-7}$ alkylamino, C$_{1-7}$ alkanoyl, C$_{1-7}$ alkanoylamino, C$_{1-7}$ alkoxycarbonyl, carbamoyl, mono- or di-C$_{1-7}$ alkylcarbamoyl, C$_{1-7}$ alkylsulfonylamino, phenylsulfonylamino, C$_{1-7}$ alkylsulfanyl, C$_{1-7}$ alkylsulfinyl, C$_{1-7}$ alkylsulfonyl, C$_{6-14}$ arylsulfanyl, C$_{6-14}$ arylsulfonyl, C$_{6-14}$ aryl, 5 to 13-membered heteroaryl, and 5 to 10-membered heterocycloalkyl;

said R$_{5a}$, R$_{5b}$, R$_{6a}$, and R$_{6b}$ are each independently selected from the group consisting of hydrogen, halogen, hydroxy, mercapto, cyano, nitro, amino, carboxy, C$_{1-7}$ alkyl, C$_{2-7}$ alkenyl, C$_{2-7}$ alkynyl, hydroxy-C$_{1-7}$ alkyl, C$_{1-7}$ alkoxy, C$_{1-7}$ alkoxy-C$_{1-7}$ alkyl, C$_{2-7}$ alkenyl-C$_{1-7}$ alkyloxy, C$_{2-7}$ alkynyl-C$_{1-7}$ alkyloxy, C$_{3-10}$ cycloalkyl, C$_{5-10}$ cycloalkenyl, C$_{3-10}$ cycloalkyloxy, phenyl-C$_{1-7}$ alkoxy, mono- or di-C$_{1-7}$ alkylamino, C$_{1-7}$ alkanoyl, C$_{1-7}$ alkanoylamino, C$_{1-7}$ alkoxycarbonyl, carbamoyl, mono- or di-C$_{1-7}$ alkylcarbamoyl, C$_{1-7}$ alkylsulfonylamino, phenylsulfonylamino, C$_{1-7}$ alkylsulfanyl, C$_{1-7}$ alkylsulfinyl, C$_{1-7}$ alkylsulfonyl, C$_{6-14}$ arylsulfanyl, C$_{6-14}$ arylsulfonyl, C$_{6-14}$ aryl, 5 to 13-membered heteroaryl, and 5 to 10-membered heterocycloalkyl;

said alkyl, alkenyl, alkynyl, or alkoxy is optionally substituted with at least one selected from the group consisting of halogen, hydroxy, cyano, nitro, amino, mercapto, C$_{1-7}$ alkyl, and C$_{2-7}$ alkynyl; and said cycloalkyl, cycloalkenyl, aryl, heteroaryl, or heterocycloalkyl is optionally substituted with at least one selected from the group consisting of halogen, hydroxy, cyano, nitro, amino, mercapto, C$_{1-4}$ alkyl, and C$_{1-4}$ alkoxy.

In one embodiment of the present invention, ring A is selected from the group consisting of:

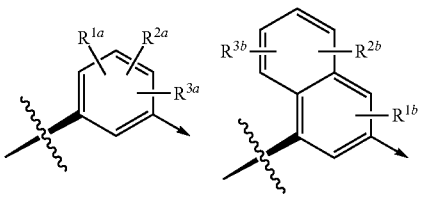

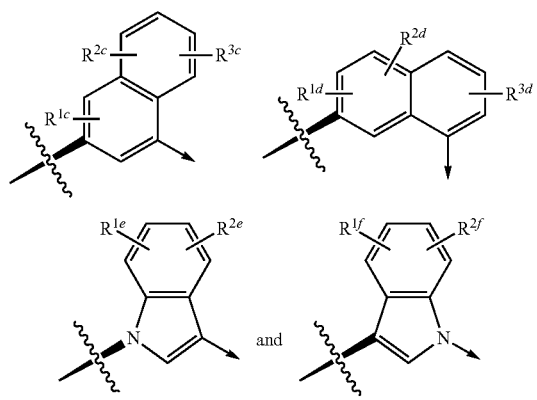

wherein, $R^{1a}$, $R^{2a}$, $R^{3a}$, $R^{1b}$, $R^{2b}$, $R^{3b}$, $R^{1c}$, $R^{2c}$, $R^{3c}$, $R^{1d}$, $R^{2d}$, $R^{3d}$, $R^{1e}$, $R^{2e}$, $R^{1f}$, and $R^{2f}$ are each independently selected from the group consisting of hydrogen, halogen, hydroxy, mercapto, cyano, nitro, amino, carboxy, $C_{1-7}$ alkyl, $C_{2-7}$ alkenyl, $C_{2-7}$ alkynyl, hydroxy-$C_{1-7}$ alkyl, $C_{1-7}$ alkoxy, $C_{1-7}$ alkoxy-$C_{1-7}$ alkyl, $C_{2-7}$ alkenyl-$C_{1-7}$ alkyloxy, $C_{2-7}$ alkynyl-$C_{1-7}$ alkyloxy, $C_{3-10}$ cycloalkyl, $C_{5-10}$ cycloalkenyl, $C_{3-10}$ cycloalkyloxy, phenyl-$C_{1-7}$ alkoxy, mono- or di-$C_{1-7}$ alkylamino, $C_{1-7}$ alkanoyl, $C_{1-7}$ alkanoylamino, $C_{1-7}$ alkoxycarbonyl, carbamoyl, mono- or di-$C_{1-7}$ alkylcarbamoyl, $C_{1-7}$ alkylsulfonylamino, phenylsulfonylamino, $C_{1-7}$ alkylsulfanyl, $C_{1-7}$ alkylsulfinyl, $C_{1-7}$ alkylsulfonyl, $C_{6-14}$ arylsulfanyl, $C_{6-14}$ arylsulfonyl, $C_{6-14}$ aryl, 5 to 13-membered heteroaryl, and 5 to 10-membered heterocycloalkyl.

In another embodiment of the present invention, ring B-1 is selected from the group consisting of:

In yet another embodiment of the present invention, ring B-2 is selected from the group consisting of:

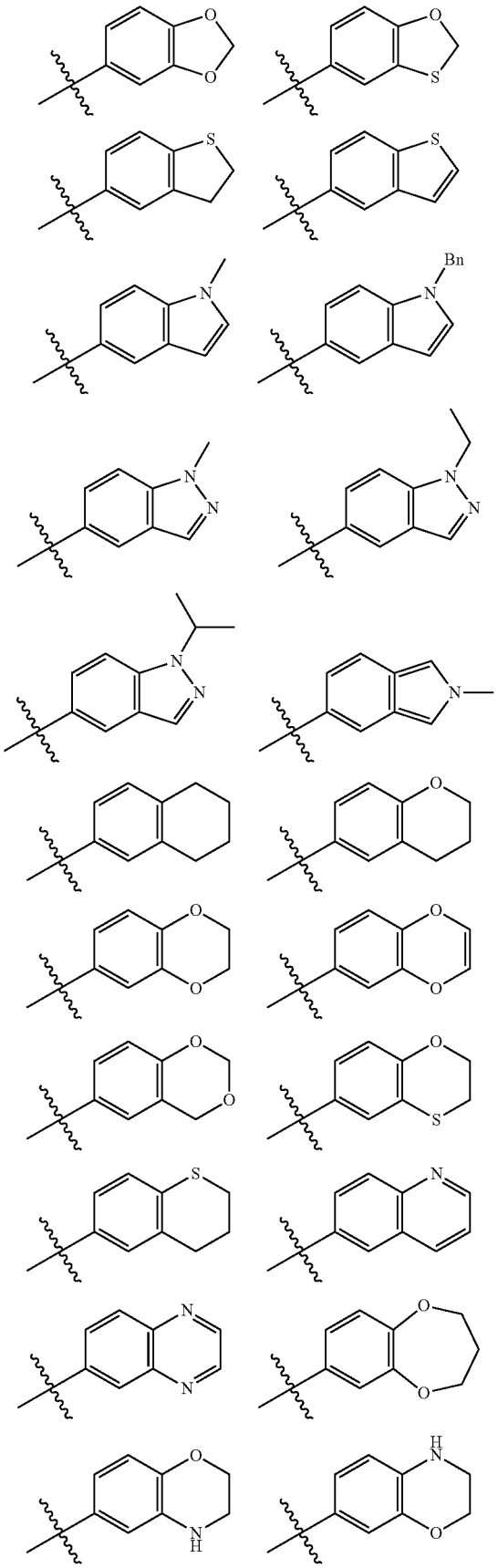

-continued

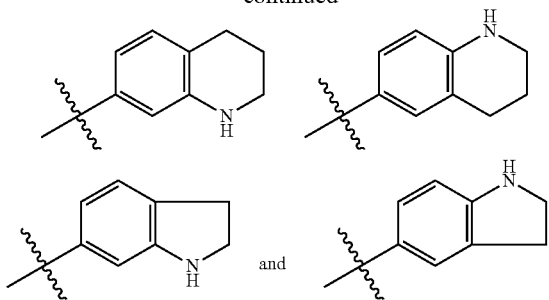

and

In a preferred embodiment of the present invention, the compound of the present invention has the following structure:

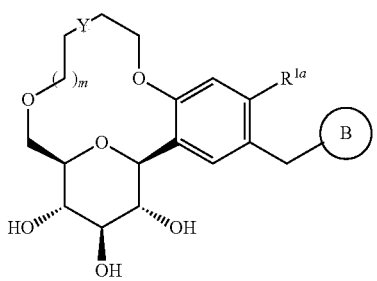

I-1 wherein,

Y is a single bond or double bond, or forms a cyclopropane ring together with the two adjacent carbon atoms;

m is an integer of 1 to 4;

$R^{1a}$ is halogen; and ring B is

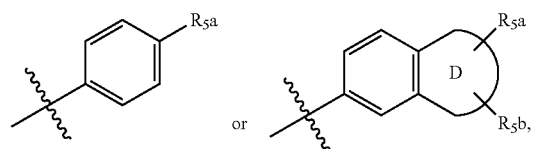

or said $R_{5a}$, $R_{6a}$, and $R_{6b}$ being each independently selected from the group consisting of hydrogen, halogen, hydroxy, mercapto, cyano, nitro, amino, carboxy, $C_{1-7}$ alkyl, $C_{2-7}$ alkenyl, $C_{2-7}$ alkynyl, hydroxy-$C_{1-7}$ alkyl, $C_{1-7}$ alkoxy, $C_{1-7}$ alkoxy-$C_{1-7}$ alkyl, $C_{2-7}$ alkenyl-$C_{1-7}$ alkyloxy, $C_{2-7}$ alkynyl-$C_{1-7}$ alkyloxy, $C_{3-10}$ cycloalkyl, $C_{5-10}$ cycloalkenyl, $C_{3-10}$ cycloalkyloxy, phenyl-$C_{1-7}$ alkoxy, mono- or di-$C_{1-7}$ alkylamino, $C_{1-7}$ alkanoyl, $C_{1-7}$ alkanoylamino, $C_{1-7}$ alkoxycarbonyl, carbamoyl, mono- or di-$C_{1-7}$ alkylcarbamoyl, $C_{1-7}$ alkylsulfonylamino, phenylsulfonylamino, $C_{1-7}$ alkylsulfanyl, $C_{1-7}$ alkylsulfinyl, $C_{1-7}$ alkylsulfonyl, $C_{6-14}$ arylsulfanyl, $C_{6-14}$ arylsulfonyl, $C_{6-14}$ aryl, 5 to 13-membered heteroaryl, or 5 to 10-membered heterocycloalkyl, and said ring D being dioxanyl.

Compounds especially useful in the present invention are selected from the group consisting of:

(1) (8R,9S,10R,11R,12S)-15-Chloro-14-(4-ethoxybenzyl)-2,5,7,8,9,10,11,12-octahydro-2H-8,12-epoxybenzo[g][1,6]dioxacyclotetradecine-9,10,11-triol;

(2) (8R,9S,10R,11R,12S)-15-Chloro-14-(4-ethoxybenzyl)-2,3,4,5,7,8,9,10,11,12-decahydro-2H-8,12-epoxybenzo[g][1,6]dioxacyclotetradecine-9,10,11-triol;

(3) (9R,10S,11R,12R,13S)-16-Chloro-15-(4-ethoxybenzyl)-3,4,5,6,8,9,10,11,12,13-decahydro-2H-9,13-epoxybenzo[h][1,7]dioxacyclopentadecine-10,11,12-triol;

(4) (6R,7S,8R,9R,10S)-13-Chloro-12-(4-ethoxybenzyl)-2,3,5,6,7,8,9,10-octahydro-6,10-epoxybenzo[e][1,4]dioxacyclododecine-7,8,9-triol;

(5) (7R,8S,9R,10R,11S)-14-Chloro-13-(4-ethoxybenzyl)-3,4,6,7,8,9,10,11-octahydro-2H-7,11-epoxybenzo[f][1,5]dioxacyclotridecine-8,9,10-triol;

(6) (10R,11S,12R,13R,14S)-17-Chloro-16-(4-ethoxybenzyl)-2,3,4,5,6,7,9,10,11,12,13,14-dodecahydro-10,14-epoxybenzo[i][1,8]dioxacyclohexadecine-11,12,13-triol;

(7) (7R,8S,9R,10R,11S)-14-Chloro-13-(4-ethylbenzyl)-3,4,6,7,8,9,10,11-octahydro-2H-7,11-epoxybenzo[f][1,5]dioxacyclotridecine-8,9,10-triol;

(8) (8R,9S,10R,11R,12S)-15-Chloro-14-(4-ethylbenzyl)-2,3,4,5,7,8,9,10,11,12-decahydro-8,12-epoxybenzo[g][1,6]dioxacyclotetradecine-9,10,11-triol;

(9) (9R,10S,11R,12R,13S)-16-Chloro-15-(4-ethylbenzyl)-3,4,5,6,8,9,10,11,12,13-decahydro-2H-9,13-epoxybenzo[h][1,7]dioxacyclopentadecine-10,11,12-triol;

(10) (10R,11S,12R,13R,14S)-17-Chloro-16-(4-ethylbenzyl)-2,3,4,5,6,7,9,10,11,12,13,14-dodecahydro-10,14-epoxybenzo[i][1,8]dioxacyclohexadecine-11,12,13-triol;

(11) (8R,9S,10R,11R,12S)-15-Chloro-14-(4-(methylthio)benzyl)-2,3,4,5,7,8,9,10,11,12-decahydro-8,12-epoxybenzo[g][1,6]dioxacyclotetradecine-9,10,11-triol;

(12) (9R,10S,11R,12R,13S)-16-Chloro-15-(4-(methylthio)benzyl)-3,4,5,6,8,9,10,11,12,13-decahydro-2H-9,13-epoxybenzo[h][1,7]dioxacyclopentadecine-10,11,12-triol;

(13) (8R,9S,10R,11R,12S)-15-Chloro-14-((2,3-dihydrobenzo[b][1,4]dioxin-6-yl)-methyl)-2,3,4,5,7,8,9,10,11,12-decahydro-8,12-epoxybenzo[g][1,6]dioxacyclotetradecine-9,10,11-triol;

(14) (9R,10S,11R,12R,13S)-16-Chloro-15-((2,3-dihydrobenzo[b][1,4]dioxin-6-yl)-methyl)-3,4,5,6,8,9,10,11,12,13-decahydro-2H-9,13-epoxybenzo[h][1,7]dioxacyclopentadecine-10,11,12-triol;

(15) (4R,5S,6R,7R,8S)-11-Chloro-10-(4-ethoxybenzyl)-(1aR,14aS)-1a,2,4,5,6,7,8,9,10-octahydro-1H-4,8-epoxybenzo[g]cyclopropa[c][1,6]dioxacyclotetradecine-5,6,7-triol;

(16) (4R,5S,6R,7R,8S)-11-Chloro-10-(4-ethoxybenzyl)-(1aS,14aR)-1a,2,4,5,6,7,8,9,10-octahydro-1H-4,8-epoxybenzo[g]cyclopropa[c][1,6]dioxacyclotetradecine-5,6,7-triol.

The inventive compound of formula I is effective as an inhibitor against sodium-dependent glucose cotransporter (SGLT2), thereby preventing or treating a metabolic disease.

Accordingly, the present invention provides a pharmaceutical composition for preventing or treating a metabolic disorder, which comprises the compound of formula I, or a pharmaceutically acceptable salt or a prodrug thereof as an active ingredient, and a pharmaceutically acceptable carrier.

The metabolic disorder may be diabetes, cardiovascular disease, or hypertension, preferably diabetes.

Further, the present invention provides a method for preventing or treating a metabolic disorder in a mammal, which comprises administering the compound of formula I or a pharmaceutically acceptable salt or a prodrug thereof to the mammal.

Also, the present invention provides a method for inhibiting SGLT2 in a mammal, which comprises administering the compound of formula I or a pharmaceutically acceptable salt or a prodrug thereof to the mammal.

The pharmaceutical composition may be administered orally or parenterally, e.g., intramuscularly or subcutaneously. The formulation for oral administration may take various forms such as a syrup, tablet, capsule, cream and lozenge. A syrup formulation will generally contain a suspension or solution of the compound or its salt in a liquid carrier, e.g., ethanol, peanut oil, olive oil, glycerine or water, optionally with a flavoring or coloring agent. When the composition is in the form of a tablet, any one of pharmaceutical carriers routinely used for preparing solid formulations may be used. Examples of such carriers include magnesium stearate, terra alba, talc, gelatin, acacia, stearic acid, starch, lactose and sucrose. When the composition is in the form of a capsule, any of the routine encapsulation procedures may be employed, e.g., using the aforementioned carriers in a hard gelatin capsule shell. When the composition is formulated in the form of a soft gelatin shell capsule, any of the pharmaceutical carrier routinely used for preparing dispersions or suspensions may be prepared using an aqueous gum, cellulose, silicate or oil. The formulation for intramuscular or subcutaneous administration may take a liquid form such as a solution, suspension and emulsion which includes aqueous solvents such as water, physiological saline and Ringer's solution; or lipophilic solvents such as fatty oil, sesame oil, corn oil and synthetic fatty acid ester.

Preferably the composition is formulated in a specific dosage form for a particular patient.

Each dosage unit for oral administration contains suitably from 0.1 mg to 500 mg, and preferably from 1 mg to 100 mg of the compound of formula I or its pharmaceutically acceptable salt or prodrug.

The suitable daily dosage for oral administration is about 0.01 mg/kg body weight to 40 mg/kg body weight of the compound of formula I or its pharmaceutically acceptable salt or prodrug, and may be administered 1 to 6 times a day, depending on the patient's condition.

The present invention further provides a use of the compound of formula I or a pharmaceutically acceptable salt or a prodrug thereof for the manufacture of a medicament for preventing or treating a metabolic disorder, particularly diabetes.

The compounds of present invention may be prepared by several synthetic procedures. The compounds of the present invention and the preparation thereof will be better understood in connection with the following synthetic schemes, which are merely illustrative of the methods by which the compounds of the invention may be prepared and are not intended to limit the scope of the invention as defined in the appended claims.

GENERAL SYNTHETIC SEQUENCE

The compound of formula I-1 may be prepared in two ways.

In one example, a compound of formula II-3 (a compound of formula I-1 in which Y is a single bond) may be prepared by a) subjecting a compound of formula II-1 to intramolecular alkylation to obtain a compound formula II-2; and b) deprotecting the compound of formula II-2 to obtain a compound of formula II-3:

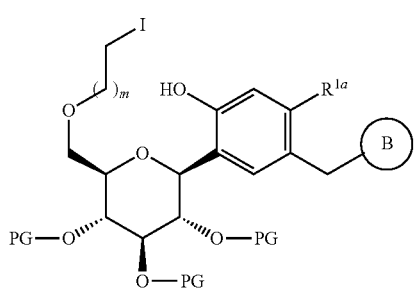

II-1

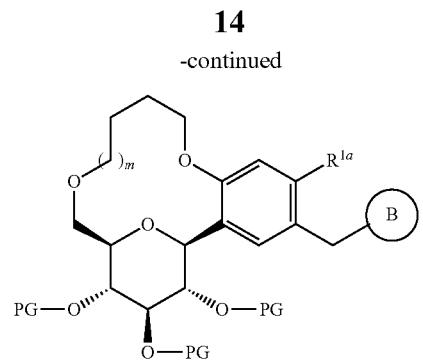

II-2

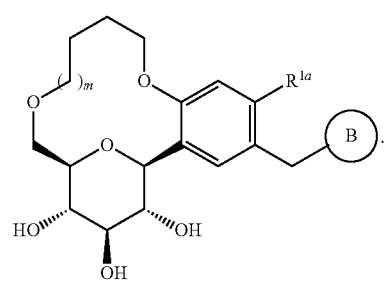

II-3

In other example, a compound of formula II-6 (a compound of formula I-1 in which Y is a double bond) may be prepared by a) subjecting a compound of formula II-4 to ring-closing methathesis using Grubb's catalyst to obtain a compound formula II-5; and b) deprotecting the compound of formula II-5 to obtain a compound of formula II-6:

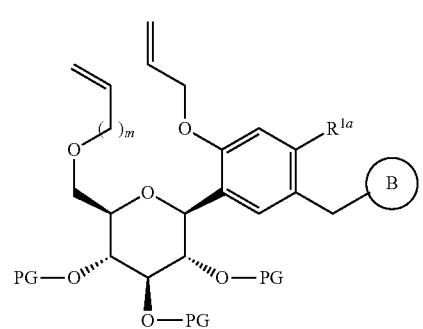

II-4

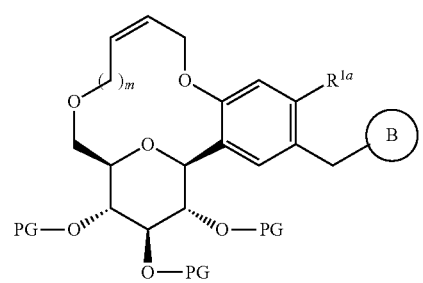

II-5

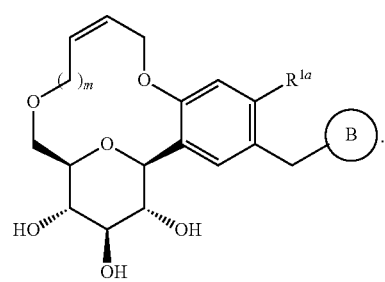

II-6

Hereinafter, the particular examples of the procedure are described in detail.

As shown in Scheme 1, preparation of compounds of formula I commences with preparation of aglycone 8. Thus, 2-chloro-4-hydroxybenzonitrile (1) is brominated selectively to produce structure of 2 with NBS and methanesulfonic acid. The structure of 2 is methylated in dimethylsulfate and LiOH in a suitable solvent such as THF to provide structure of 3. Hydrolysis of 3 with NaOH in an aqueous EtOH, followed by thionyl chloride to produce the corresponding acyl chloride, which is directly treated with ethoxybenzene and aluminum chloride in methylene chloride to generate ketone 5. Subsequent reduction of ketone 5 with triethylsilane in the presence of $BF_3$ etherate produces diphenylmethane 6. The requisite aglycone is further produced by first, demethylation by sodium ethanethiolate in DMF second, allylation with allyl bromide and potassium carbonate in acetone to generate 8.

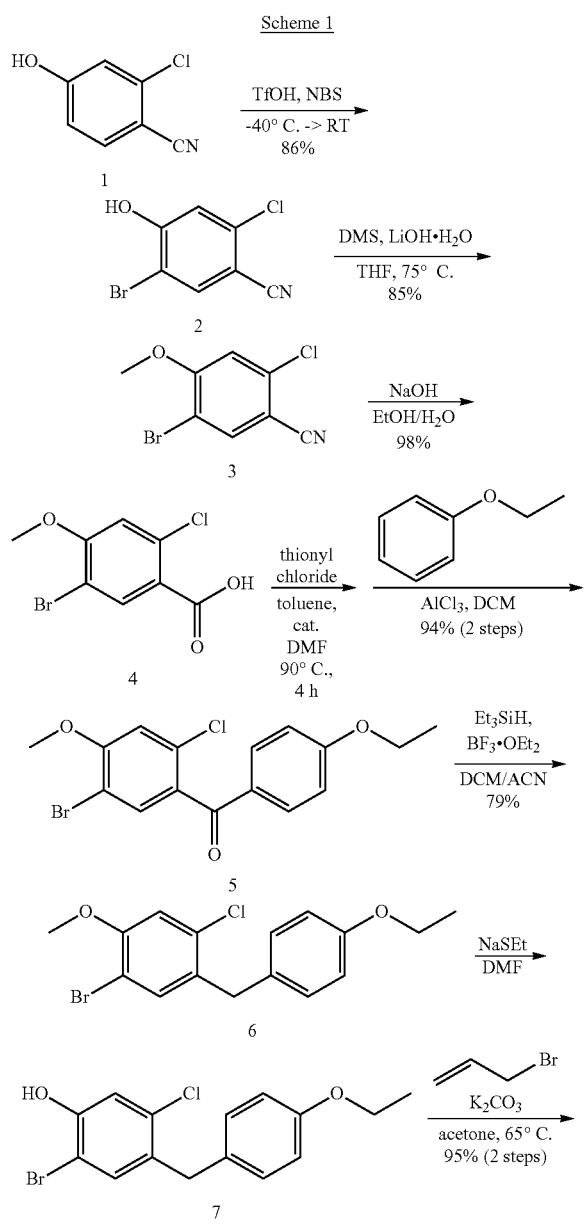

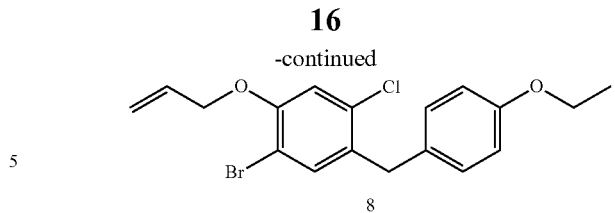

Preparation of the key intermediate 21 is accomplished as shown in Scheme 2. Thus, lithiation and subsequent methylation produces anomeric mixture 10 with concomitant desilylation (Scheme 2). Reduction of 10 with triethylsilane in the presence of boron trifluoride diethyl etherate, and subsequent acetylation of the resulting compound, followed by resolution on EtOH generates beta-anomer tetraacetate 12. Switching acetyl groups on alcohols into benzyl groups is accomplished by hydrolysis with sodium methoxide in MeOH, and subsequent benzylation of the resulting alcohols (e.g. benzyl bromide, NaH, DMF). The requisite alcohol 21 is obtained by selective acetylation of 19 into acetate 20 with TMSOTf and acetic anhydride, and subsequent hydrolysis of the resulting acetate in 97% yields overall.

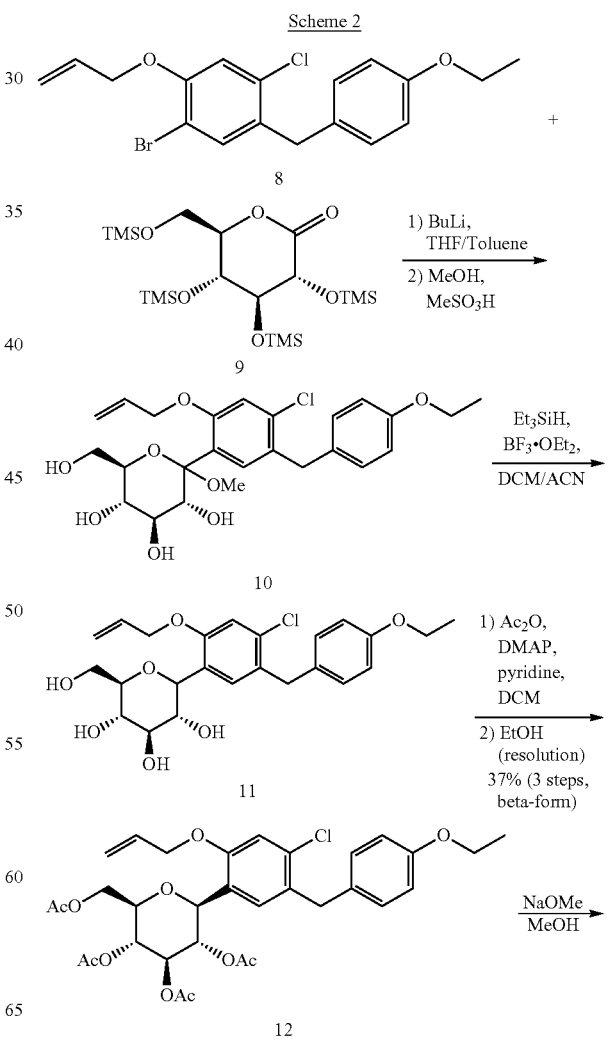

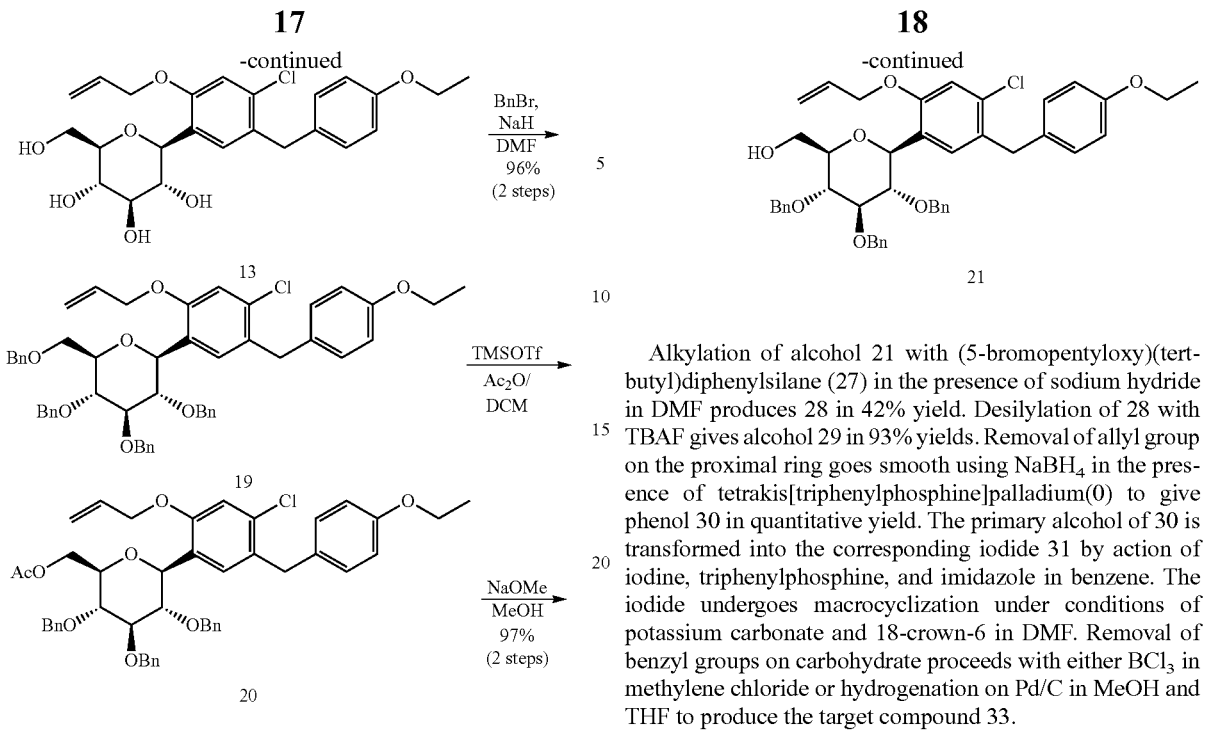

Alkylation of alcohol 21 with (5-bromopentyloxy)(tert-butyl)diphenylsilane (27) in the presence of sodium hydride in DMF produces 28 in 42% yield. Desilylation of 28 with TBAF gives alcohol 29 in 93% yields. Removal of allyl group on the proximal ring goes smooth using NaBH₄ in the presence of tetrakis[triphenylphosphine]palladium(0) to give phenol 30 in quantitative yield. The primary alcohol of 30 is transformed into the corresponding iodide 31 by action of iodine, triphenylphosphine, and imidazole in benzene. The iodide undergoes macrocyclization under conditions of potassium carbonate and 18-crown-6 in DMF. Removal of benzyl groups on carbohydrate proceeds with either BCl₃ in methylene chloride or hydrogenation on Pd/C in MeOH and THF to produce the target compound 33.

Scheme 3

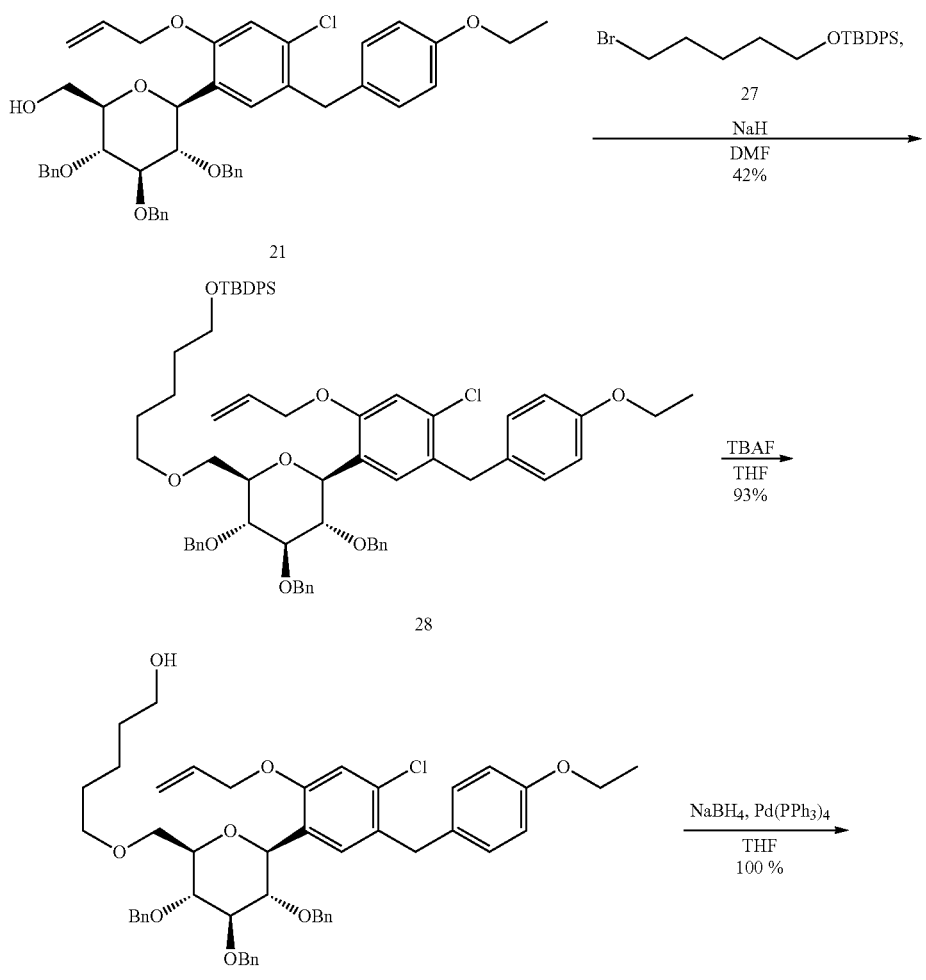

-continued

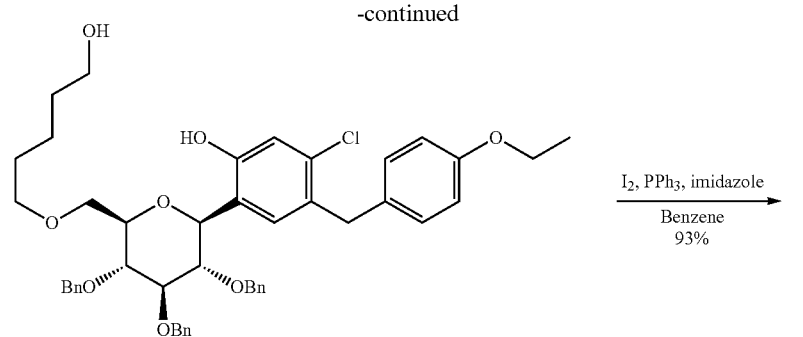

30

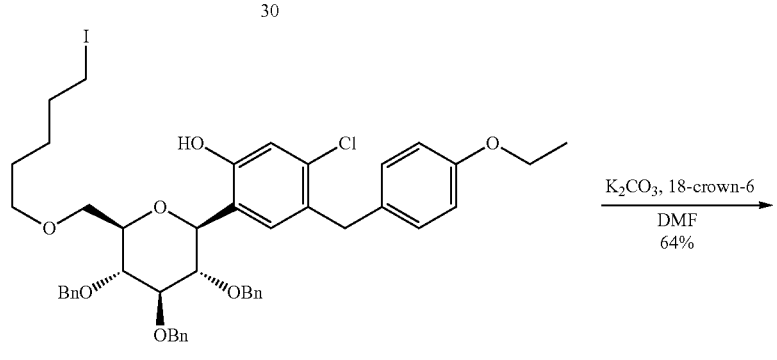

31

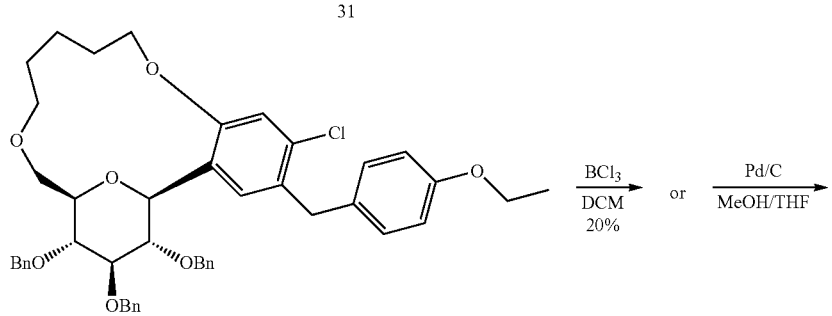

32

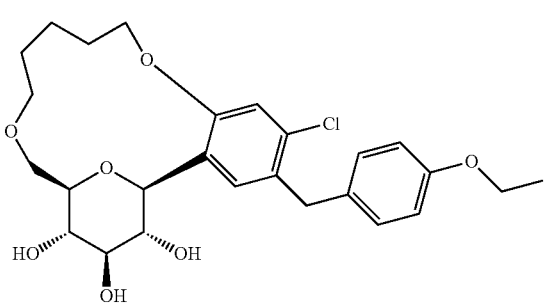

33

Another approach toward macrocyclization involves ring-closing olefin metathesis (RCM) as described in Scheme 4. Thus, compound 13 is treated with 3,3-dimethoxyprop-1-ene in the presence of CSA (10-camphorsulfonic acid) in DMF to provide the 2-vinyl-1,3-dioxane 14. Selective and reductive ring opening using TfOH (trifluoromethanesulfonic acid) and sodium cyanoborohydride produced compound 15. Ring-closing olefin metathesis undergoes on divinyl intermediate 16 using Grubbs $2^{nd}$ generation catalyst in moderate yield. Finally, removal of acetyl groups is accomplished using sodium methoxide in methanol to generate the target compound 18.

Scheme 4

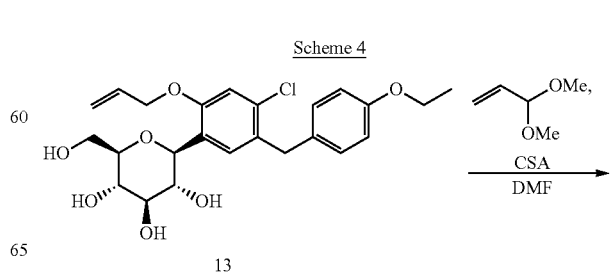

13

-continued

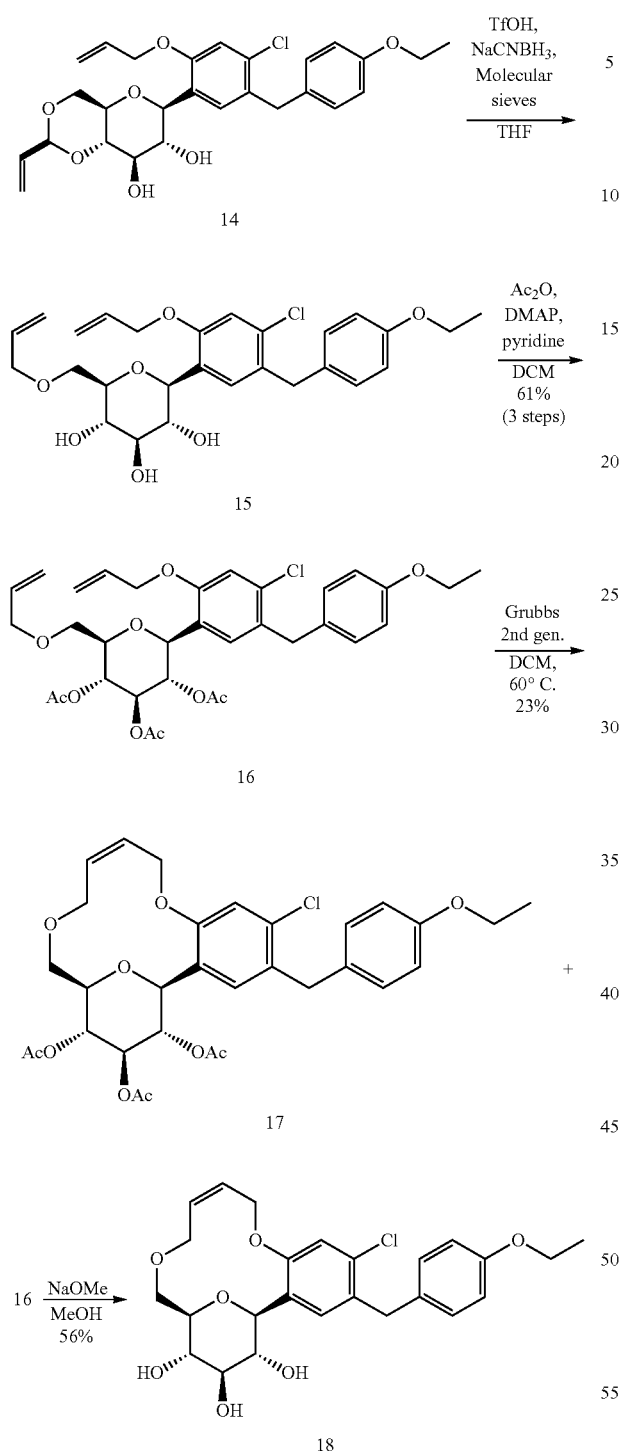

Another way of performing RCM is described in Scheme 5. Thus, compound 21 produced in Scheme 2, is allylated (allyl bromide, sodium hydride, DMF) to produce diene 22. Ring-closing metathesis (RCM) using Grubbs $2^{nd}$ generation catalyst generates macrocycle 23 along with recovered 22.

Finally, subjection of 23 to hydrogen atmosphere on Pd/C in a mixture of MeOH and THF produces the target compound 24 in 22% yields.

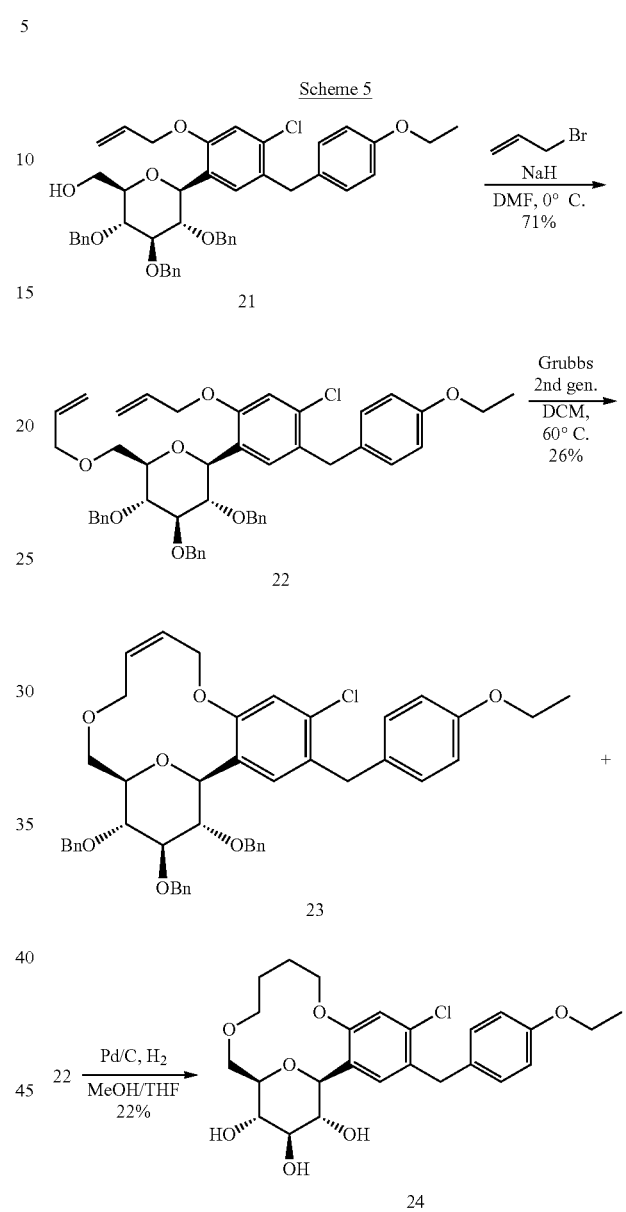

Extension of macrocyclization involves formation of cyclopropane-containing macrocycle. Preparation of these intermediates is shown in Scheme 6. Thus, deallylation of compound 20 proceeds smoothly using sodium borohydride in the presence of tetrakis(triphenylphosphine)palladium(0) in THF to provide the phenol 45. Mitsunobu coupling reaction of 45 with (Z)-but-2-ene-1,4-diol in the presence of triphenylphosphine and diisopropyl azodicarboxylate (DIAD) in THF provides the alcohol 46 in high yields. Simmons-Smith cyclopropanation of 46 ($CH_2I_2$, $ZnEt_2$ in $CH_2Cl_2$) provides a diastereomeric mixture of 47a and 47b in quantitative yields as shown in Scheme 6. These two compounds are separated by using prep HPLC and assigned tentatively as 47a and 47b.

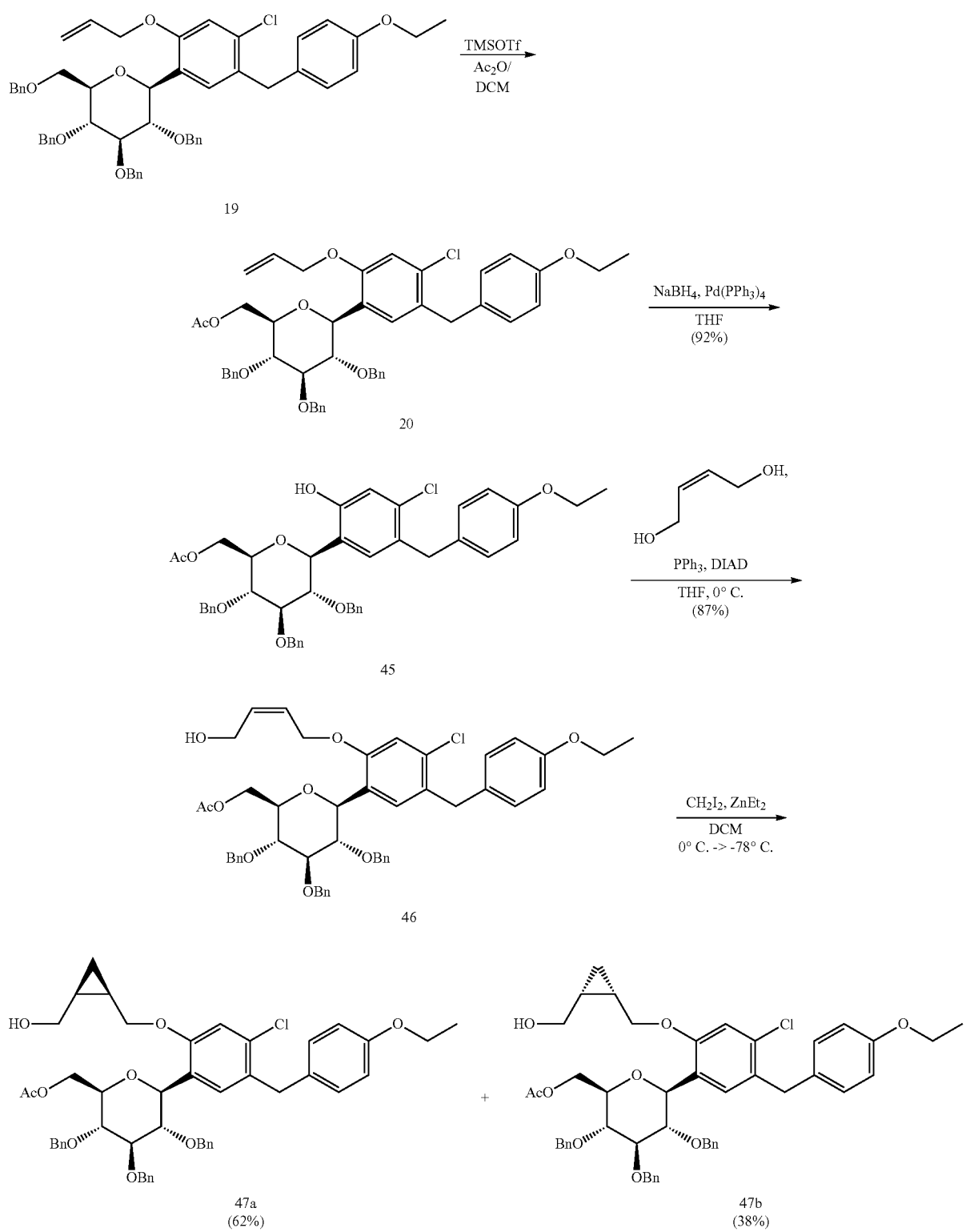
Scheme 6
Cyclopropane 47b is converted into the corresponding iodide 48 using iodine, triphenylphosphine, and imidazole in benzene as shown in Scheme 7. Methanolysis of 48 produces the corresponding alcohol 49. Compound 49 undergoes intramolecular Williamson-type cyclization under conditions of sodium hydride in a suitable solvent such as DMF. Final debenzylation using hydrogen atmosphere on Pd/C in a mixture of MeOH and THF provides the target compound 51. The other diastereomer also follows the same reaction sequence to provide the corresponding macrocycle 55.

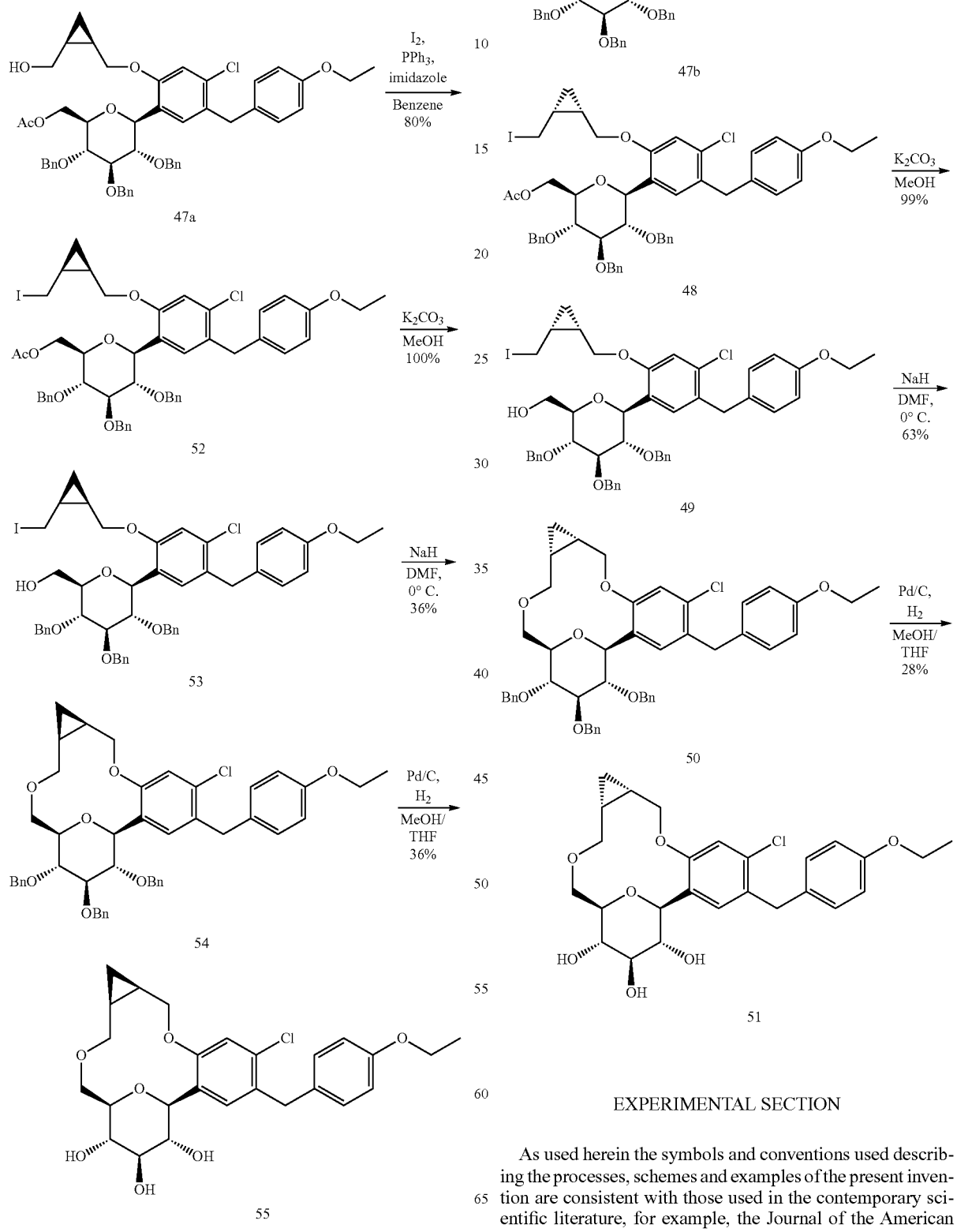

Scheme 7

EXPERIMENTAL SECTION

As used herein the symbols and conventions used describing the processes, schemes and examples of the present invention are consistent with those used in the contemporary scientific literature, for example, the Journal of the American Chemical Society or the Journal of Biological Chemistry.

Hz (Hertz)
T$_r$ (retention time)
MeOH (methanol)
TFA (trifluoroacetic acid)
EtOH (ethanol)
DMSO (dimethylsulfoxide)
DCM (dichloromethane)
DMF (N,N-dimethylformamide)
CDI (1,1-carbonyldiimidazole)
TES (Triethylsilyl)
HOBt (1-hydroxybenzotriazole)
Boc (tert-butyloxycarbonyl)
mCPBA (meta-chloroperbenzoic acid)
NMM (N-methyl morpholine)
TBAF (tetra-n-butylammonium fluoride)
DMAP (4-dimethylaminopyridine)
HPLC (high pressure liquid chromatography)
EDCI (1-ethyl-3-[3-dimethylaminopropyl]carbodiimide hydrochloride)
DME (1,2-dimethoxyethane)
AIBN (2,2'-azobis(2-methylpropionitrile))
DIEA (N,N'-diisopropylethylamine)
TMSI (iodotrimethylsilane)
TMSOTf (trimethylsilyl trifluoromethanesulfonate)
DDQ (2,3-dichloro-5,6-dicyano-p-benzoquinone)
DAST (diethylaminosulfur trifluoride)
NMP (1-methyl-2-pyrrolidinone)
MW (microwave irradiation)
TLC (thin layer chromatography)
RP (reverse phase)
i-PrOH (isopropanol)
TEA (triethylamine)
THF (tetrahydrofuran)
EtOAc (ethyl acetate)
HOAc (acetic acid)
Ac (acetyl)
Bn (benzyl)
NBS (N-bromosuccinimide)
CSA (10-camphorsulfonic acid)
TfOH (trifluoromethanesulfonic acid)
DIAD (diisopropyl azodicarboxylate)

All reactions are conducted under an inert atmosphere at room temperature, unless otherwise noted. n-Butyllithium (Aldrich) was titrated with N-benzylbenzamide as indicator. All reagents were purchased at the highest commercial quality and used without further purification, unless otherwise indicated. All experiment involving moisture- and/or air-sensitive compounds were performed in oven- and/or flame-dried glassware with rubber septa under a positive pressure of nitrogen using standard Schlenck technique. Microwave reaction was conducted with a Biotage Initiator microwave reactor. NMR spectra were obtained on a Bruker 400-MR (400 MHz $^1$H, 100 MHz $^{13}$C) spectrometer. NMR spectra were recorded in ppm (δ) relative to tetramethylsilane (δ=0.00) as an internal standard unless stated otherwise and are reported as follows: chemical shift, multiplicity (s=singlet, d=doublet, t=triplet, q=quartet, m=multiplet, and br=broad), coupling constant, and integration. $^{13}$C NMR spectra were referenced to the residual chloroform-d$_1$ (δ=77.0) or DMSO-d$_6$ (δ=39.7). Mass spectra were obtained with an Agilent 6110 quadruple LC-MSD (ESI+). High resolution mass spectra were obtained on a Jeol JMS-700 Mstation (10 kV, HFAB). Optical rotations were obtained on a Rudolph Autopol III digital polarimeter. Preparative HPLC purifications were performed on a Gilson purification system or Waters purification system. For preparative HPLC, ca. 100 mg of a product was injected in 1 mL of methanol onto a SunFire Prep C18 OBD 5 μm 30×100 mm Column with a 30 min gradient from 5 to 90% acetonitrile in water and a 45 mL/min flow rate. Biotage SP1 and Isolera purification systems were used for normal phase column chromatography with ethyl acetate and hexane. Flash chromatography was performed using E. Merck 230-400 mesh silica gel according to the procedure of Still et al (*J. Org. Chem.* 43, 2923, 1978). Reactions were monitored by either thin-layer chromatography (TLC) on 0.25 mm E. Merck silica gel plates (60E-254) using UV light and p-anisaldehyde solution as visualizing agents or HPLC analysis on an Agilent 1200 series system.

The following synthetic schemes are merely illustrative of the methods by which the compounds of the invention may be prepared and are not intended to limit the scope of the invention as defined in the appended claims.

EXAMPLE 1

(8R,9S,10R,11R,12S)-15-Chloro-14-(4-ethoxybenzyl)-2,5,7,8,9,10,11,12-octahydro-2H-8,12-epoxy-benzo[g][1,6]dioxacyclotetradecine-9,10,11-triol (18)

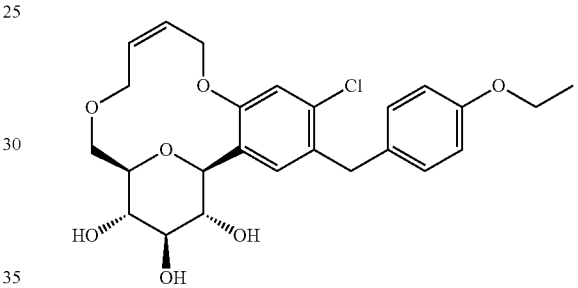

INTERMEDIATE 1

1-(Allyloxy)-2-bromo-5-chloro-4-(4-ethoxybenzyl)benzene (8)

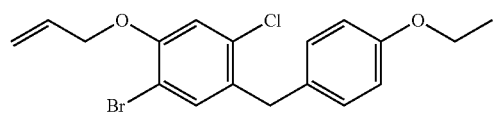 [SMILES: C=CCOc1cc(Cl)c(Cc2ccc(OCC)cc2)cc1Br]

Step 1: 5-Bromo-2-chloro-4-hydroxybenzonitrile (2)

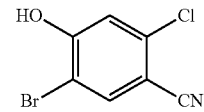 [SMILES: N#Cc1cc(Br)c(O)cc1Cl]

To a solution of 2-chloro-4-hydroxybenzonitrile (1, 10 g, 65 mmol) in acetonitrile (200 mL) at −30° C. was added dropwise trifluoromethanesulfonic acid (10 mL, 71 mmol). The solution was stirred for 10 min at −30° C., before adding of N-bromosuccinimide (16.2 g, 91 mmol). After 18 h stirring at ambient temperature, the solution was quenched with aqueous saturated sodium hydrogen carbonate. The organic layer was extracted with ethyl acetate two times, washed with brine, dried over magnesium sulfate, filtered and concentrated in vacuo. The resulting crude residue was purified on a Biotage® purification apparatus (silica gel, 5 to 40% ethyl acetate in hexanes gradient) to yield the title compound (13 g, 56 mmol, 86%) as a white solid.

$^1$H NMR (400 MHz, CD$_3$OD) δ 7.84 (s, 1H), 6.99 (s, 1H); MH+ 232.

Step 2: 5-Bromo-2-chloro-4-methoxybenzonitrile (3)

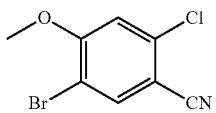

To a solution 5-bromo-2-chloro-4-hydroxybenzonitrile (2, 29 g, 124 mmol) in tetrahydrofuran (500 mL) was added lithium hydroxide monohydrate (6.7 g, 161 mmol) and dimethyl sulfite (15.2 mL, 161 mmol). The resulting mixture was heated at 75° C. for 5 h, re-cooled to room temperature, and quenched with water. The mixture was extracted with ethyl acetate and the organic layer was washed with brine, dried over magnesium sulfate, filtered and evaporated in vacuo. The crude residue was purified on Biotage® purification apparatus (silica gel, 3 to 10% ethyl acetate in hexanes) to yield the title compound (26 g, 104 mmol, 85%) as a white solid.

$^1$H NMR (400 MHz, CDCl$_3$) δ 7.82 (s, 1H), 7.00 (s, 1H), 3.98 (s, 3H).

Step 3: 5-Bromo-2-chloro-4-methoxybenzoic acid (4)

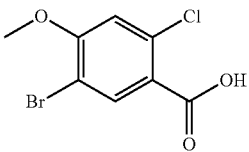

To a solution of 5-bromo-2-chloro-4-methoxybenzonitrile (3, 30.6 g, 124 mmol) in ethanol (450 mL)/H$_2$O (225 mL) was added sodium hydroxide (124 g, 3.1 mol). The solution was refluxed at 100° C. overnight, cooled to room temperature and evaporated to remove ethanol. The aqueous layer was cooled to 0° C., acidified with concentrated hydrogen chloride (190 mL). The generated white solid was filtered, washed with water and dried in vacuo to yield the title compound (32 g, 122 mmol, 98%) as a white solid.

Step 4: (5-Bromo-2-chloro-4-methoxyphenyl)(4-ethoxyphenyl)methanone (5)

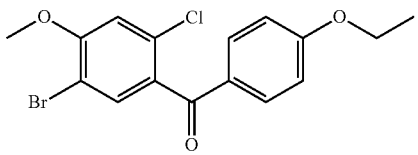 [SMILES: CCOc1ccc(C(=O)c2cc(Br)c(OC)cc2Cl)cc1]

To a solution of 5-bromo-2-chloro-4-methoxybenzoic acid (4, 15 g, 56.5 mmol) in toluene (72 mL) was added thionyl chloride (8.24 mL, 113 mmol) and N,N-dimethylformamide (0.1 mL). The solution was refluxed at 90° C. for 4 h, cooled to room temperature and evaporated to remove toluene and residual reagent. The obtained acyl chloride was diluted with dichloromethane (240 mL) and added portionwise aluminum chloride (8.3 g, 62.2 mmol) and phenetole (7.2 mL, 56.5 mmol) at 0° C. The reaction mixture was stirred at room temperature overnight, quenched with 1N HCl (15 mL) and H$_2$O (15 mL). The organic layer was extracted with dichloromethane two times, washed with 1N HCl and brine, dried over magnesium sulfate, filtered and concentrated in vacuo to yield the title compound as a yellowish solid which was used without further purification.

$^1$H NMR (400 MHz, CDCl$_3$) δ 7.77 (d, J=9.2 Hz, 2H), 7.57 (s, 1H), 6.94 (s, 1H), 6.92 (d, J=9.6 Hz, 2H), 4.11 (q, J=7.2 Hz, 2H), 3.96 (s, 3H), 1.43 (t, J=6.4 Hz, 3H); MH+ 368.

Step 5: 1-Bromo-4-chloro-5-(4-ethoxybenzyl)-2-methoxybenzene (6)

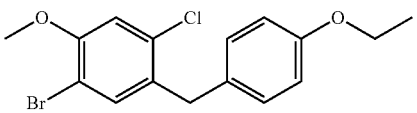 [SMILES: CCOc1ccc(Cc2cc(Br)c(OC)cc2Cl)cc1]

See TAISHO PHARMACEUTICAL CO., LTD, EP1845095 A1, 2007

To a stirred −10° C. solution of (5-Bromo-2-chloro-4-methoxyphenyl)(4-ethoxyphenyl)methanone (54.3 mmol) from Step 4 in dichloromethane (150 mL)/acetonitrile (150 mL) was added triethylsilane (20 mL, 109 mmol) followed by boron trifluoride diethyl etherate (16 mL, 109 mmol) at −10° C. The solution was allowed to warm to 0° C. over 2 h prior to quenching with saturated sodium carbonate solution. After removal of organic volatiles under reduced pressure, the residue was partitioned between ethyl acetate and water. Following extraction of the aqueous layer with ethyl acetate, the combined organic layers were washed with water prior to drying over magnesium sulfate. Filtration and concentration under reduced pressure yielded the title compound as a yellowish solid which was used without further purification.

$^1$H NMR (400 MHz, CDCl$_3$) δ 7.29 (s, 1H), 7.07 (d, J=8.8 Hz, 2H), 6.90 (s, 1H), 6.83 (d, J=8.8 Hz, 2H), 4.00 (q, J=6.8 Hz, 2H), 3.93 (s, 2H), 3.87 (s, 3H), 1.40 (t, J=6.8, 3H).

Step 6: 2-Bromo-5-chloro-4-(4-ethoxybenzyl)phenol (7)

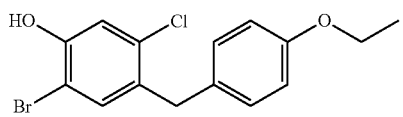 [SMILES: CCOc1ccc(Cc2cc(Br)c(O)cc2Cl)cc1]

To a solution of 1-Bromo-4-chloro-5-(4-ethoxybenzyl)-2-methoxybenzene (6, 11.3 mmol) in N,N-dimethylformamide (50 mL) was added sodium ethane thiolate (3.17 g, 34 mmol) and heated at 90° C. for 3 h. The reaction mixture was cooled to 0° C., neutralized with 1N HCl, and the organic layer was separated and the aqueous layer was extracted with ethyl acetate. The combined organic layers were washed with brine, dried over magnesium sulfate, filtered and concentrated in vacuo to yield the title compound as yellow oil which was used without further purification.

$^1$H NMR (400 MHz, CDCl$_3$) δ 7.26 (s, 1H), 7.07 (d, J=8.4 Hz, 2H), 7.06 (s, 1H), 6.83 (d, J=8.4 Hz, 2H), 4.01 (q, J=6.8 Hz, 2H), 3.93 (s, 2H), 1.40 (t, J=6.8 Hz, 3H).

Step 7: 1-(Allyloxy)-2-bromo-5-chloro-4-(4-ethoxybenzyl)benzene (8)

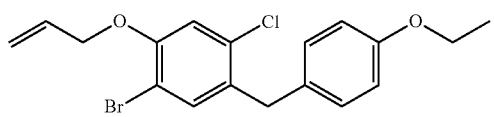 [SMILES: C=CCOc1cc(Cl)c(Cc2ccc(OCC)cc2)cc1Br]

To a solution of 2-Bromo-5-chloro-4-(4-ethoxybenzyl)phenol (7, 55 mmol) in acetone (180 mL) were added potassium carbonate (15.2 g, 110 mmol) and allyl bromide (7 mL, 83 mmol) and heated at 65° C. for 3 h. The insoluble material was removed by filter and the filtrate was evaporated under reduced pressure. The crude residue was purified on Biotage® purification apparatus (silica gel, 3 to 10% ethyl acetate in hexanes) to yield the title compound (21 g, 52 mmol, 95%) as colorless oil.

$^1$H NMR (400 MHz, CDCl$_3$) δ 7.29 (s, 1H), 7.07 (d, J=8.4 Hz, 2H), 6.90 (s, 1H), 6.83 (d, J=8.0 Hz, 2H), 6.09-5.99 (m, 1H), 5.47 (d, J=17.2 Hz, 1H), 5.33 (d, J=10.4 Hz, 2H), 4.57 (d, J=4.8 Hz, 2H), 4.01 (q, J=6.8 Hz, 2H), 3.93 (s, 2H), 1.40 (t, J=6.8, 3H).

INTERMEDIATE 2

((2R,3R,4R,5S,6S)-6-(2-(Allyloxy)-4-chloro-5-(4-ethoxybenzyl)phenyl)-3,4,5-tris(benzyloxy)tetrahydro-2H-pyran-2-yl)methanol (13)

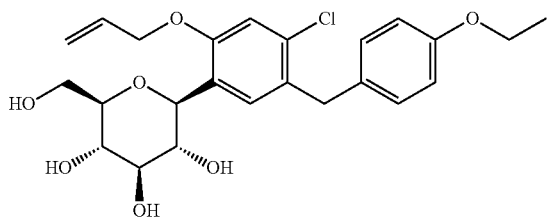 [SMILES: C=CCOc1cc(Cl)c(Cc2ccc(OCC)cc2)cc1[C@@H]1O[C@H](CO)[C@@H](O)[C@H](O)[C@H]1O]

Step 1: (2R,3R,4R,5S,6S)-2-(Acetoxymethyl)-6-(2-(allyloxy)-4-chloro-5-(4-ethoxybenzyl)phenyl)tetrahydro-2H-pyran-3,4,5-triyl triacetate (12)

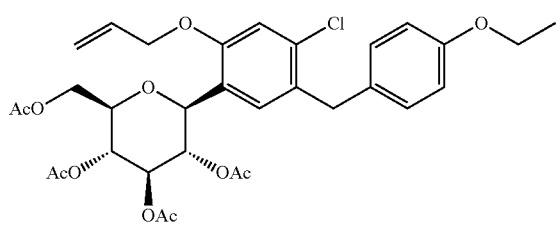 [SMILES: C=CCOc1cc(Cl)c(Cc2ccc(OCC)cc2)cc1[C@@H]1O[C@H](COC(C)=O)[C@@H](OC(C)=O)[C@H](OC(C)=O)[C@H]1OC(C)=O]

To a solution of (8, 10.2 g, 27 mmol) in tetrahydrofuran (25 mL)/toluene (50 mL) at −78° C. under an atmosphere of nitrogen was added dropwise n-butyllithium (2.5 M in hexanes, 12 mL, 30 mmol), and the mixture was stirred for 1 h at the same temperature. Then a solution of 2,3,4,6-tetra-O-trimetylsilyl-β-D-glucolatone (9, 13.8 g, 30 mmol) in tetrahydrofuran (30 mL) was added dropwise, and the mixture was stirred for 1.5 h at the same temperature. The reaction mixture was quenched by addition of saturated ammonium chloride solution. After complete addition, the solution was gradually raised to room temperature. The organic layer was separated and the aqueous layer was extracted with ethyl acetate. The combined organic layers were washed with brine, dried over magnesium sulfate, filtered and concentrated in vacuo to yield the title compound (10) as a yellowish solid which was used without further purification.

To a stirred −25° C. solution of O-methylglucoside (10) in dichloromethane (50 mL)/acetonitrile (50 mL) was added triethylsilane (8.7 mL, 54 mmol) followed by boron trifluoride diethyl etherate (5.2 mL, 41 mmol) at −25° C. The solution was allowed to warm to 0° C. over 3 h prior to quenching with saturated sodium carbonate solution. After removal of organic volatiles under reduced pressure, the residue was partitioned between ethyl acetate and water. Following extraction of the aqueous layer with ethyl acetate, the combined organic layers were washed with water prior to drying over magnesium sulfate. Filtration and removal of volatiles under reduced pressure yielded desired tetraol (11) as a yellowish solid.

The obtained tetraol (11) was diluted dichloromethane (60 mL) and added acetic anhydride (22.2 mL, 235 mmol), DMAP (165 mg, 1.35 mmol) and pyridine (19 mL, 235 mmol). After 18 h, the reaction was quenched by addition of H$_2$O, whereupon the resulting mixture was extracted with dichloromethane (2×). The combined organic layers were washed with 1N HCl (2×) and brine (2×) prior to drying over magnesium sulfate. After filtration and concentration under reduced pressure, residue was slurried in ethanol (80 mL) and heated to reflux with stirring. The reaction mixture was held at reflux for 1 h to ensure that all of solution had homogenized; it was then cooled evenly at 15° C./h to ambient temperature and stirred overnight at this temperature. The resulting solid was isolated by filtration and dried in vacuo to yield the title compound (12, 7.0 g, 11 mmol, 41%, ca. 60% separation yield) as a white solid.

MNa+ 655.

Step 2: (2S,3R,4R,5S,6R)-2-(2-(Allyloxy)-4-chloro-5-(4-ethoxybenzyl)phenyl)-6-(hydroxymethyl)tetrahydro-2H-pyran-3,4,5-triol (13)

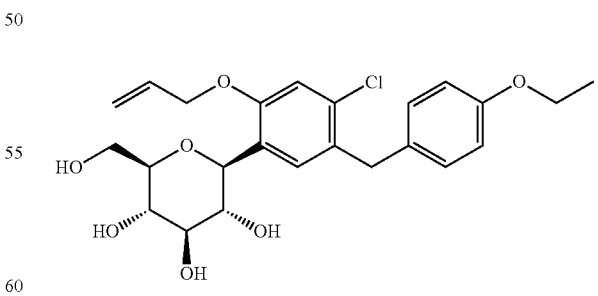

To a solution (2R,3R,4R,5S,6S)-2-(acetoxymethyl)-6-(2-(allyloxy)-4-chloro-5-(4-ethoxybenzyl)phenyl)tetrahydro-2H-pyran-3,4,5-triyl triacetate (12, 4 g, 6.32 mmol) from Step 1 in methanol (90 mL) was added sodium methoxide (25% in methanol, 9 mL) and the reaction mixture was stirred at ambient temperature for 5 h. The solution was cooled to 0° C.

prior to neutralizing with acetic acid (4.5 mL). After removal of organic volatiles under reduced pressure, the residue was diluted with ethyl acetate and water. The organic layer was separated and the aqueous layer was extracted with ethyl acetate. The combined organic layers were washed with sodium hydrogen carbonate and brine, dried over magnesium sulfate, filtered and concentrated in vacuo to yield the title compound (13) as a white solid which was used without further purification.

$^1$H NMR (400 MHz, CDCl$_3$) δ 7.19 (s, 1H), 7.05 (d, J=8.4 Hz, 2H), 6.92 (s, 1H), 6.79 (d, J=8.8 Hz, 2H), 6.06-5.96 (m, 1H), 5.40 (dd, J=1.6, 17.6 Hz, 1H), 5.30 (dd, J=1.6, 10.4 Hz, 1H), 4.66 (d, J=9.6 Hz, 2H), 4.58-4.49 (m, 2H), 4.01-3.96 (m, 4H), 3.89-3.86 (m, 1H), 3.80-3.75 (m, 1H), 3.66-3.62 (m, 2H), 3.55-3.47 (m, 2H), 3.22 (m, 1H), 3.05 (m, 1H), 2.42 (m, 1H), 2.13-2.11 (m, 1H), 1.38 (t, J=6.8 Hz, 3H), MNa+ 487.

INTERMEDIATE 3

(8R,9S,10R,11R,12S)-9,10,11-Tris(acetyloxy)-15-chloro-14-(4-ethoxybenzyl)-2,5,7,8,9,10,11,12-octahydro-2H-8,12-epoxybenzo[g][1,6]dioxacyclotetradecine (17)

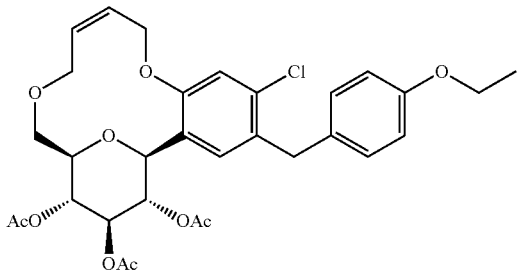 [SMILES: CCOc1ccc(Cc2cc3c(cc2Cl)OC/C=C\COC[C@H]2O[C@@H]3[C@H](OC(C)=O)[C@@H](OC(C)=O)[C@@H]2OC(C)=O)cc1]

Step 1: (4$^a$R,6S,7R,8R,8$^a$S)-6-(2-(Allyloxy)-4-chloro-5-(4-ethoxybenzyl)phenyl)-2-vinylhexahydropyrano[3,2-d][1,3]dioxine-7,8-diol (14)

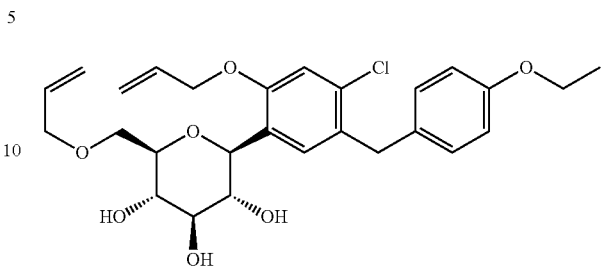

To a solution of intermediate tetraol (13, 500 mg, 1.08 mmol) in N,N-dimethylformamide (3 mL) under an atmosphere of nitrogen were added acrolein diethyl acetal (0.51 mL, 3.23 mmol) and camphorsulfonic acid (64 mg, 0.26 mmol), and the mixture was stirred at the same temperature overnight. The reaction mixture was quenched by addition of triethylamine (0.045 mL, 0.32 mmol) and the removal of volatiles under reduced pressure yielded desired acetal compound (14) as a white-off solid which was used without further purification.

MNa+ 525.

Step 2: (2S,3R,4R,5S,6R)-2-(2-(Allyloxy)-4-chloro-5-(4-ethoxybenzyl)phenyl)-6-(allyloxymethyl)tetrahydro-2H-pyran-3,4,5-triol (15)

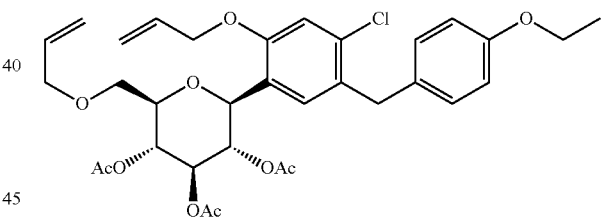

To a solution (4$^a$R,6S,7R,8R,8$^a$S)-6-(2-(allyloxy)-4-chloro-5-(4-ethoxybenzyl)phenyl)-2-vinylhexahydropyrano[3,2-d][1,3]dioxine-7,8-diol (14, 669 mg, 1.33 mmol) from Step 1 in tetrahydrofuran (13 mL) was added sodium cyanoborohydride (642 mg, 9.71 mmol), molecular sieves (407 mg) and was added cautiously trifluoromethanesulfonic acid. After addition, the mixture was stirred for another 0.5 h, before being poured into H$_2$O. The aqueous phase was extracted with dichloromethane and the combined organic fractions were washed with brine. The organic layer was dried over magnesium sulfate and filtered through a pad of silica gel. The filtrate was evaporated and went to next step.

MNa+ 527.

Step 3: (2S,3S,4R,5R,6R)-2-(2-(Allyloxy)-4-chloro-5-(4-ethoxybenzyl)phenyl)-6-(allyloxymethyl)tetrahydro-2H-pyran-3,4,5-triyl triacetate (16)

The obtained triol (15) was diluted with dichloromethane (15 mL) and added acetic anhydride (1.1 mL, 12.1 mmol), DMAP (9.2 mg, 0.076 mmol) and pyridine (1.0 mL, 12.11 mmol). After 18 h, the reaction was quenched by addition of H$_2$O, whereupon the resulting mixture was extracted with dichloromethane (2×). The combined organic layers were washed with 1N HCl (2×) and brine (2×) prior to drying over magnesium sulfate. After filtration and concentration under reduced pressure, the resulting oil was purified on Biotage® purification apparatus (silica gel, 5 to 30% tetrahydrofuran in hexanes) to yield the title compound (16, 580 mg, 0.92 mmol, 61%; 3 steps) as a white solid.

$^1$H NMR (400 MHz, CDCl$_3$) δ 7.20 (s, 1H), 7.04 (d, J=8.8 Hz, 2H), 6.84 (s, 1H), 6.79 (d, J=8.4 Hz, 2H), 6.07-5.99 (m, 1H), 5.85-5.78 (m, 1H), 5.44 (dd, J=1.6, 17.6 Hz, 1H), 5.34-5.23 (m, 3H), 5.19-50.13 (m, 2H), 4.82 (d, J=9.2 Hz, 1H), 4.50 (d, J=4.0 Hz, 1H), 4.02-3.90 (m, 6H), 3.79-3.74 (m, 1H), 3.53 (d, J=4.4 Hz, 1H), 2.04 (s, 3H), 2.00 (s, 3H), 1.74 (s, 3H), 1.39 (t, J=7.2 Hz, 3H); MNa+ 653.

Step 4: (8R,9S,10R,11R,12S)-9,10,11-Tris(acetyloxy)-15-chloro-14-(4-ethoxybenzyl)-2,5,7,8,9,10,11,12-octahydro-2H-8,12-epoxybenzo[g][1,6]dioxacyclotetradecine (17)

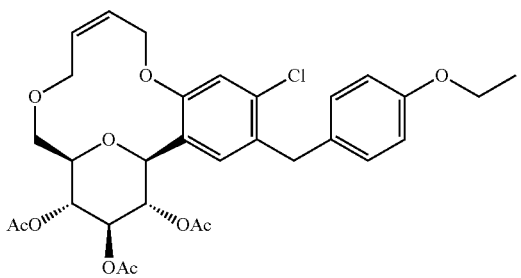 [SMILES: CCOc1ccc(Cc2cc3c(cc2Cl)OC/C=C\COC[C@H]2O[C@@H]3[C@H](OC(C)=O)[C@@H](OC(C)=O)[C@@H]2OC(C)=O)cc1]

To a solution of (2S,3S,4R,5R,6R)-2-(2-(allyloxy)-4-chloro-5-(4-ethoxybenzyl)phenyl)-6-(allyloxymethyl)tetrahydro-2H-pyran-3,4,5-triyl triacetate (16, 580 mg, 0.92 mmol) from Step 3 in dichloromethane (184 mL, 0.005M) under an atmosphere of nitrogen was added Grubbs $2^{nd}$ generation catalyst (156 mg, 0.184 mmol), and the mixture was heated at 60° C. for 3 days. After re-cooling to room temperature, the reaction mixture was filtered through a pad of Celite®, washed with ethyl acetate (20 mL) and the filtrated was evaporated under reduced pressure. The resulting crude residue was purified on a Biotage® purification apparatus (silica gel, 5 to 20% tetrahydrofuran in hexanes gradient) to yield the title compound (17, (4-form, 125 mg, 0.208 mmol, 23%) as a white solid.

$^1$H NMR (400 MHz, CDCl$_3$) δ 7.22 (s, 1H), 7.18 (s, 1H), 7.11 (d, J=8.4 Hz, 2H), 6.82 (d, J=8.8 Hz, 2H), 5.95-5.87 (m, 1H), 5.72 (dt, J=4.0, 15.2 Hz, 1H), 5.56 (t, J=9.2 Hz, 1H), 5.35-5.28 (m, 1H), 4.92 (t, J=10.0 Hz, 1H), 4.77-4.67 (m, 2H), 4.41-4.36 (m, 1H), 4.14-4.11 (m, 1H), 4.05-3.94 (m, 5H), 3.72 (t, J=8.8 Hz, 1H), 3.65 (d, J=13.2 Hz, 1H), 3.54-3.48 (m, 1H), 2.07 (s, 3H), 2.02 (s, 3H), 1.75 (s, 3H), 1.41 (t, J=7.2 Hz, 3H); MNa+ 625.

Step 5: (8R,9S,10R,11R,12S)-15-Chloro-14-(4-ethoxybenzyl)-2,5,7,8,9,10,11,12-octahydro-2H-8,12-epoxybenzo[g][1,6]dioxacyclotetradecine-9,10,11-triol (18)

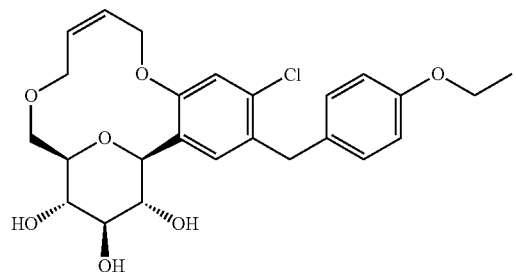 [SMILES: CCOc1ccc(Cc2cc3c(cc2Cl)OC/C=C\COC[C@H]2O[C@@H]3[C@H](O)[C@@H](O)[C@@H]2O)cc1]

To a solution of (2S,3S,4R,5R,6R)-2-(2-(allyloxy)-4-chloro-5-(4-ethoxybenzyl)phenyl)-6-(allyloxymethyl)tetrahydro-2H-pyran-3,4,5-triyl triacetate (17, 125 mg, 0.208 mmol) from Step 4 in methanol (4 mL) was added sodium methoxide (25% in methanol, 0.6 mL) and the reaction mixture was stirred at ambient temperature for 1 h. The solution was cooled to 0° C. prior to neutralizing with acetic acid (0.3 mL). After removal of organic volatiles under reduced pressure, the residue was diluted with methanol. Purification by reverse phase preparative HPLC (Waters®, SunFire™ Prep, 5 to 50% acetonitrile in water gradient) provided the title compound (18, 56 mg, 0.117 mmol, 56%) as a white solid.

$^1$H NMR (400 MHz, DMSO-d$_6$) δ 7.33 (s, 1H), 7.30 (s, 1H), 7.29 (d, J=8.4 Hz, 2H), 6.82 (d, J=8.8 Hz, 2H), 5.86-5.80 (m, 1H), 5.72 (dt, J=7.6, 15.2 Hz, 1H), 5.07 (d, J=4.4 Hz, 1H), 5.01 (d, J=5.6 Hz, 1H), 4.79 (d, J=6.0 Hz, 1H), 4.62 (dd, J=8.8, 12.0 Hz, 1H), 4.38 (dd, J=5.6, 11.6 Hz, 1H), 4.23 (d, J=10.0 Hz, 1H), 4.00-3.88 (m, 6H), 3.83 (d, J=11.6 Hz, 1H), 3.66-3.60 (m, 1H), 3.28-3.24 (m, 3H), 2.98-2.93 (m, 1H), 1.30 (t, J=7.2 Hz, 3H); MH+ 499, IR (neat, cm$^{-1}$) 3425, 2922, 1607, 1511, 1485, 1245, 1079, 1028, 974, 826,

EXAMPLE 2

(8R,9S,10R,11R,12S)-15-Chloro-14-(4-ethoxybenzyl)-2,3,4,5,7,8,9,10,11,12-decahydro-2H-8,12-epoxybenzo[g][1,6]dioxacyclotetradecine-9,10,11-triol (24)

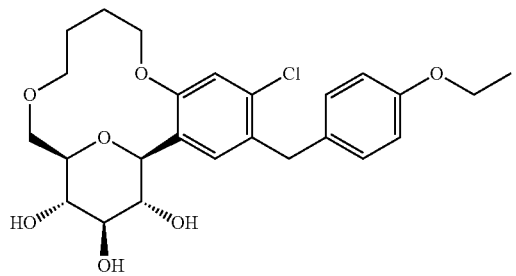 [SMILES: CCOc1ccc(Cc2cc3c(cc2Cl)OCCCCOC[C@H]2O[C@@H]3[C@H](O)[C@@H](O)[C@@H]2O)cc1]

INTERMEDIATE 4

((2R,3R,4R,5S,6S)-6-(2-(Allyloxy)-4-chloro-5-(4-ethoxybenzyl)phenyl)-3,4,5-tris(benzyloxy)tetrahydro-2H-pyran-2-yl)methanol (21)

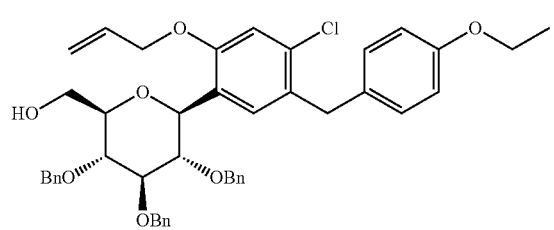 [SMILES: C=CCOc1cc(Cl)c(Cc2ccc(OCC)cc2)cc1[C@@H]1O[C@H](CO)[C@@H](OCc2ccccc2)[C@H](OCc2ccccc2)[C@H]1OCc1ccccc1]

Step 1: (2S,3S,4R,5R,6R)-2-(2-(Allyloxy)-4-chloro-5-(4-ethoxybenzyl)phenyl)-3,4,5-tris(benzyloxy)-6-(benzyloxymethyl)tetrahydro-2H-pyran (19)

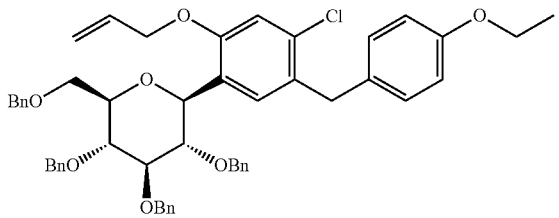 [SMILES: C=CCOc1cc(Cl)c(Cc2ccc(OCC)cc2)cc1[C@@H]1O[C@H](COCc2ccccc2)[C@@H](OCc2ccccc2)[C@H](OCc2ccccc2)[C@H]1OCc1ccccc1]

To a solution of tetraol (13, 8.4 g, 18 mmol) from Step 2 in N,N-dimethylformamide (100 mL) at 0° C. under an atmosphere of nitrogen was added sodium hydride (60% dispersion in mineral oil, 10.1 g, 252 mmol), and the mixture was stirred for 30 min at the same temperature. Then benzyl bromide (19.5 mL, 162 mmol) was added dropwise, and the mixture was stirred with gradual warming to ambient temperature over 5 h. After re-cooling to 0° C., the reaction mixture was quenched by addition of water (100 mL). The mixture was diluted with water and extracted with ethyl acetate. The organic layer was washed with brine, dried over magnesium sulfate, filtered and evaporated in vacuo. The resulting crude residue was purified on a Biotage® purification apparatus (silica gel, 5 to 20% tetrahydrofuran in hexanes gradient) to yield the title compound (19, 14.8 g, 18 mmol, 100%) as a white solid.

$^1$H NMR (400 MHz, DMSO-$d_6$) δ 7.43 (br, 2H), 7.33-7.25 (m, 12H), 7.21-7.13 (m, 5H), 7.06-7.04 (m, 3H), 6.83 (d, J=6.4 Hz, 1H), 6.71 (d, J=8.8 Hz, 1H), 6.00-5.93 (m, 1H), 5.38 (d, J=17.2 Hz, 1H), 5.18 (dd, J=1.6, 10.8 Hz, 1H), 4.80 (s, 2H), 4.76 (d, J=11.2 Hz, 1H), 4.59-4.40 (m, 6H), 3.94-3.86 (m, 5H), 3.75 (m, 2H), 3.63-3.58 (m, 4H), 1.26 (t, J=6.8 Hz, 3H); MNa+ 847.

Step 2: ((2R,3R,4R,5S,6S)-6-(2-(Allyloxy)-4-chloro-5-(4-ethoxybenzyl)phenyl)-3,4,5-tris(benzyloxy)tetrahydro-2H-pyran-2-yl)methyl acetate (20)

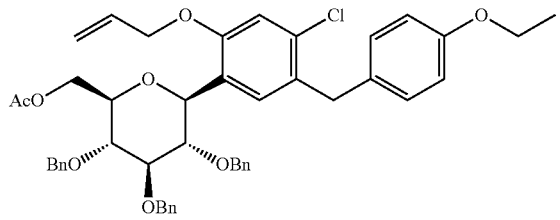

To a stirred −55° C. solution of (2S,3S,4R,5R,6R)-2-(2-(allyloxy)-4-chloro-5-(4-ethoxybenzyl)phenyl)-3,4,5-tris(benzyloxy)-6-(benzyloxymethyl)tetrahydro-2H-pyran (19, 8.54 g, 10 mmol) from Step 3 in acetic anhydride (50 mL)/dichloromethane (50 mL) was dropwise added trimethylsilyl trifluoromethanesulfonate (4.7 mL, 26 mmol) at a rate such that the reaction temperature was maintained between −50 and −55° C. The solution was allowed to warm to −45° C. over 1.5 h prior to quenching with saturated sodium hydrogen carbonate solution. The reaction mixture was extracted with dichloromethane and the combined organic layers were washed with saturated sodium hydrogen carbonate solution prior to drying over magnesium sulfate. After filtration and concentration under reduced pressure, the crude residue was purified on a Biotage® purification apparatus (silica gel, 5 to 20% tetrahydrofuran in hexanes gradient) to yield the title compound (20, 7.8 g, 10 mmol, 100%) as a white solid.
MNa+ 799.

Step 3: ((2R,3R,4R,5S,6S)-6-(2-(Allyloxy)-4-chloro-5-(4-ethoxybenzyl)phenyl)-3,4,5-tris(benzyloxy)tetrahydro-2H-pyran-2-yl)methanol

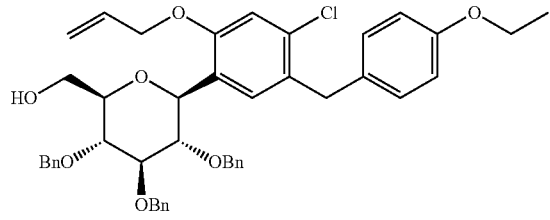 [SMILES: C=CCOc1cc(Cl)c(Cc2ccc(OCC)cc2)cc1[C@@H]1O[C@H](CO)[C@@H](OCc2ccccc2)[C@H](OCc2ccccc2)[C@H]1OCc1ccccc1]

To a solution of ((2R,3R,4R,5S,6S)-6-(2-(allyloxy)-4-chloro-5-(4-ethoxybenzyl)phenyl)-3,4,5-tris(benzyloxy)tetrahydro-2H-pyran-2-yl)methyl acetate (20, 7.8 g, 10 mmol) from Step 4 in methanol (130 mL) was added sodium methoxide (25% in methanol, 13 mL) and the reaction mixture was vigorously stirred at ambient temperature for 5 h. The solution was cooled to 0° C. prior to neutralizing with acetic acid (6.5 mL). After removal of organic volatiles under reduced pressure, the residue was diluted ethyl acetate and water. The organic layer was separated and the aqueous layer was extracted with ethyl acetate. The combined organic layers were washed with sodium hydrogen carbonate and brine, dried over magnesium sulfate, filtered and concentrated in vacuo. The crude residue was purified on Biotage® purification apparatus (silica gel, 5 to 30% tetrahydrofuran in hexanes) to yield the title compound (21, 7.2 g, 9.8 mmol, 98%) as a white solid.
MNa+ 757.

INTERMEDIATE 5

(Z)-(8R,9S,10R,11R,12S)-9,10,11-Tris(benzyloxy)-15-chloro-14-(4-ethoxybenzyl)-2,3,4,5,7,8,9,10,11,12-decahydro-2H-8,12-epoxybenzo[g][1,6]dioxacyclotetradecine (23)

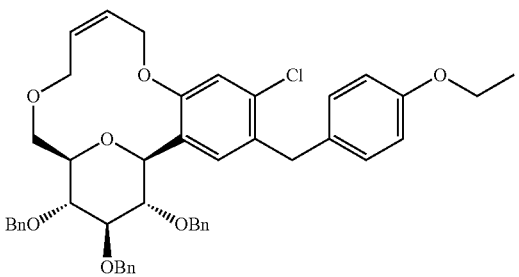

Step 1: (2S,3S,4R,5R,6R)-2-(2-(allyloxy)-4-chloro-5-(4-ethoxybenzyl)phenyl)-6-(allyloxymethyl)-3,4,5-tris(benzyloxy)tetrahydro-2H-pyran (22)

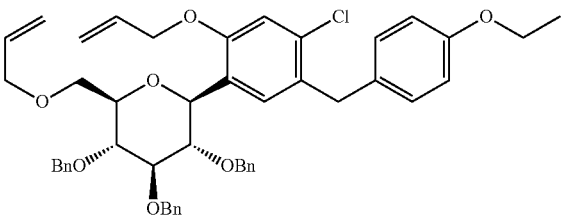 [SMILES: C=CCOC[C@H]1O[C@@H](c2cc(Cc3ccc(OCC)cc3)c(Cl)cc2OCC=C)[C@H](OCc2ccccc2)[C@@H](OCc2ccccc2)[C@@H]1OCc1ccccc1]

To a solution of primary alcohol (21, 1.5 g, 2.04 mmol) from Step 1 in N,N-dimethylformamide (10 mL) at 0° C. under an atmosphere of nitrogen was added sodium hydride (60% dispersion in mineral oil, 123 mg, 3.06 mmol), and the mixture was stirred for 30 min at the same temperature. Then allyl bromide (0.26 mL, 3.06 mmol) was added dropwise, and the mixture was stirred with gradual warming to ambient temperature over 5 h. After re-cooling to 0° C., the reaction mixture was quenched by addition of water (10 mL). The mixture was diluted with saturated ammonium chloride and extracted with ethyl acetate. The organic layer was washed with brine, dried over magnesium sulfate, filtered and evaporated in vacuo. The resulting crude residue was purified on a Biotage® purification apparatus (silica gel, 5 to 20% tetrahydrofuran in hexanes gradient) to yield the title compound (22, 1.12 g, 1.44 mmol, 71%) as a white solid.
MNa+ 797.

Step 2: (Z)-((8R,9S,10R,11R,12S)-9,10,11-Tris(benzyloxy)-15-chloro-14-(4-ethoxybenzyl)-2,3,4,5,7,8,9,10,11,12-decahydro-2H-8,12-epoxybenzo[g][1,6]dioxa-cyclotetradecine (23)

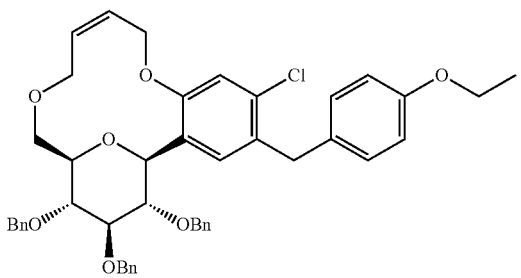

To a solution of (2S,3S,4R,5R,6R)-2-(2-(allyloxy)-4-chloro-5-(4-ethoxybenzyl)phenyl)-6-(allyloxymethyl)-3,4,5-tris(benzyloxy)tetrahydro-2H-pyran (22, 1.12 g, 1.44 mmol) from Step 3 in dichloromethane (150 mL, 0.01M) under an atmosphere of nitrogen was added Grubbs $2^{nd}$ generation catalyst (100 mg, 0.16 mmol), and the mixture was heated at 60° C. overnight. After re-cooling to room temperature, the reaction mixture was filtered through a pad of Celite®, washed with ethyl acetate (100 mL) and the filtrate was evaporated under reduced pressure. The resulting crude residue was purified on a Biotage® purification apparatus (silica gel, 5 to 20% tetrahydrofuran in hexanes gradient) to yield the title compound (23, (4-form, 279 mg, 0.374 mmol, 26%) as a white solid.

$^1$H NMR (400 MHz, DMSO-d$_6$) δ 7.29-7.25 (m, 10H), 7.22-7.13 (m, 5H), 7.12-7.02 (m, 3H), 6.89 (s, 1H), 6.86-6.82 (m, 2H), 6.79-6.69 (m, 2H), 5.96-5.92 (m, 2H), 4.79-4 (d, J=5.6 Hz, 1H), 4.65 (d, J=6.0 Hz, 1H), 4.15 (d, J=10.0 Hz, 1H), 4.02.77 (m, 3H), 4.68-4.65 (m, 1H), 4.56-4.53 (m, 1H), 4.49-4.43 (m, 1H), 4.41-4.34 (m, 2H), 4.22-4.13 (m, 1H), 4.12-4.02 (m, 2H), 3.99-3.81 (m, 5H), 3.76-3.71 (m, 1H), 3.68-3.63 (m, 2H), 3.47-3.45 (m, 1H), 1.32 (t, J=6.8 Hz, 3H); MNa+ 769.

Step 3: (8R,9S,10R,11R,12S)-15-Chloro-14-(4-ethoxybenzyl)-2,3,4,5,7,8,9,10,11,12-decahydro-2H-8,12-epoxybenzo[g][1,6]dioxacyclotetradecine-9,10,11-triol (24)

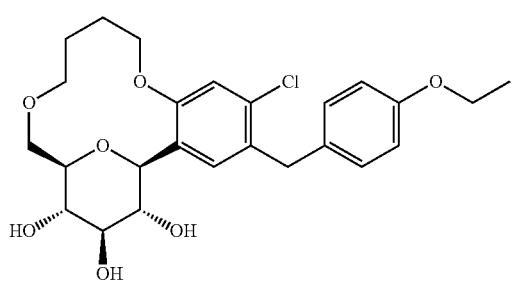

To a solution of (Z)-((8R,9S,10R,11R,12S)-9,10,11-Tris(benzyloxy)-15-chloro-14-(4-ethoxybenzyl)-2,3,4,5,7,8,9,10,11,12-decahydro-2H-8,12-epoxybenzo[g][1,6]dioxa-cyclotetradecine (23, 279 mg, 0.374 mmol) in methanol (3 mL)/tetrahydrofuran (3 mL) was added 10% palladium on charcoal (22 mg). The reaction mixture was stirred under hydrogen gas overnight. The reaction solution was filtered through syringe filter and the filtrate was evaporated under reduced pressure. The crude compound was diluted with methanol and purified by reverse phase preparative HPLC (Waters®, SunFire™ Prep, 5 to 50% acetonitrile in water gradient) to obtain the title compound (24, 38 mg, 0.08 mmol, 22%) as a white solid.

$^1$H NMR (400 MHz, DMSO-d$_6$) δ 7.27 (s, 1H), 7.09 (d, J=8.8 Hz, 1H), 7.05 (s, 1H), 6.82 (d, J=8.4 Hz, 1H), 5.01 (d, J=4.4 Hz, 1H), 4.96 (d, J=5.6 Hz, 1H), 4.65 (d, J=6.0 Hz, 1H), 4.15 (d, J=10.0 Hz, 1H), 4.02-3.94 (m, 2H), 3.96 (q, J=7.2 Hz, 2H), 3.89 (d, J=9.2 Hz, 1H), 3.67-3.59 (m, 2H), 3.54-3.50 (m, 1H), 3.38-3.36 (m, 1H), 3.29-3.23 (m, 1H), 3.15-3.14 (m, 1H), 1.77-1.58 (m, 4H), 1.29 (t, J=7.2 Hz, 3H); MH+-H2O 461, MH+-NH4+ 443, IR (neat, cm$^{-1}$) 3444, 3288, 2977, 2931, 1608, 1512, 1476, 1392, 1349, 1238, 1176, 1012, 959, 842.

INTERMEDIATE 6

(3-Iodopropoxy)triisopropylsilane (26)

Step 1: 3-(Triisopropylsilyloxy)propan-1-ol (25)

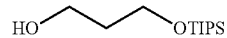

See INSTITUT PASTEUR KOREA, WO2010/46780 A2, 2010

To a solution of sodium hydride (60% dispersion in mineral oil, 2.68 g, 0.067 mol) in tetrahydrofuran (112 mL) at 0° C. under an atmosphere of nitrogen was added n-propandiol (5 g, 0.067 mol) in tetrahydrofuran (36 mL), and the mixture was stirred for 15 min at the same temperature, warmed up to room temperature and stirred for 30 min. After cooling to 0° C., chlorotriisopropylsilane (18.2 mL, 0.067 mol) was added dropwise to reaction mixture and the mixture was stirred with gradual warming to ambient temperature over 2 h. After re-cooling to 0° C., the reaction mixture was quenched by addition of water (30 mL) and the mixture was diluted with water, extracted with ethyl acetate. The organic layer was washed with brine, dried over magnesium sulfate, filtered and evaporated in vacuo. The resulting crude residue was purified on a Biotage® purification apparatus (silica gel, 2 to 15% tetrahydrofuran in hexanes gradient) to yield the title compound (25, 14.6 g, 0.063 mol, 94%) as colorless oil.

Step 2: (5-Iodopentyloxy)triisopropylsilane (26)

See Magnus, Philip; Matthews, Kenneth S.
Journal of the American Chemical Society, 2005, vol. 127, #36, p. 12476-12477

To a solution 3-(Triisopropylsilyloxy)propan-1-ol (25, 14.6 g, 0.063 mol) from Step 1 in pyridine (35 mL) was added tosylchloride (19.6 g, 0.10 mol) at 0° C. and the reaction mixture stirred at room temperature for 3 h. The solution was diluted with 5% HCl solution and extracted with diethyl ether, washed with aqueous sodium hydrogen chloride solution and brine prior to drying over magnesium chloride. After filtration and the removal of organic volatiles under reduced pressure, the residue was diluted with acetone and added with sodium iodide (60.9 g, 0.402 mol). The reaction mixture was stirred at room temperature for 3 h, diluted with diethyl ether, quenched with $H_2O$, extracted with ether. The organic layer was washed with aqueous sodium sulfite and brine and dried over magnesium sulfate, filtered and concentrated in vacuo. The crude residue was purified on Biotage® purification apparatus (silica gel, 0 to 5% ethyl acetate in hexanes) to yield the title compound (26, 18.7 g, 0.055 mol, 87%) as colorless oil.

EXAMPLE 3

(9R,10S,11R,12R,13S)-16-Chloro-15-(4-ethoxybenzyl)-3,4,5,6,8,9,10,11,12,13-decahydro-2H-9,13-epoxybenzo[h][1,7]dioxacyclopentadecine-10,11,12-triol (33)

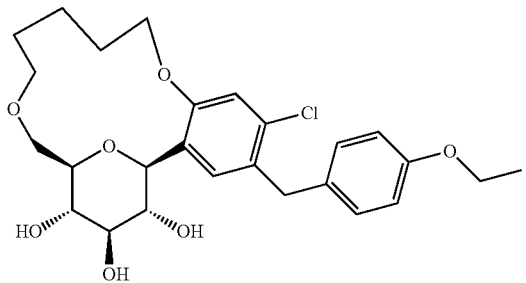 [SMILES: CCOc1ccc(Cc2cc3c(cc2Cl)OCCCCCOC[C@H]2O[C@@H]3[C@H](O)[C@@H](O)[C@@H]2O)cc1]

INTERMEDIATE 7

(5-Bromopentyloxy)(tert-butyl)diphenylsilane (27)

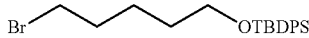

See Romeril, Stuart P.; Lee, Victor; Claridge, Timothy D. W.; Baldwin, Jack E. Tetrahedron Letters, 2002, vol. 43, #2, p. 327-330

To a solution of 5-bromopentan-1-ol (0.43 mL, 3.00 mmol) in tetrahydrofuran (15 mL) at 0° C. under an atmosphere of nitrogen were added imidazole (210 mg, 3.00 mmol) and t-Butylchlorodiphenylsilane (0.78 mL, 3.00 mmol) at 0° C. After 5 h at room temperature, the reaction mixture was quenched by addition of water (5 mL) and the mixture was extracted with diethyl ether. The organic layer was washed with brine, dried over magnesium sulfate, filtered and evaporated in vacuo. The resulting crude residue was purified on a Biotage® purification apparatus (silica gel, 0 to 10% ethyl acetate in hexanes gradient) to yield the title compound (19, 980 mg, 2.42 mmol, 81%) as colorless oil.

$^1$H NMR (400 MHz, CDCl$_3$) δ 7.72-7.69 (m, 4H), 7.48-7.39 (m, 6H), 3.70 (t, J=6.4 Hz, 1H), 3.42 (t, J=6.8 Hz, 1H), 1.91-1.84 (m, 2H), 1.62-1.58 (m, 2H), 1.47-1.42 (m, 4H), 1.09 (s, 9H).

INTERMEDIATE 8

(9R,10S,11R,12R,13S)-10,11,12-Tris(benzyloxy)-16-chloro-15-(4-ethoxybenz-yl)-3,4,5,6,8,9,10,11,12,13-decahydro-2H-9,13-epoxybenzo[h][1,7]dioxacyclopentadecine (32)

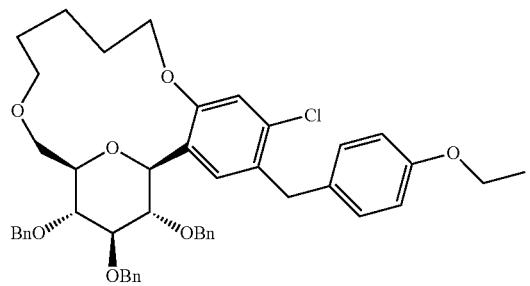

Step 1: (5-(((2R,3R,4R,5S,6S)-6-(2-(allyloxy)-4-chloro-5-(4-ethoxybenzyl)phenyl)-3,4,5-tris(benzyloxy)tetrahydro-2H-pyran-2-yl)methoxy)pentyloxy)(tert-butyl)diphenylsilane (28)

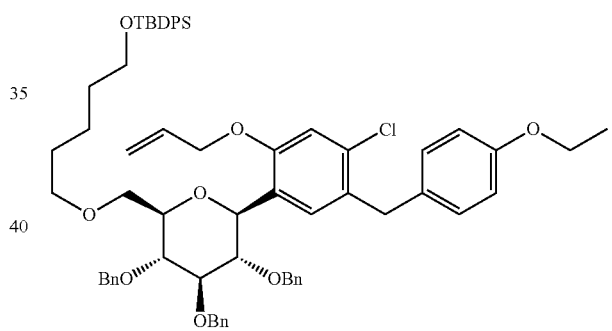

To a solution of ((2R,3R,4R,5S,6S)-6-(2-(allyloxy)-4-chloro-5-(4-ethoxybenzyl)phenyl)-3,4,5-tris(benzyloxy)tetrahydro-2H-pyran-2-yl)methanol (16, 1.1 g, 1.51 mmol) in N,N-dimethylformamide (25 mL) was added sodium hydride (60% dispersion in mineral oil, 120.4 mg, 3.01 mmol) at 0° C., and the reaction mixture was stirred at ambient temperature for 0.5 h. After 1 h at room temperature, the reaction mixture was re-cooled to 0° C. and (5-Bromopentyloxy)(tert-butyl)diphenylsilane (27, 980 mg, 2.42 mmol) was added dropwise, and the mixture was stirred with gradual warming to ambient temperature over 5 h. After re-cooling to 0° C., the reaction mixture was quenched by addition of water (25 mL). The mixture was diluted with water and extracted with ethyl acetate. The organic layer was washed with brine, dried over magnesium sulfate, filtered and evaporated in vacuo. The resulting crude residue was purified on a Biotage® purification apparatus (silica gel, 5 to 20% tetrahydrofuran in hexanes gradient) to yield the title compound (28, 664 mg, 0.63 mmol, 42%) as yellowish oil.

$^1$H NMR (400 MHz, CDCl$_3$) δ 7.69-7.67 (m, 4H), 7.45-7.40 (m, 6H), 7.35-7.32 (m, 10H), 7.26-7.14 (m, 6H), 7.06-7.02 (m, 1H), 6.92-6.86 (m, 3H), 6.77-6.75 (m, 1H), 6.04-

5.94 (m, 1H), 5.43-5.39 (m, 1H), 5.27-5.24 (m, 1H), 4.96-4.89 (m, 3H), 4.72 (d, J=11.2 Hz, 1H), 4.49-4.43 (m, 3H), 4.05-3.89 (m, 5H), 3.85-3.77 (m, 2H), 3.75-3.68 (m, 2H), 3.67-3.64 (m, 3H), 3.56-3.47 (m, 2H), 3.42-3.34 (m, 1H), 1.63-1.53 (m, 2H), 1.40 (t, J=6.8 Hz, 3H), 1.06 (s, 9H).

Step 2: 5-(((2R,3R,4R,5S,6S)-6-(2-(allyloxy)-4-chloro-5-(4-ethoxybenzyl)phenyl)-3,4,5-tris(benzyloxy)tetrahydro-2H-pyran-2-yl)methoxy)pentan-1-ol (29)

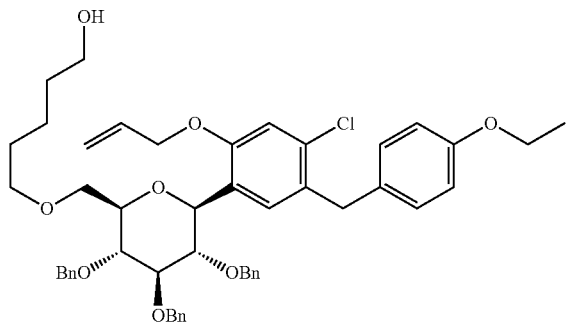 [SMILES: C=CCOc1cc(Cl)c(Cc2ccc(OCC)cc2)cc1[C@@H]1O[C@H](COCCCCCO)[C@@H](OCc2ccccc2)[C@H](OCc2ccccc2)[C@H]1OCc1ccccc1]

To a solution of (5-(((2R,3R,4R,5S,6S)-6-(2-(allyloxy)-4-chloro-5-(4-ethoxybenzyl)phenyl)-3,4,5-tris(benzyloxy)tetrahydro-2H-pyran-2-yl)methoxy)pentyloxy)(tert-butyl)diphenylsilane (28, 664 mg, 0.626 mmol) from Step 1 in tetrahydrofuran (8 mL) was added tetrabutylammonium fluoride (1.0 M in tetrahydrofuran, 1.9 mL, 1.88 mmol) and the reaction mixture was stirred at ambient temperature for 2 h. After removal of organic volatiles under reduced pressure, the residue was partitioned between ethyl acetate and saturated ammonium chloride solution. The organic layer was separated and the aqueous layer was extracted with ethyl acetate. The combined organic layers were washed with brine, dried over magnesium sulfate, filtered and concentrated in vacuo. The crude residue was purified on Biotage® purification apparatus (silica gel, 10 to 60% tetrahydrofuran in hexanes) to yield the title compound (29, 479 mg, 0.583 mmol, 93%) as colorless oil.

MNa+ 843.

Step 3: 5-chloro-4-(4-ethoxybenzyl)-2-((2S,3S,4R,5R,6R)-3,4,5-tris(benzyloxy)-6-((5-hydroxypentyloxy)methyl)tetrahydro-2H-pyran-2-yl)phenol (30)

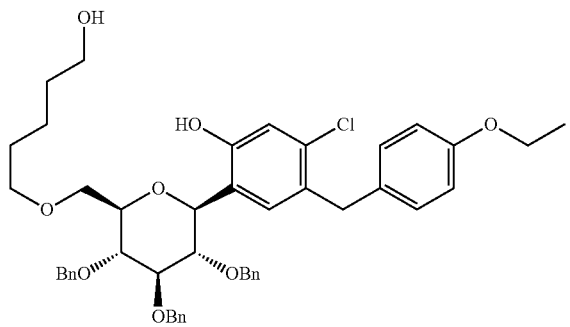 [SMILES: CCOc1ccc(Cc2cc([C@@H]3O[C@H](COCCCCCO)[C@@H](OCc4ccccc4)[C@H](OCc4ccccc4)[C@H]3OCc3ccccc3)c(O)cc2Cl)cc1]

To a solution of 5-(((2R,3R,4R,5S,6S)-6-(2-(allyloxy)-4-chloro-5-(4-ethoxybenzyl)phenyl)-3,4,5-tris(benzyloxy)tetrahydro-2H-pyran-2-yl)methoxy)pentan-1-ol (29, 479 mg, 0.584 mmol) from Step 2 in tetrahydrofuran (6 mL) were added sodium borohydride (177 mg, 4.668 mmol) and tetrakis(triphenylphosphine)palladium (67.5 mg, 0.058 mmol). The reaction mixture was stirred at room temperature overnight. The mixture was diluted with ethyl acetate and quenched with saturated ammonium chloride, extracted with ethyl acetate. The organic layer was washed with brine, dried over magnesium sulfate, filtered and evaporated in vacuo. Flash chromatography on a Biotage® apparatus (silica gel, 10 to 50% tetrahydrofuran in hexanes gradient) gave the title compound (30, 459 mg, 0.58 mmol, 100%) as colorless oil.

¹H NMR (400 MHz, DMSO-d₆) δ 9.84 (s, 1H), 7.38-7.27 (m, 10H), 7.23-7.10 (m, 5H), 7.07-7.02 (m, 2H), 6.93-6.86 (m, 3H), 6.76-6.74 (m, 1H), 4.81-4.78 (m, 3H), 4.65-4.60 (m, 2H), 4.42-4.37 (m, 1H), 4.00-3.85 (m, 4H), 3.76-3.67 (m, 2H), 3.65-3.51 (m, 4H), 3.47-3.40 (m, 1H), 3.35-3.28 (m, 2H), 3.25-3.20 (m, 2H), 1.53-1.33 (m, 4H), 1.36-1.21 (m, 2H), 1.29 (t, J=6.8 Hz, 3H); MNa⁺ 803.

Step 4: 5-Chloro-4-(4-ethoxybenzyl)-2-((2S,3S,4R,5R,6R)-3,4,5-tris(benzyloxy)-6-((5-iodopentyloxy)methyl)tetrahydro-2H-pyran-2-yl)phenol (31)

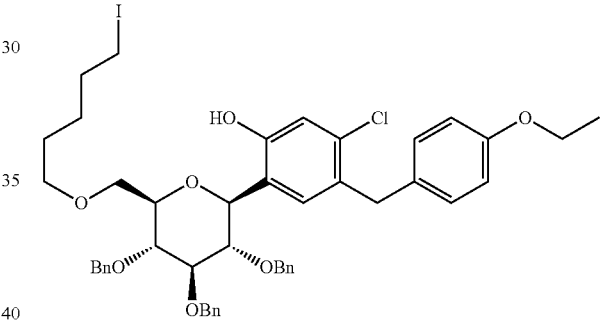

To a solution of 5-chloro-4-(4-ethoxybenzyl)-2-((2S,3S,4R,5R,6R)-3,4,5-tris(benzyloxy)-6-((5-hydroxypentyloxy)methyl)tetrahydro-2H-pyran-2-yl)phenol (30, 459 mg, 0.58 mmol) in benzene (3 mL) under an atmosphere of nitrogen were added imidazole (448 mg, 1.76 mmol) and triphenylphosphine (467 mg, 1.76 mmol). After 5 min, iodine (448 mg, 1.76 mmol) in benzene (2 mL) was added dropwide to the reaction mixture at room temperature. The reaction solution was stirred for 1 h, diluted with diethyl ether, quenched with saturated sodium hydrogen carbonate, extracted with diethyl ether (2×). The organic layer was washed with brine, dried over magnesium sulfate, filtered and evaporated in vacuo. The resulting crude residue was purified on a Biotage® purification apparatus (silica gel, 5 to 25% tetrahydrofuran in hexanes gradient) to yield the title compound (31, 485 mg, 0.54 mmol, 93%) as yellow foam.

¹H NMR (400 MHz, DMSO-d₆) δ 9.83 (s, 1H), 7.38-7.28 (m, 10H), 7.24-7.10 (m, 5H), 7.06-7.04 (m, 2H), 6.92-6.86 (m, 3H), 6.76-6.74 (m, 1H), 4.82-4.79 (m, 3H), 4.66-4.60 (m, 2H), 4.42-4.35 (m, 1H), 4.00-3.85 (m, 4H), 3.76-3.67 (m, 2H), 3.65-3.51 (m, 4H), 3.47-3.40 (m, 1H), 3.35-3.28 (m, 2H), 3.25-3.20 (m, 2H), 1.80-1.70 (m, 2H), 1.53-1.43 (m, 2H), 1.41-1.32 (m, 2H), 1.28 (t, J=6.8 Hz, 3H); MNa⁺ 913.

Step 5: (9R,10S,11R,12R,13S)-10,11,12-Tris(benzyloxy)-16-chloro-15-(4-ethoxybenz-yl)-2,3,4,5,6,8,9,10,11,12,13-undecahydro-2H-9,13-epoxybenzo[h]-[1,7]dioxacyclo-pentadecine (32)

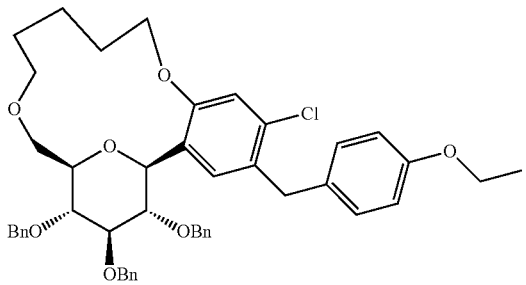

To a solution of 5-chloro-4-(4-ethoxybenzyl)-2-((2S,3S,4R,5R,6R)-3,4,5-tris(benzyloxy)-6-((5-iodopentyloxy)methyl)tetrahydro-2H-pyran-2-yl)phenol (31, 480 mg, 0.54 mmol) from Step 4 in toluene (54 mL) were added potassium carbonate (15 mg, 1.08 mmol) and 18-crown-6 (288 mg, 1.08 mmol). The resulting mixture was stirred at room temperature overnight and quenched with H$_2$O. After dilution with ethyl acetate, the organic layer was washed with water and brine prior to drying over magnesium sulfate. After filtration and removal of volatiles under reduced pressure, flash chromatography on a Biotage® apparatus (silica gel, 10 to 50% tetrahydrofuran in hexanes gradient) was performed to provide the macrocyclic compound (32, 261 mg, 0.34 mmol, 64%) as a white solid.

$^1$H NMR (400 MHz, DMSO-d$_6$) δ 7.36-7.27 (m, 10H), 7.26-7.12 (m, 7H), 7.10-7.07 (m, 1H), 6.89-6.82 (m, 2H), 6.78-6.71 (m, 1H), 4.81-4.77 (m, 3H), 4.67 (d, J=10.8 Hz, 1H), 4.48-4.43 (m, 1H), 4.26-4.23 (m, 2H), 4.10-4.01 (m, 2H), 3.98-3.88 (m, 6H), 3.80-3.60 (m, 4H), 3.48-3.41 (m, 3H), 1.95-1.86 (m, 2H), 1.64-1.61 (m, 2H), 1.31 (t, J=6.8 Hz, 3H); MNa$^+$ 785.

Step 6: (9R,10S,11R,12R,13S)-16-Chloro-15-(4-ethoxybenzyl)-2,3,4,5,6,8,9,10,11,12,13-undecahydro-2H-9,13-epoxybenzo[h][1,7]dioxacyclopentadecine-10,11,12-triol (33)

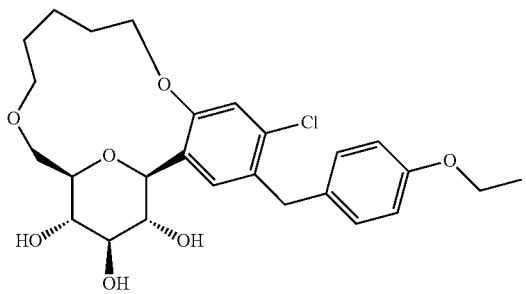 [SMILES: CCOc1ccc(Cc2cc3c(cc2Cl)OCCCCCOC[C@H]2O[C@@H]3[C@H](O)[C@@H](O)[C@@H]2O)cc1]

To a solution of (2S,3R,4R,5S,6R)-2-(4-Chloro-3-((5-(pyrazin-2-yl)-1,3,4-thiadiazol-2-yl)methyl)phenyl)-6-(hydroxymethyl)-tetrahydro-2H-pyran-3,4,5-triol (24, 261 mg, 0.34 mmol) in dichloromethane (12 mL) at 0° C. was added boron trichloride (1.0 M in dichloromethane, 1.8 mL, 5.3 mmol). The reaction mixture was stirred at 0° C. for 0.5 h and quenched with methanol (3 mL), then the solution was concentrated in vacuo. Purification by reverse phase preparative HPLC (Waters®, SunFire™ Prep, 5 to 50% acetonitrile in water gradient) provided the title compound (25, 33 mg, 0.067 mmol, 20%) as a white solid.

$^1$H NMR (400 MHz, DMSO-d$_6$) δ 7.26 (s, 1H), 7.11 (d, J=8.4 Hz, 2H), 7.08 (s, 1H), 6.84 (d, J=8.8 Hz, 2H), 5.08 (m, 1H), 5.01 (m, 1H), 4.83-4.82 (m, 1H), 4.21 (d, J=10.0 Hz, 1H), 4.04 (m, 2H), 3.98 (q, J=7.2 Hz, 2H), 3.91 (d, J=12.4 Hz, 2H), 3.71-3.67 (m, 1H), 3.59 (d, J=11.6 Hz, 1H), 3.48-3.39 (m, 4H), 3.31-3.26 (m, 2H), 3.16-3.3.14 (m, 1H), 1.70-1.68 (m, 3H), 1.54-1.42 (m, 3H), 1.31 (t, J=6.8 Hz, 3H); M$^+$-H$_2$O 475, M$^+$-NH$_4^+$ 457.

EXAMPLE 4

(6R,7S,8R,9R,10S)-13-Chloro-12-(4-ethoxybenzyl)-2,3,5,6,7,8,9,10-octahydro-6,10-epoxybenzo[e][1,4]dioxacyclododecine-7,8,9-triol (34)

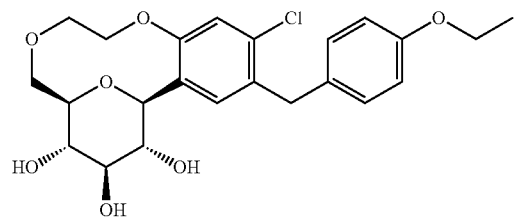 [SMILES: CCOc1ccc(Cc2cc3c(cc2Cl)OCCOC[C@H]2O[C@@H]3[C@H](O)[C@@H](O)[C@@H]2O)cc1]

$^1$H NMR (400 MHz, DMSO-d$_6$) δ 7.12 (s, 1H), 7.05 (d, J=8.4 Hz, 2H), 6.80 (d, J=8.4 Hz, 2H), 6.52 (s, 1H), 4.97 (br, 2H), 4.41 (d, J=9.2 Hz, 1H), 3.97 (q, J=6.8 Hz, 2H), 3.81 (d, J=3.6 Hz, 2H), 3.69 (d, J=10.8 Hz, 1H), 3.48-3.25 (m, 8H), 3.18-3.12 (m, 3H), 1.31 (t, J=7.2 Hz, 3H); MH$^+$-4H$^+$ 447.

EXAMPLE 5

(7R,8S,9R,10R,11S)-14-Chloro-13-(4-ethoxybenzyl)-3,4,6,7,8,9,10,11-octahydro-2H-7,11-epoxybenzo[f][1,5]dioxacyclotridecine-8,9,10-triol (35)

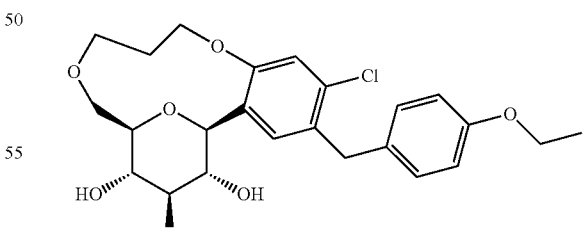

$^1$H NMR (400 MHz, DMSO-d$_6$) δ 7.47 (s, 1H), 7.27 (s, 1H), 7.11 (d, J=8.8 Hz, 1H), 6.84 (d, J=8.8 Hz, 1H), 5.33-4.79 (br, 2H), 4.25 (d, J=10.0 Hz, 1H), 4.18-4.14 (m, 1H), 4.01-3.95 (m, 3H), 3.91-3.80 (m, 3H), 3.74-3.67 (m, 2H), 3.61 (t, J=9.6 Hz, 1H), 3.46-3.40 (m, 2H), 3.38-3.34 (m, 3H), 3.15-3.11 (m, 1H), 1.93-1.84 (m, 1H), 1.79-1.73 (m, 1H), 1.31 (t, J=6.8 Hz, 3H); MH+-H2O 447.

EXAMPLE 6

(10R,11S,12R,13R,14S)-17-Chloro-16-(4-ethoxybenzyl)-2,3,4,5,6,7,9,10,11,12,13,14-dodecahydro-10,14-epoxybenzo[i][1,8]dioxacyclohexadecine-11,12,13-triol (36)

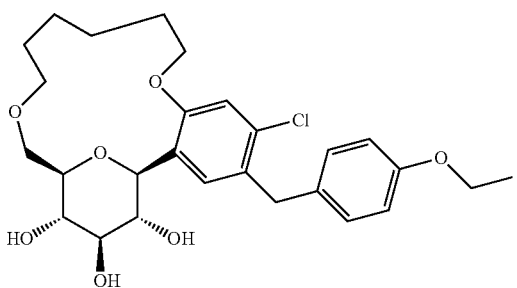 [SMILES: CCOc1ccc(Cc2cc3c(cc2Cl)OCCCCCCOC[C@H]2O[C@@H]3[C@H](O)[C@@H](O)[C@@H]2O)cc1]

$^1$H NMR (400 MHz, DMSO-d$_6$) δ 7.29 (s, 1H), 7.10 (d, J=8.8 Hz, 2H), 7.03 (s, 1H), 6.83 (d, J=8.8 Hz, 2H), 5.11 (br, 1H), 5.02 (br, 1H), 4.83 (br, 1H), 4.39 (d, J=10.0 Hz, 1H), 4.15-4.13 (m, 1H), 4.01-3.96 (m, 3H), 3.89-3.86 (m, 2H), 3.66 (t, J=9.2 Hz, 1H), 3.53 (d, J=12.0 Hz, 1H), 3.46 (t, J=8.0 Hz, 2H), 3.38-3.30 (m, 2H), 2.99-2.97 (m, 1H), 1.82 (m, 1H), 1.68-1.66 (m, 2H), 1.54-1.39 (m, 5H), 1.31 (t, J=6.8 Hz, 3H); MNa+ 529, MH+-H$_2$O 489, MH+-NH4+ 471, IR (neat, cm$^{-1}$) 3429, 2917, 1608, 1509, 1242, 1077, 1040, 989, 833.

EXAMPLE 7

(7R,8S,9R,10R,11S)-14-Chloro-13-(4-ethylbenzyl)-3,4,6,7,8,9,10,11-octahydro-2H-7,11-epoxybenzo[f][1,5]dioxacyclotridecine-8,9,10-triol (37)

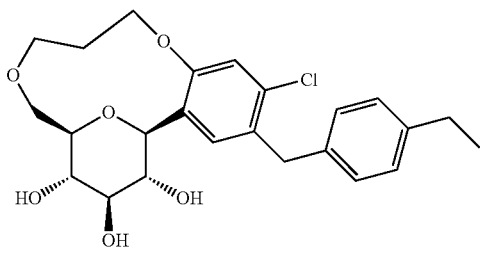 [SMILES: CCc1ccc(Cc2cc3c(cc2Cl)OCCCOC[C@H]2O[C@@H]3[C@H](O)[C@@H](O)[C@@H]2O)cc1]

$^1$H NMR (400 MHz, DMSO-d$_6$) δ 7.50 (s, 1H), 7.29 (s, 1H), 7.12 (s, 4H), 5.17-5.14 (m, 2H), 5.03 (d, J=5.6 Hz, 1H), 4.25 (d, J=10.0 Hz, 1H), 4.17-4.15 (m, 1H), 4.01 (d, J=14.8 Hz, 1H), 3.92 (d, J=14.4 Hz, 1H), 3.90-3.80 (m, 2H), 3.74-3.68 (m, 2H), 3.64-3.58 (m, 1H), 3.46-3.38 (m, 2H), 3.15-3.09 (m, 1H), 2.55 (q, J=7.6 Hz, 2H), 1.90-1.84 (m, 1H), 1.78-1.72 (m, 1H), 1.16 (t, J=7.6 Hz, 3H); MH+-H$_2$O 431, IR (neat, cm$^{-1}$) 3374, 2962, 2927, 2872, 1607, 1488, 1381, 1251, 1087, 1039, 987, 846.

EXAMPLE 8

(8R,9S,10R,11R,12S)-15-Chloro-14-(4-ethylbenzyl)-2,3,4,5,7,8,9,10,11,12-decahydro-8,12-epoxybenzo[g][1,6]dioxacyclotetradecine-9,10,11-triol (38)

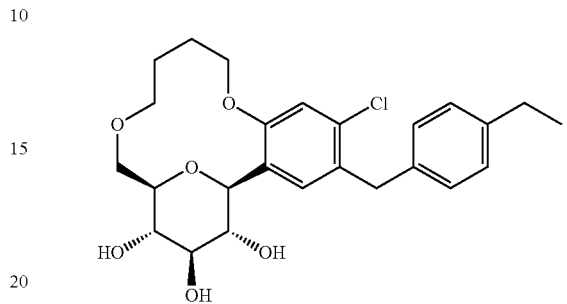

$^1$H NMR (400 MHz, DMSO-d$_6$) δ 7.32 (s, 1H), 7.13 (s, 4H), 7.07 (s, 1H), 5.05 (d, J=4.8 Hz, 1H), 5.00 (d, J=5.2 Hz, 1H), 4.92 (d, J=6.4 Hz, 1H), 4.17 (d, J=10.0 Hz, 1H), 3.98 (d, J=14.8 Hz, 1H), 3.91 (d, J=14.8 Hz, 1H), 3.71-3.61 (m, 3H), 3.56-3.52 (m, 1H), 3.40-3.37 (m, 4H), 3.31-3.25 (m, 1H), 3.19-3.15 (m, 1H), 2.56 (q, J=7.6 Hz, 2H), 1.79 (m, 2H), 1.73-1.69 (m, 1H), 1.61-1.60 (m, 1H), 1.16 (t, J=7.6 Hz, 1H); MNa+ 485, MH+-H$_2$O 445, MH+-NH$_4$+ 427, IR (neat, cm$^{-1}$) 3375, 2964, 2860, 1616, 1495, 1329, 1253, 1086, 1048, 983, 832.

EXAMPLE 9

(9R,10S,11R,12R,13S)-16-Chloro-15-(4-ethylbenzyl)-3,4,5,6,8,9,10,11,12,13-decahydro-2H-9,13-epoxybenzo[h][1,7]dioxacyclopentadecine-10,11,12-triol (39)

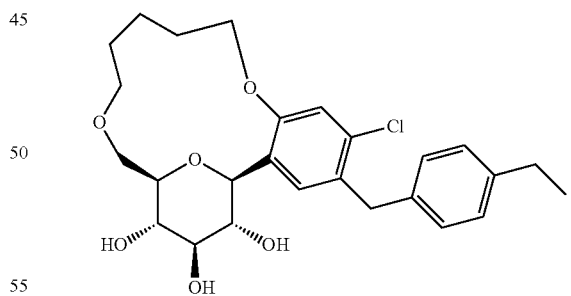

$^1$H NMR (400 MHz, DMSO-d$_6$) δ 7.29 (s, 1H), 7.13 (s, 4H), 7.09 (s, 1H), 5.06 (br, 1H), 5.00 (br, 1H), 4.84 (br, 1H), 4.21 (d, J=10.0 Hz, 1H), 4.04 (m, 2H), 4.99 (d, J=14.8 Hz, 1H), 3.91 (d, J=14.8 Hz, 1H), 3.72-3.68 (m, 1H), 3.60 (d, J=12.0 Hz, 1H), 3.46-3.39 (m, 4H), 3.30-3.26 (m, 1H), 3.16-3.14 (m, 1H), 2.56 (q, J=7.6 Hz, 1H), 1.68 (m, 3H), 1.50-1.42 (m, 3H), 1.16 (t, J=7.6 Hz, 1H); MNa+ 499, MH+-H$_2$O 459, MH+-NH$_4$+ 441, IR (neat, cm$^{-1}$) 3358, 2918, 1608, 1568, 1493, 1466, 1257, 1212, 1062, 991, 915, 829.

EXAMPLE 10

(10R,11S,12R,13R,14S)-17-Chloro-16-(4-ethylbenzyl)-2,3,4,5,6,7,9,10,11,12,13,14-dodecahydro-10,14-epoxybenzo[i][1,8]dioxacyclohexadecine-11,12,13-triol (40)

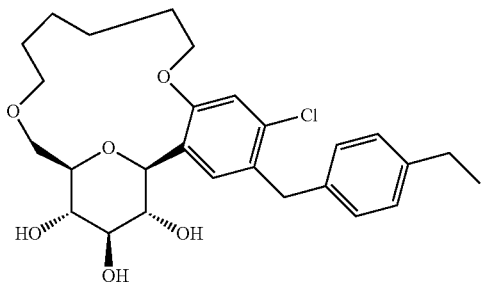 [SMILES: CCc1ccc(Cc2cc3c(cc2Cl)OCCCCCCOC[C@H]2O[C@@H]3[C@H](O)[C@@H](O)[C@@H]2O)cc1]

$^1$H NMR (400 MHz, DMSO-d$_6$) δ 7.31 (s, 1H), 7.12 (s, 4H), 7.03 (s, 1H), 5.08 (d, J=4.4 Hz, 1H), 5.01 (d, J=4.4 Hz, 1H), 4.82 (d, J=5.2 Hz, 1H), 4.39 (d, J=10.0 Hz, 1H), 4.16-4.13 (m, 1H), 4.01 (d, J=14.8 Hz, 1H), 3.93-3.86 (m, 2H), 3.70-3.65 (m, 1H), 3.53 (d, J=12.0 Hz, 1H), 3.48-3.44 (m, 2H), 3.38-3.29 (m, 2H), 2.97 (m, 1H), 2.56 (q, J=7.2 Hz, 1H), 1.82 (m, 1H), 1.68-1.66 (m, 2H), 1.54-1.49 (m, 1H), 1.46-1.39 (m, 4H), 1.16 (t, J=7.6 Hz, 1H); MNa+ 513, MH+-H$_2$O 473, MH+-NH$_4$+ 455; IR (neat, cm$^{-1}$) 3396, 2917, 1610, 1497, 1323, 1255, 1134, 1059, 1003, 944, 827.

EXAMPLE 11

(8R,9S,10R,11R,12S)-15-Chloro-14-(4-(methylthio)benzyl)-2,3,4,5,7,8,9,10,11,12-decahydro-8,12-epoxybenzo[g][1,6]dioxacyclotetradecine-9,10,11-triol (41)

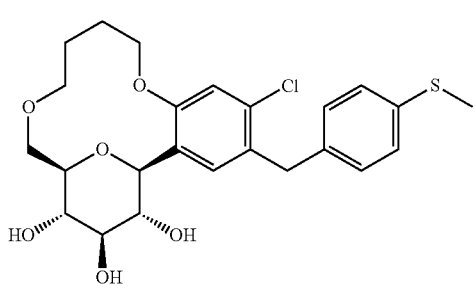 [SMILES: CSc1ccc(Cc2cc3c(cc2Cl)OCCCCOC[C@H]2O[C@@H]3[C@H](O)[C@@H](O)[C@@H]2O)cc1]

$^1$H NMR (400 MHz, DMSO-d$_6$) δ 7.30 (s, 1H), 7.23-7.09 (m, 4H), 7.06 (s, 1H), 5.07-4.89 (m, 3H), 4.15 (d, J=9.8 Hz, 1H), 4.05-3.93 (m, 4H), 3.74-3.58 (m, 3H), 3.56-3.61 (m, 1H), 3.41-3.31 (m, 2H), 3.29-3.21 (m, 1H), 3.19-3.09 (m, 1H), 2.42 (s, 3H), 1.85-1.55 (m, 4H); M+Na+ 503; IR (neat, cm$^{-1}$) 3387, 2917, 1492, 1254, 1081, 1052, 1002, 914, 834.

EXAMPLE 12

(9R,10S,11R,12R,13S)-16-Chloro-15-(4-(methylthio)benzyl)-3,4,5,6,8,9,10,11,12,13-decahydro-2H-9,13-epoxybenzo[h][1,7]dioxacyclopentadecine-10,11,12-triol (42)

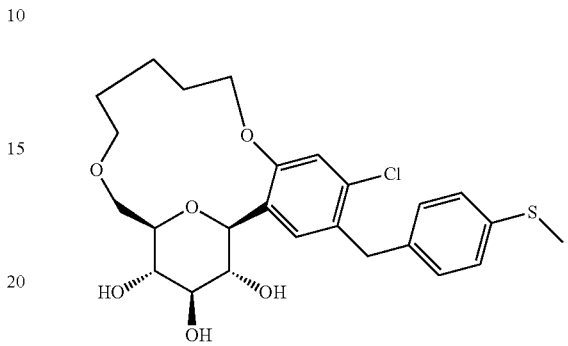

$^1$H NMR (400 MHz, DMSO-d$_6$) δ 7.27 (s, 1H), 7.21-7.10 (m, 4H), 7.07 (s, 1H), 5.05 (d, J=4.4 Hz, 1H), 4.99 (d, J=5.3 Hz, 1H), 4.81 (d, J=5.8 Hz, 1H), 4.19 (d, J=10.0 Hz, 1H), 4.06-3.88 (m, 4H), 3.71-3.62 (m, 1H), 3.58 (d, J=11.6 Hz, 1H), 3.52-3.37 (m, 4H), 3.27-3.21 (m, 1H), 3.18-3.08 (m, 1H), 1.77-1.58 (m, 3H), 1.56-1.39 (m, 3H); M+Na+ 517; IR (neat, cm$^{-1}$) 3378, 2918, 1609, 1492, 1255, 1034, 997, 833, 774.

EXAMPLE 13

(8R,9S,10R,11R,12S)-15-Chloro-14-((2,3-dihydrobenzo[b][1,4]dioxin-6-yl)-methyl)-2,3,4,5,7,8,9,10,11,12-decahydro-8,12-epoxybenzo[g][1,6]dioxacyclotetradecine-9,10,11-triol (43)

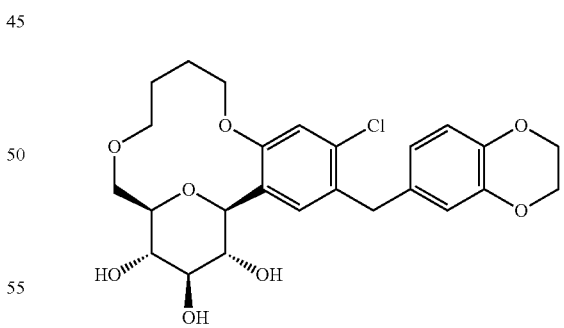

$^1$H NMR (400 MHz, DMSO-d$_6$) δ 7.28 (s, 1H), 7.05 (s, 1H), 6.77-6.71 (m, 1H), 6.69-6.62 (m, 2H), 5.04 (d, J=4.0 Hz, 1H), 4.99 (d, J=4.4 Hz, 1H), 4.91 (d, J=5.4 Hz, 1H), 4.22-4.11 (m, 5H), 4.09-3.96 (m, 2H), 3.84 (quartet, J=14.8 Hz, 2H), 3.70-3.58 (m, 3H), 3.57-3.44 (m, 1H), 3.39-3.32 (m, 2H), 3.29-3.22 (m, 1H), 3.17-3.09 (m, 1H), 1.85-1.52 (m, 4H); M+Na+ 515; IR (neat, cm$^{-1}$) 3380, 2917, 1506, 1463, 1284, 1255, 1122, 1087, 1067, 1045, 1000, 982, 952, 919, 885.

EXAMPLE 14

(9R,10S,11R,12R,13S)-16-Chloro-15-((2,3-dihydrobenzo[b][1,4]dioxin-6-yl)-methyl)-3,4,5,6,8,9,10,11,12,13-decahydro-2H-9,13-epoxybenzo[h][1,7]dioxacyclopentadecine-10,11,12-triol (44)

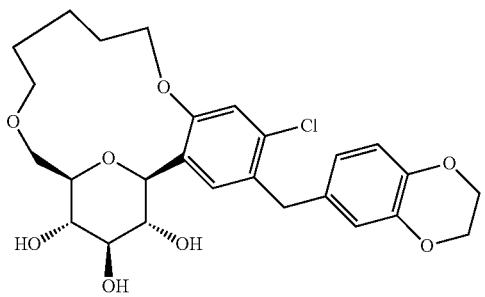 [SMILES: O[C@@H]1[C@@H](O)[C@H]2O[C@H](COCCCCCOc3cc(Cl)c(Cc4ccc5c(c4)OCCO5)cc32)[C@H]1O]

$^1$H NMR (400 MHz, DMSO-d$_6$) δ 7.25 (s, 1H), 7.06 (s, 1H), 6.77-6.71 (m, 1H), 6.68-6.63 (m, 2H), 5.05 (d, J=4.4 Hz, 1H), 5.00 (d, J=5.5 Hz, 1H), 4.82 (d, J=6.1 Hz, 1H), 4.23-4.16 (m, 5H), 4.08-3.97 (m, 2H), 3.84 (quartet, J=14.8 Hz, 2H), 3.71-3.63 (m, 1H), 3.58 (d, J=11.9 Hz, 1H), 3.51-3.37 (m, 4H), 3.32-3.23 (m, 1H), 3.18-3.09 (m, 1H), 1.78-1.59 (m, 3H), 1.57-1.38 (m, 3H); M+Na$^+$ 529; IR (neat, cm$^{-1}$) 3375, 2912, 1591, 1507, 1495, 1285, 1256, 1126, 1069, 1034, 1003, 920, 882.

EXAMPLE 15

(4R,5S,6R,7R,8S)-11-Chloro-10-(4-ethoxybenzyl)-(1aR,14aS)-1a,2,4,5,6,7,8,9,10-octahydro-1H-4,8-epoxybenzo[g]cyclopropa[c][1,6]dioxacyclotetradecine-5,6,7-triol (51)

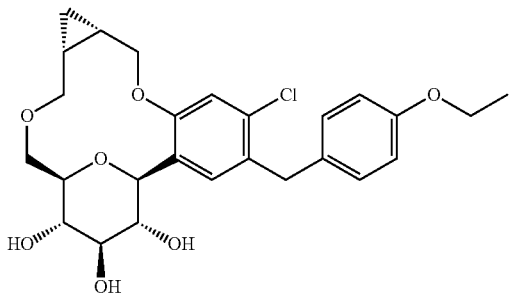 [SMILES: CCOc1ccc(Cc2cc3c(cc2Cl)OC[C@H]2C[C@H]2COC[C@H]2O[C@@H]3[C@H](O)[C@@H](O)[C@@H]2O)cc1]

Step 1: ((2R,3R,4R,5S,6S)-3,4,5-tris(benzyloxy)-6-(4-chloro-5-(4-ethoxybenzyl)-2-hydroxyphenyl)tetrahydro-2H-pyran-2-yl)methyl acetate (45)

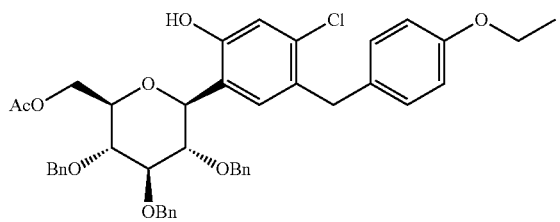 [SMILES: CCOc1ccc(Cc2cc([C@@H]3O[C@H](COC(C)=O)[C@@H](OCc4ccccc4)[C@H](OCc4ccccc4)[C@H]3OCc3ccccc3)c(O)cc2Cl)cc1]

To a solution of ((2R,3R,4R,5S,6S)-6-(2-(allyloxy)-4-chloro-5-(4-ethoxybenzyl)phenyl)-3,4,5-tris(benzyloxy)tetrahydro-2H-pyran-2-yl)methyl acetate (20, 2.51 g, 3.23 mmol) in tetrahydrofuran (40 mL) were added sodium borohydride (984 mg, 0.026 mol) and tetrakis(triphenylphosphine)palladium (373 mg, 0.323 mmol). The reaction mixture was stirred at room temperature for 5 h. The mixture was diluted with ethyl acetate and quenched with saturated sodium hydrogen carbonate, extracted with ethyl acetate. The organic layer was washed with brine, dried over magnesium sulfate, filtered and evaporated in vacuo. Flash chromatography on a Biotage® apparatus (silica gel, 10 to 35% tetrahydrofuran in hexanes gradient) gave the title compound (45, 2.19 g, 2.97 mmol, 92%) as colorless oil.

$^1$H NMR (400 MHz, DMSO-d$_6$) δ 9.89 (s, 1H), 7.38-7.28 (m, 10H), 7.23-7.12 (m, 5H), 7.07-7.05 (m, 1H), 6.92-6.88 (m, 4H), 6.77-6.74 (m, 1H), 4.86-4.79 (m, 3H), 4.67-4.59 (m, 2H), 4.41-4.35 (m, 1H), 4.30-4.27 (m, 1H), 4.10-4.05 (m, 1H), 3.98-3.85 (m, 5H), 3.82-3.75 (m, 2H), 3.74-3.66 (m, 1H), 3.57-3.49 (m, 1H), 2.00 (s, 3H), 1.31-1.23 (m, 3H); MNa+ 759.

Step 2: ((2R,3R,4R,5S,6S)-3,4,5-tris(benzyloxy)-6-(4-chloro-5-(4-ethoxybenzyl)-2-((Z)-4-hydroxybut-2-enyloxy)phenyl)tetrahydro-2H-pyran-2-yl)methyl acetate (46)

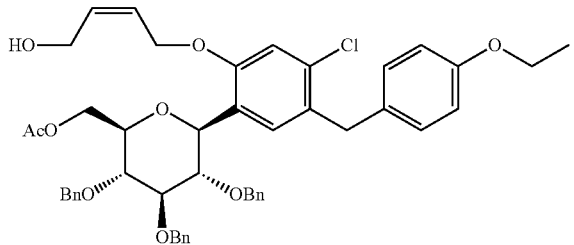 [SMILES: CCOc1ccc(Cc2cc([C@@H]3O[C@H](COC(C)=O)[C@@H](OCc4ccccc4)[C@H](OCc4ccccc4)[C@H]3OCc3ccccc3)c(OC/C=C\CO)cc2Cl)cc1]

To a solution of ((2R,3R,4R,5S,6S)-3,4,5-tris(benzyloxy)-6-(4-chloro-5-(4-ethoxybenzyl)-2-hydroxyphenyl)tetrahydro-2H-pyran-2-yl)methyl acetate (45, 2.19 g, 2.97 mmol) from Step 1 in tetrahydrofuran (30 mL) were added triphenylphosphine (1.57 g, 5.94 mmol) and cis-2-butene-1,4-diol (0.5 mL, 5.94 mmol) at 0° C., and diisopropyl azodicarboxylate (1.35 mL, 6.53 mmol) was added dropwise thereto. The reaction mixture was stirred at ambient temperature for 0.5 h and warmed up to room temperature for 4 h. After cooling to 0° C., the reaction mixture was quenched with H$_2$O, extracted with ethyl acetate and dried over magnesium sulfate. The crude residue was purified on Biotage® purification apparatus (silica gel, 10 to 45% tetrahydrofuran in hexanes) to yield the title compound (46, 2.08 g, 2.57 mmol, 87%) as colorless oil.

$^1$H NMR (400 MHz, DMSO-d$_6$) δ 7.36-7.28 (m, 11H), 7.23-7.13 (m, 5H), 7.10-7.07 (m, 2H), 6.87-6.81 (m, 2H), 6.78-6.76 (m, 1H), 5.74-5.68 (m, 1H), 5.61-5.56 (m, 1H), 4.84-4.81 (m, 4H), 4.64-4.59 (m, 4H), 4.44-4.37 (m, 1H), 4.29-4.26 (m, 1H), 4.11-4.05 (m, 3H), 3.96-3.90 (m, 5H), 3.83-3.76 (m, 1H), 3.72-3.67 (m, 1H), 3.57-3.53 (m, 1H), 2.00 (s, 3H), 1.31-1.24 (m, 3H); MNa+ 829.

Step 3: ((2R,3R,4R,5S,6S)-3,4,5-tris(benzyloxy)-6-(4-chloro-5-(4-ethoxybenzyl)-2-((2-(hydroxymethyl)cyclopropyl)methoxy)phenyl)tetrahydro-2H-pyran-2-yl)methyl acetate (47)

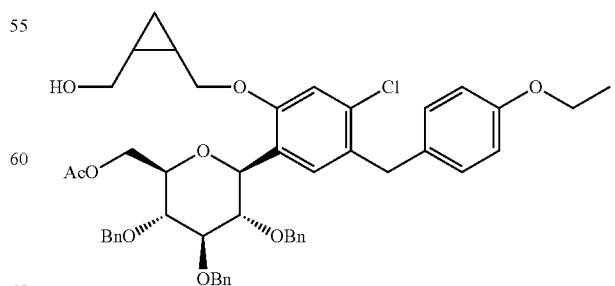

To a solution of diiodomethane (0.66 mL, 8.09 mmol) in dichloromethane (10 mL) was added diethyl zinc (1.1M solution in toluene, 3.7 mL, 4.05 mmol) at 0° C. and stirred for 15 min. The reaction mixture was cooled to −78° C. and ((2R,3R,4R,5S,6S)-3,4,5-tris(benzyloxy)-6-(4-chloro-5-(4-ethoxybenzyl)-2-((Z)-4-hydroxybut-2-enyloxy)phenyl)tetrahydro-2H-pyran-2-yl)methyl acetate (46, 0.82 mg, 1.01 mmol) in dichloromethane (5 mL) was added dropwise to the reaction mixture, slowly warmed up to −20° C. for 3 h. The reaction mixture was quenched with saturated ammonium chloride, extracted with ethyl acetate, and dried over magnesium sulfate. The organic layer was filtered and evaporated in vacuo and the residue was purified on a Biotage® apparatus (silica gel, 5 to 40% ethyl tetrahydrofuran in hexanes gradient) to give the title compound (47, 835 mg, 1.01 mmol, 100%, diastereomer in about 1:2 ratio) as colorless oil.

$^1$H NMR (400 MHz, CDCl$_3$) δ 7.38-7.31 (m, 10H), 7.27-7.13 (m, 6H), 7.10-7.08 (m, 1H), 6.86-6.77 (m, 4H), 5.05-4.92 (m, 4H), 4.67-4.64 (m, 1H), 4.54-4.52 (m, 1H), 4.42-4.39 (m, 1H), 4.33-4.24 (m, 2H), 4.05-3.96 (m, 4H), 3.95-3.82 (m, 3H), 3.73-3.67 (m, 2H), 3.65-3.52 (m, 2H), 3.36-3.34 (m, 1H), 3.00 (m, 1H), 2.80-2.60 (m, 1H), 2.04 (s, 3H), 1.42 (t, J=6.8 Hz, 3H), 0.87-0.82 (m, 1H), 0.13-0.09 (m, 1H); MNa+ 843. $^1$H NMR (400 MHz, CDCl$_3$) δ 7.36-7.32 (m, 10H), 7.23-7.16 (m, 6H), 7.09-7.07 (m, 1H), 6.97-6.95 (m, 1H), 6.89-6.87 (m, 2H), 6.80-6.78 (m, 1H), 5.00-4.91 (m, 4H), 4.65-4.63 (m, 1H), 4.53-4.50 (m, 1H), 4.39-4.31 (m, 2H), 4.28-4.24 (m, 1H), 4.05-3.96 (m, 5H), 3.94-3.85 (m, 4H), 3.72-3.58 (m, 4H), 3.37-3.31 (m, 1H), 2.03 (s, 3H), 1.41 (t, J=6.8 Hz, 3H), 0.92-0.83 (m, 1H), 0.28-0.24 (m, 1H); MNa+ 843.

Step 4: ((2R,3R,4R,5S,6S)-3,4,5-tris(benzyloxy)-6-(4-chloro-5-(4-ethoxybenzyl)-2-(((1S,2R)-2-(iodomethyl)cyclopropyl)methoxy)phenyl)tetrahydro-2H-pyran-2-yl)methyl acetate (48)

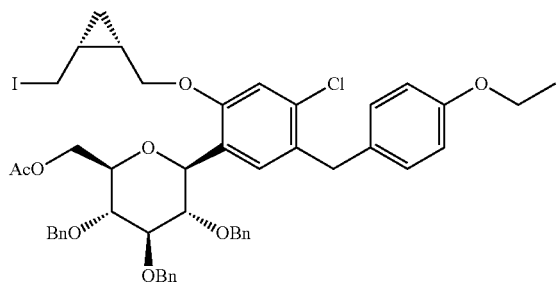 [SMILES: CCOc1ccc(Cc2cc([C@@H]3O[C@H](COC(C)=O)[C@@H](OCc4ccccc4)[C@H](OCc4ccccc4)[C@H]3OCc3ccccc3)c(OC[C@H]3C[C@H]3CI)cc2Cl)cc1]

To a solution of ((2R,3R,4R,5S,6S)-3,4,5-tris(benzyloxy)-6-(4-chloro-5-(4-ethoxybenzyl)-2-(((1S,2R)-2-(hydroxymethyl)cyclopropyl)methoxy)phenyl)tetrahydro-2H-pyran-2-yl)methyl acetate (47, 510 mg, 0.62 mmol) in benzene (18 mL) under an atmosphere of nitrogen were added imidazole (64 mg, 0.93 mmol) and triphenylphosphine (247 mg, 0.93 mmol). After 5 min, iodine (237 mg, 0.93 mmol) in benzene (4 mL) was added dropwise to the reaction mixture at room temperature. The reaction solution was stirred for 2 h, diluted with diethyl ether, quenched with saturated sodium hydrogen carbonate, and extracted with diethyl ether (2x). The organic layer was washed with brine, dried over magnesium sulfate, filtered and evaporated in vacuo. The resulting crude residue was purified on a Biotage® purification apparatus (silica gel, 5 to 25% tetrahydrofuran in hexanes gradient) to yield the title compound (48, 442 mg, 0.48 mmol, 76%) as a white solid.

$^1$H NMR (400 MHz, CDCl$_3$) δ 7.37-7.32 (m, 10H), 7.27-7.15 (m, 6H), 7.09-7.07 (m, 1H), 6.91-6.85 (m, 3H), 6.80-6.78 (m, 1H), 5.05-4.92 (m, 4H), 4.66-4.63 (m, 1H), 4.50-4.43 (m, 1H), 4.36-4.32 (m, 1H), 4.26-4.22 (m, 1H), 4.09-3.83 (m, 7H), 3.80-3.75 (m, 2H), 3.68-3.63 (m, 2H), 3.58-3.56 (m, 1H), 3.52 (t, J=6.8 Hz, 1H), 3.26-3.21 (m, 1H), 3.10 (m, 1H), 2.04 (s, 3H), 1.41 (t, J=6.8 Hz, 3H), 1.07-1.01 (m, 1H), 0.38-0.36 (m, 1H); MNa+ 953.

Step 5: ((2R,3R,4R,5S,6S)-3,4,5-Tris(benzyloxy)-6-(4-chloro-5-(4-ethoxybenzyl)-2-(((1S,2R)-2-(iodomethyl)cyclopropyl)methoxy)phenyl)tetrahydro-2H-pyran-2-yl)methanol (49)

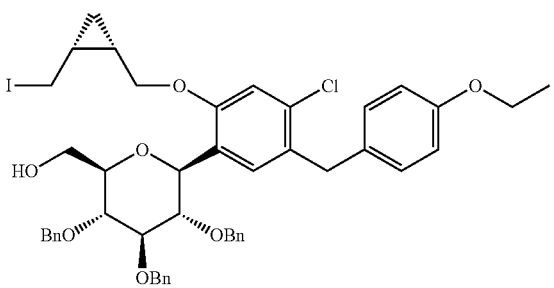 [SMILES: CCOc1ccc(Cc2cc([C@@H]3O[C@H](CO)[C@@H](OCc4ccccc4)[C@H](OCc4ccccc4)[C@H]3OCc3ccccc3)c(OC[C@H]3C[C@H]3CI)cc2Cl)cc1]

To a solution 48 (442 mg, 0.48 mmol) from Step 4 in methanol (5 mL) was added potassium carbonate (132 mg, 0.95 mmol) and the reaction mixture was stirred at room temperature for 0.5 h. The solution was quenched with H$_2$O (5 mL). The residue was diluted with ethyl acetate and water. The organic layer was separated and the aqueous layer was extracted with dichloromethane (2x). The combined organic layers were dried over magnesium sulfate, filtered and concentrated in vacuo. The crude residue was purified on Biotage® purification apparatus (silica gel, 5 to 25% tetrahydrofuran in hexanes) to yield the title compound (49, 420 mg, 0.47 mmol, 99%) as a white solid.

$^1$H NMR (400 MHz, CDCl$_3$) δ 7.41-7.32 (m, 10H), 7.28-7.15 (m, 6H), 7.09-7.06 (m, 1H), 6.92-6.90 (m, 1H), 6.87-6.85 (m, 1H), 6.80-6.77 (m, 2H), 5.01-4.93 (m, 3H), 4.74-4.71 (m, 1H), 4.50-4.44 (m, 1H), 4.07-3.95 (m, 6H), 3.94-3.84 (m, 3H), 3.80-3.66 (m, 3H), 3.58-3.56 (m, 1H), 3.52 (t, J=6.8 Hz, 1H), 3.26-3.21 (m, 1H), 3.15-3.14 (m, 1H), 1.41 (t, J=6.8 Hz, 3H), 1.09-1.03 (m, 1H), 0.39-0.35 (m, 1H); MNa+ 911.

Step 6: (4R,5S,6R,7R,8S)-Tris(benzyloxy)-11-chloro-10-(4-ethoxybenzyl)-(1aR,14aS)-1a,2,4,5,6,7,8,9,10-octahydro-1H-4,8-epoxybenzo[g]cyclopropa[c][1,6]dioxacyclotetradecine (50)

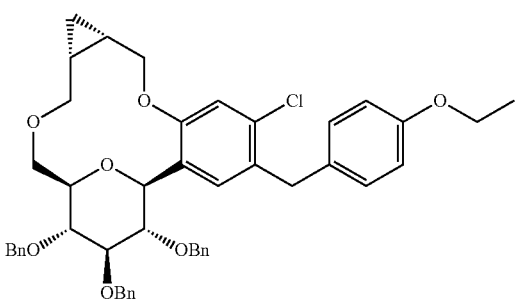 [SMILES: CCOc1ccc(Cc2cc3c(cc2Cl)OC[C@H]2C[C@H]2COC[C@H]2O[C@@H]3[C@H](OCc3ccccc3)[C@@H](OCc3ccccc3)[C@@H]2OCc2ccccc2)cc1]

To a solution of ((2R,3R,4R,5S,6S)-3,4,5-Tris(benzyloxy)-6-(4-chloro-5-(4-ethoxybenzyl)-2-(((1S,2R)-2-(iodomethyl)cyclopropyl)methoxy)phenyl)tetrahydro-2H-pyran-2-yl)methanol (49, 420 mg, 0.47 mmol) in N,N-dimethylformamide (10 mL) was added sodium hydride (60% dispersion in mineral oil, 38 mg, 0.94 mmol) at 0° C., and the reaction mixture was stirred at ambient temperature for 3 h. The reaction mixture was quenched by addition of water (5 mL) and extracted with ethyl acetate. The organic layer was washed with brine, dried over magnesium sulfate, filtered and evaporated in vacuo. The resulting crude residue was purified on a Biotage® purification apparatus (silica gel, 5 to 20% tetrahydrofuran in hexanes gradient) to yield the title compound (50, 225 mg, 0.30 mmol, 63%) as a white-off solid.

$^1$H NMR (400 MHz, CDCl$_3$) δ 7.36-7.33 (m, 10H), 7.27-7.15 (m, 5H), 7.09-7.07 (m, 1H), 7.03-7.02 (m, 1H), 6.94-6.89 (m, 3H), 6.79-6.77 (m, 1H), 5.01-4.91 (m, 3H), 4.80 (d, J=10.8 Hz, 1H), 4.55-4.51 (m, 1H), 4.48-4.42 (m, 1H), 4.19-4.11 (m, 2H), 4.10-3.98 (m, 5H), 3.96-3.82 (m, 5H), 3.79-3.73 (m, 1H), 3.70-3.61 (m, 1H), 3.58-3.56 (m, 1H), 3.52 (t, J=10.4 Hz, 1H), 1.41 (t, J=6.8 Hz, 3H), 1.38-1.28 (m, 1H), 0.98-0.92 (m, 1H); MNa+ 783.

Step 7: (4R,5S,6R,7R,8S)-11-Chloro-10-(4-ethoxybenzyl)-(1aR,14aS)-1a,2,4,5,6,7,8,9,10-octahydro-1H-4,8-epoxybenzo[g]cyclopropa[c][1,6]dioxacyclotetradecine-5,6,7-triol (51)

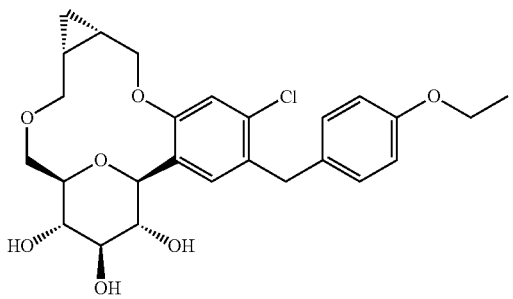

To a solution of 50 (225 mg, 0.30 mmol) in methanol (10 mL)/tetrahydrofuran (10 mL) was added 10% palladium on charcoal (67 mg). The reaction mixture was stirred under hydrogen gas overnight. The reaction solution was filtered through syringe filter and the filtrate was evaporated under reduced pressure. The crude compound was diluted with methanol and purified by reverse phase preparative HPLC (Waters®, SunFire™ Prep, 5 to 50% acetonitrile in water gradient) provided the title compound (51, 41 mg, 0.084 mmol, 28%) as a white-off solid. $^1$H NMR (400 MHz, DMSO-d$_6$) δ 7.27 (s, 1H), 7.15 (s, 1H), 7.10 (d, J=8.4 Hz, 2H), 6.83 (d, J=8.8 Hz, 2H), 5.07 (br, 1H), 5.03 (br, 1H), 4.95 (br, 1H), 4.41 (d, J=8.8 Hz, 1H), 4.12 (d, J=9.6 Hz, 1H), 3.97 (q, J=7.2 Hz, 2H), 3.94-3.86 (m, 3H), 3.80-3.75 (m, 1H), 3.63-3.53 (m, 3H), 3.38 (m, 2H), 3.28-3.26 (m, 2H), 1.39-1.34 (m, 1H), 1.31 (t, J=7.2 Hz, 3H), 1.15-1.06 (m, 1H), 0.75-0.70 (m, 1H), 0.47 (m, 1H); MNa+ 513, MH+ 491; IR (neat, cm$^{-1}$) 3372, 2866, 1608, 1509, 1493, 1241, 1074, 1046, 975, 839.

The following dichlorinated compound (7.2 mg, 0.016 mmol, 5%) was obtained from Example 15. MNa+ 479, MH+ 457.

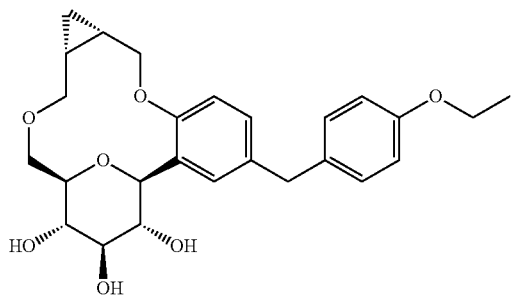 [SMILES: CCOc1ccc(Cc2ccc3c(c2)[C@@H]2O[C@H](COC[C@@H]4C[C@@H]4CO3)[C@@H](O)[C@H](O)[C@H]2O)cc1]

EXAMPLE 16

(4R,5S,6R,7R,8S)-11-Chloro-10-(4-ethoxybenzyl)-(1aS,14aR)-1a,2,4,5,6,7,8,9,10-octahydro-1H-4,8-epoxybenzo[g]cyclopropa[c][1,6]dioxacyclotetradecine-5,6,7-triol (52)

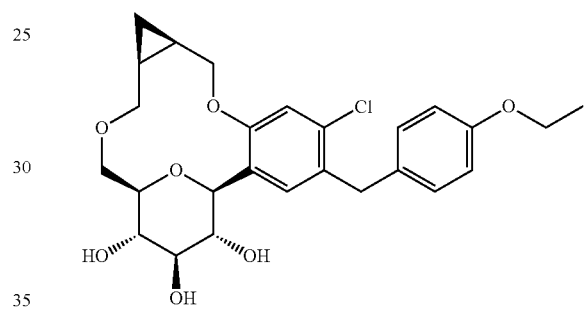

The titled compound (34 mg, 0.07 mmol, 36%) was obtained in the same manner as in Example 16 (Step 4 to 7). $^1$H NMR (400 MHz, DMSO-d$_6$) δ 7.21 (s, 1H), 7.16 (s, 1H), 7.10 (d, J=8.8 Hz, 2H), 5.00 (br, 1H), 4.99 (br, 1H), 4.87 (br, 1H), 4.41 (d, J=9.6 Hz, 2H), 4.03 (d, J=9.6 Hz, 1H), 3.97 (d, J=6.8 Hz, 2H), 3.95-3.90 (m, 3H), 3.71 (br, 1H), 3.61 (m, 1H), 3.53-3.51 (m, 3H), 3.33-3.25 (m, 3H), 1.39-1.35 (m, 1H), 1.31 (t, J=7.2 Hz, 3H), 1.17-1.08 (m, 1H), 0.76-0.71 (m, 1H), 0.36 (br, 1H); MNa+ 513, MH+ 491; IR (neat, cm$^{-1}$) 3374, 2912, 2867, 1608, 1510, 1440, 1241, 1075, 1006, 922, 839.

In Vitro Assay

Test 1: Cloning and Cell Line Construction for Human SGLT2

Human SGLT2 (hSGLT2) gene was amplified by PCR from cDNA-Human Adult Normal Tissue Kidney (Invitrogen). The hSGLT2 sequence was cloned into pcDNA3.1(+) for mammalian expression and were stably transfected into chinese hamster ovary (CHO) cells. SGLT2-expressing clones were selected based on resistance to G418 antibiotic (Geneticin) and activity in the $^{14}$C-α-methyl-D-glucopyranoside ($^{14}$C-AMG) uptake assay.

Test 2: Inhibitory Effects on Human SGLT2 Activities

For sodium-dependent glucose transport assay, cells expressing hSGLT2 were seeded into a 96-well culture plate at a density of 5×10$^4$ cells/well in RPMI medium 1640 containing 10% fetal bovine serum. The cells were used 1 day after plating. They were incubated in pretreatment buffer (10 mM HEPES, 5 mM Tris, 140 mM choline chloride, 2 mM KCl, 1 mM CaCl$_2$, and 1 mM MgCl$_2$, pH 7.4) at 37° C. for 10 min. They were then incubated in uptake buffer (10 mM HEPES, 5 mM Tris, 140 mM NaCl, 2 mM KCl, 1 mM $CaCl_2$, 1 mM $MgCl_2$, and 1 mM $^{14}C$-nonlabeled AMG pH 7.4) containing $^{14}C$-labeled AMG (8 μM) and the inventive compound or dimethyl sulfoxide (DMSO) vehicle at 37° C. for 2 h. Cells were washed twice with washing buffer (pretreatment buffer containing 10 mM AMG at room temperature) and then the radioactivity was measured using a liquid scintillation counter. $IC_{50}$ was determined by nonlinear regression analysis using GraphPad PRISM [Katsuno, K. et al. *J. Pharmacol. Exp. Ther.* 2007, 320, 323-330; Han, S. et al. *Diabetes*, 2008, 57, 1723-1729]. The inventive compounds and their IC50 are shown in following Table 1.

TABLE 1 hSGLT2 Inhibitory Activity

| Example | Structure | Name | $IC_{50}$ (nM) |
|---|---|---|---|
| 1 | 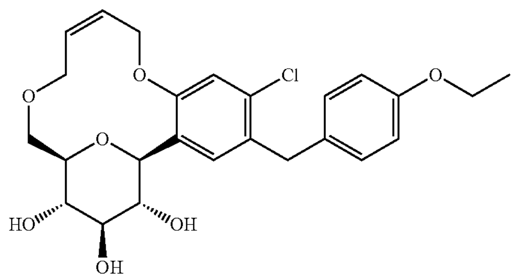 [SMILES: CCOc1ccc(Cc2cc3c(cc2Cl)OC/C=C\COC[C@H]2O[C@@H]3[C@H](O)[C@@H](O)[C@@H]2O)cc1] | (8R,9S,10R,11R,12S)-15-Chloro-14-(4-ethoxybenzyl)-2,5,7,8,9,10,11,12-octahydro-2H-8,12-epoxybenzo[g][1,6]dioxacyclotetradecine-9,10,11-triol | 0.974 |
| 2 | 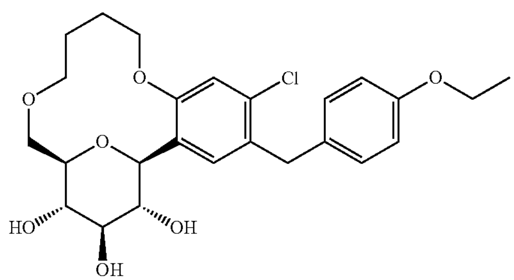 | (8R,9S,10R,11R,12S)-15-Chloro-14-(4-ethoxybenzyl)-2,3,4,5,7,8,9,10,11,12-decahydro-2H-8,12-epoxybenzo[g][1,6]dioxacyclotetradecine-9,10,11-triol | 2.27 |
| 3 | 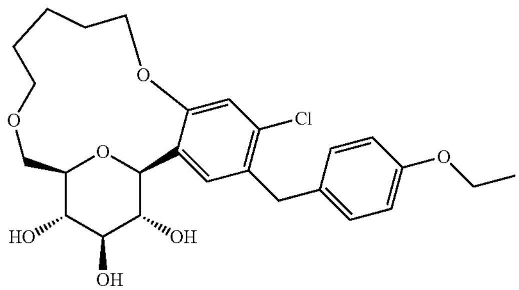 [SMILES: CCOc1ccc(Cc2cc3c(cc2Cl)OCCCCCOC[C@H]2O[C@@H]3[C@H](O)[C@@H](O)[C@@H]2O)cc1] | (9R,10S,11R,12R,13S)-16-Chloro-15-(4-ethoxybenzyl)-3,4,5,6,8,9,10,11,12,13-decahydro-2H-9,13-epoxybenzo[h][1,7]dioxacyclopentadecine-10,11,12-triol | 0.899 |
| 4 | 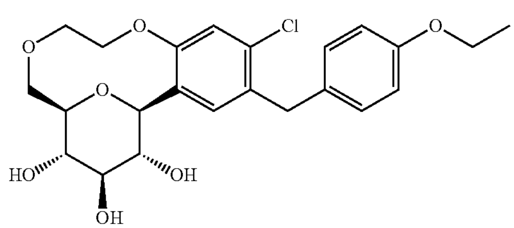 [SMILES: CCOc1ccc(Cc2cc3c(cc2Cl)OCCOC[C@H]2O[C@@H]3[C@H](O)[C@@H](O)[C@@H]2O)cc1] | (6R,7S,8R,9R,10S)-13-Chloro-12-(4-ethoxybenzyl)-2,3,5,6,7,8,9,10-octahydro-6,10-epoxybenzo[e][1,4]dioxacyclododecine-7,8,9-triol | 1.34 |
| 5 | 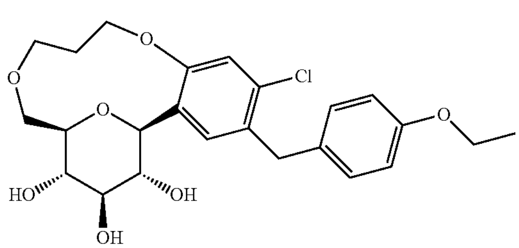 [SMILES: CCOc1ccc(Cc2cc3c(cc2Cl)OCCCOC[C@H]2O[C@@H]3[C@H](O)[C@@H](O)[C@@H]2O)cc1] | (7R,8S,9R,10R,11S)-14-Chloro-13-(4-ethoxybenzyl)-3,4,6,7,8,9,10,11-octahydro-2H-7,11-epoxybenzo[f][1,5]dioxacyclotridecine-8,9,10-triol | 2.95 |

TABLE 1-continued hSGLT2 Inhibitory Activity

| Example | Structure | Name | IC$_{50}$ (nM) |
|---|---|---|---|
| 6 | 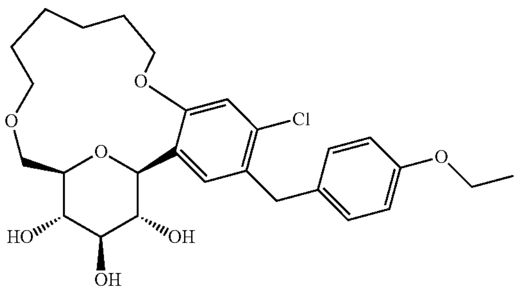 [SMILES: CCOc1ccc(Cc2cc3c(cc2Cl)OCCCCCCOC[C@H]2O[C@@H]3[C@H](O)[C@@H](O)[C@@H]2O)cc1] | (10R,11S,12R,13R,14S)-17-Chloro-16-(4-ethoxybenzyl)-2,3,4,5,6,7,9,10,11,12,13,14-dodecahydro-10,14-epoxybenzo[i][1,8]dioxacyclohexadecine-11,12,13-triol | 3.63 |
| 7 | 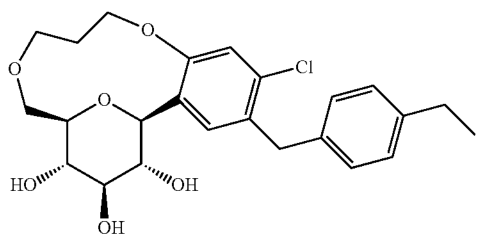 [SMILES: CCc1ccc(Cc2cc3c(cc2Cl)OCCCOC[C@H]2O[C@@H]3[C@H](O)[C@@H](O)[C@@H]2O)cc1] | (7R,8S,9R,10R,11S)-14-Chloro-13-(4-ethylbenzyl)-3,4,6,7,8,9,10,11-octahydro-2H-7,11-epoxybenzo[f][1,5]dioxacyclotridecine-8,9,10-triol | 1.59 |
| 8 | 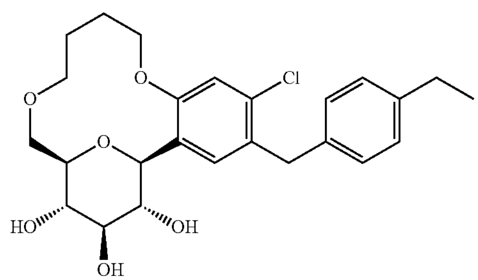 | (8R,9S,10R,11R,12S)-15-Chloro-14-(4-ethylbenzyl)-2,3,4,5,7,8,9,10,11,12-decahydro-8,12-epoxybenzo[g][1,6]dioxacyclotetradecine-9,10,11-triol | 1.4 |
| 9 | 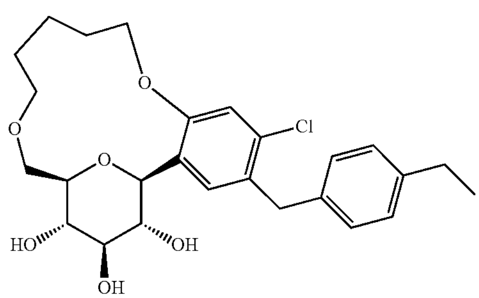 [SMILES: CCc1ccc(Cc2cc3c(cc2Cl)OCCCCCOC[C@H]2O[C@@H]3[C@H](O)[C@@H](O)[C@@H]2O)cc1] | (9R,10S,11R,12R,13S)-16-Chloro-15-(4-ethylbenzyl)-3,4,5,6,8,9,10,11,12,13-decahydro-2H-9,13-epoxybenzo[h][1,7]dioxacyclopentadecine-10,11,12-triol | 1.38 |
| 10 | 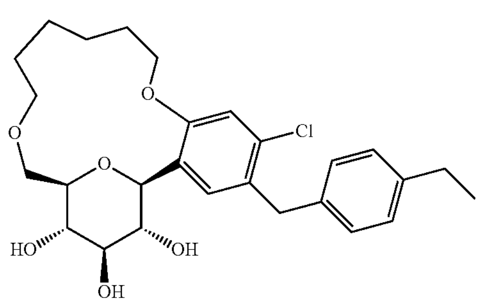 [SMILES: CCc1ccc(Cc2cc3c(cc2Cl)OCCCCCCOC[C@H]2O[C@@H]3[C@H](O)[C@@H](O)[C@@H]2O)cc1] | (10R,11S,12R,13R,14S)-17-Chloro-16-(4-ethylbenzyl)-2,3,4,5,6,7,9,10,11,12,13,14-dodecahydro-10,14-epoxybenzo[i][1,8]dioxacyclohexadecine-11,12,13-triol | 1.4 |

TABLE 1-continued hSGLT2 Inhibitory Activity

| Example | Structure | Name | IC$_{50}$ (nM) |
|---|---|---|---|
| 11 | 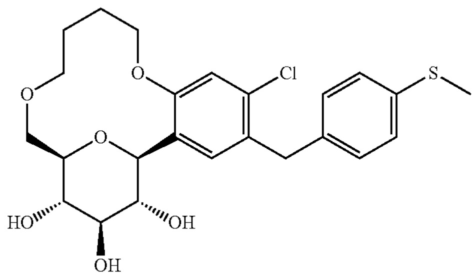 | (8R,9S,10R,11R,12S)-15-Chloro-14-(4-(methylthio)benzyl)-2,3,4,5,7,8,9,10,11,12-decahydro-8,12-epoxybenzo[g][1,6]dioxacyclotetradecine-9,10,11-triol | 1.35 |
| 12 | 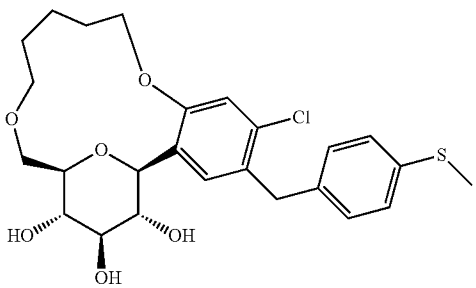 [SMILES: CSc1ccc(Cc2cc3c(cc2Cl)OCCCCCOC[C@H]2O[C@@H]3[C@H](O)[C@@H](O)[C@@H]2O)cc1] | (9R,10S,11R,12R,13S)-16-Chloro-15-(4-(methylthio)benzyl)-3,4,5,6,8,9,10,11,12,13-decahydro-2H-9,13-epoxybenzo[h][1,7]dioxacyclopentadecine-10,11,12-triol | 0.778 |
| 13 | 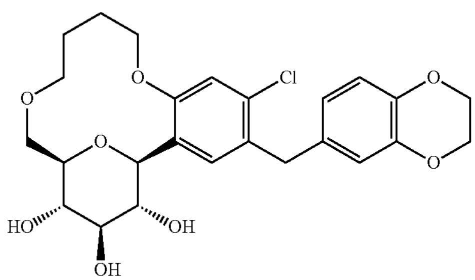 [SMILES: O[C@@H]1[C@@H](O)[C@H]2O[C@H](COCCCCOc3cc(Cl)c(Cc4ccc5c(c4)OCCO5)cc32)[C@H]1O] | (8R,9S,10R,11R,12S)-15-Chloro-14-((2,3-dihydrobenzo[b][1,4]dioxin-6-yl)methyl)-2,3,4,5,7,8,9,10,11,12-decahydro-8,12-epoxybenzo[g][1,6]dioxacyclotetradecine-9,10,11-triol | 3.65 |
| 14 | 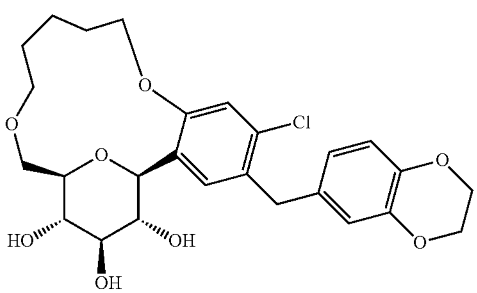 [SMILES: O[C@@H]1[C@@H](O)[C@H]2O[C@H](COCCCCCOc3cc(Cl)c(Cc4ccc5c(c4)OCCO5)cc32)[C@H]1O] | (9R,10S,11R,12R,13S)-16-Chloro-15-((2,3-dihydrobenzo[b][1,4]dioxin-6-yl)methyl)-3,4,5,6,8,9,10,11,12,13-decahydro-2H-9,13-epoxybenzo[h][1,7]dioxacyclopentadecine-10,11,12-triol | 1.38 |
| 15 | 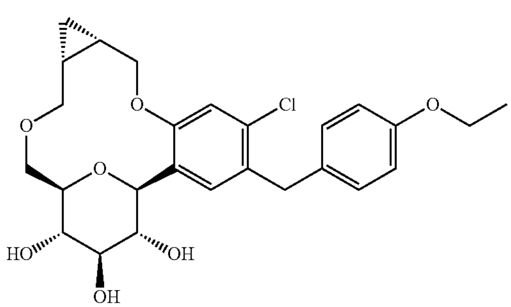 [SMILES: CCOc1ccc(Cc2cc3c(cc2Cl)OC[C@H]2C[C@H]2COC[C@H]2O[C@@H]3[C@H](O)[C@@H](O)[C@@H]2O)cc1] | (4R,5S,6R,7R,8S)-11-Chloro-10-(4-ethoxybenzyl)-(1aR,14aS)-1a,2,4,5,6,7,8,9,10-octahydro-1H-4,8-epoxybenzo[g]cyclopropa[c][1,6]dioxacyclotetradecine-5,6,7-triol | 2.3 |

TABLE 1-continued hSGLT2 Inhibitory Activity

| Example | Structure | Name | IC$_{50}$ (nM) |
|---|---|---|---|
| 16 | 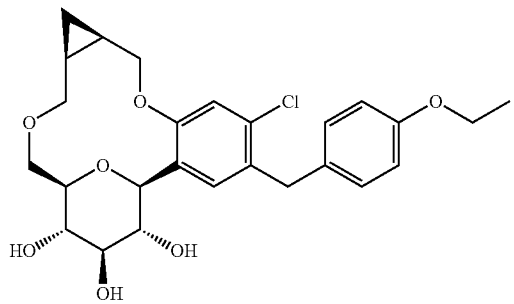 [SMILES: CCOc1ccc(Cc2cc3c(cc2Cl)OC[C@@H]2C[C@@H]2COC[C@H]2O[C@@H]3[C@H](O)[C@@H](O)[C@@H]2O)cc1] | (4R,5S,6R,7R,8S)-11-Chloro-10-(4-ethoxybenzyl)-(1aS,14aR)-1a,2,4,5,6,7,8,9,10-octahydro-1H-4,8-epoxybenzo[g]cyclopropa[c][1,6]dioxacyclotetradecine-5,6,7-triol | 14 |

* Reference compound dapagliflozin IC$_{50}$ = 1.35 ± 0.15 nM (in-house assay).

What is claimed is:

1. A compound of formula I, or a pharmaceutically acceptable salt or a prodrug thereof:

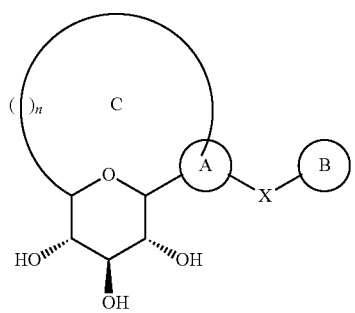

I wherein,
X is methylene or cyclopropane;
ring A is benzene, naphthalene, or indole;
ring B is

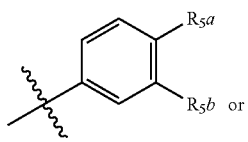

B-1 or

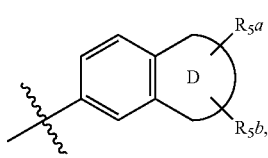

B-2 said ring D being $C_{3-10}$ cycloalkyl, $C_{5-10}$ cycloalkenyl, $C_{6-14}$ aryl, 5 to 13-membered heteroaryl, or 5 to 10-membered heterocycloalkyl;
ring C is a macrocycle formed by connecting ansa bridge between the tetrahydropyran ring and ring A; and
n is an integer of 5 to 10,
wherein,
said ring A and ring B are each independently optionally substituted with at least one selected from the group consisting of hydrogen, halogen, hydroxy, mercapto, cyano, nitro, amino, carboxy, $C_{1-7}$ alkyl, $C_{2-7}$ alkenyl, $C_{2-7}$ alkynyl, hydroxy-$C_{1-7}$ alkyl, $C_{1-7}$ alkoxy, $C_{1-7}$ alkoxy-$C_{1-7}$ alkyl, $C_{2-7}$ alkenyl-$C_{1-7}$ alkyloxy, $C_{2-7}$ alkynyl-$C_{1-7}$ alkyloxy, $C_{3-10}$ cycloalkyl, $C_{5-10}$ cycloalkenyl, $C_{3-10}$ cycloalkyloxy, phenyl-$C_{1-7}$ alkoxy, mono- or di-$C_{1-7}$ alkylamino, $C_{1-7}$ alkanoyl, $C_{1-7}$ alkanoylamino, $C_{1-7}$ alkoxycarbonyl, carbamoyl, mono- or di-$C_{1-7}$ alkylcarbamoyl, $C_{1-7}$ alkylsulfonylamino, phenylsulfonylamino, $C_{1-7}$ alkylsulfanyl, $C_{1-7}$ alkylsulfinyl, $C_{1-7}$ alkylsulfonyl, $C_{6-14}$ arylsulfanyl, $C_{6-14}$ arylsulfonyl, $C_{6-14}$ aryl, 5 to 13-membered heteroaryl, and 5 to 10-membered heterocycloalkyl;
said $R_{5a}$, $R_{5b}$, $R_{6a}$, and $R_{6b}$ are each independently selected from the group consisting of hydrogen, halogen, hydroxy, mercapto, cyano, nitro, amino, carboxy, $C_{1-7}$ alkyl, $C_{2-7}$ alkenyl, $C_{2-7}$ alkynyl, hydroxy-$C_{1-7}$ alkyl, $C_{1-7}$ alkoxy, $C_{1-7}$ alkoxy-$C_{1-7}$ alkyl, $C_{2-7}$ alkenyl-$C_{1-7}$ alkyloxy, $C_{2-7}$ alkynyl-$C_{1-7}$ alkyloxy, $C_{3-10}$ cycloalkyl, $C_{5-10}$ cycloalkenyl, $C_{3-10}$ cycloalkyloxy, phenyl-$C_{1-7}$ alkoxy, mono- or di-$C_{1-7}$ alkylamino, $C_{1-7}$ alkanoyl, $C_{1-7}$ alkanoylamino, $C_{1-7}$ alkoxycarbonyl, carbamoyl, mono- or di-$C_{1-7}$ alkylcarbamoyl, $C_{1-7}$ alkylsulfonylamino, phenylsulfonylamino, $C_{1-7}$ alkylsulfanyl, $C_{1-7}$ alkylsulfinyl, $C_{1-7}$ alkylsulfonyl, $C_{6-14}$ arylsulfanyl, $C_{6-14}$ arylsulfonyl, $C_{6-14}$ aryl, 5 to 13-membered heteroaryl, and 5 to 10-membered heterocycloalkyl;
said alkyl, alkenyl, alkynyl, or alkoxy is optionally substituted with at least one selected from the group consisting of halogen, hydroxy, cyano, nitro, amino, mercapto, $C_{1-7}$ alkyl, and $C_{2-7}$ alkynyl; and
said cycloalkyl, cycloalkenyl, aryl, heteroaryl, or heterocycloalkyl is optionally substituted with at least one selected from the group consisting of halogen, hydroxy, cyano, nitro, amino, mercapto, $C_{1-4}$ alkyl, and $C_{1-4}$ alkoxy.

2. The compound of claim 1, wherein said ring A is selected from the group consisting of:

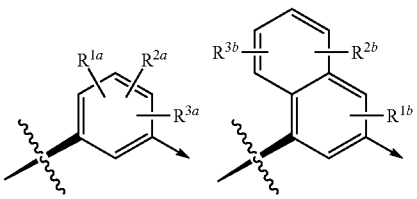

-continued

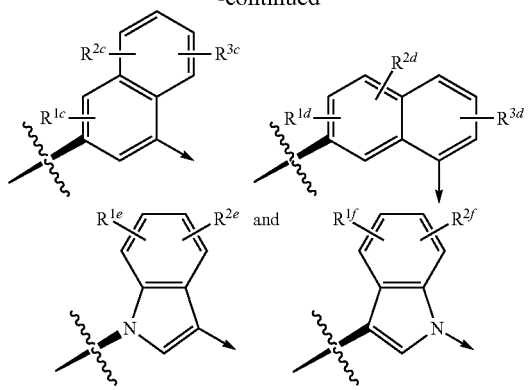

wherein, $R^{1a}$, $R^{2a}$, $R^{3a}$, $R^{1b}$, $R^{2b}$, $R^{3b}$, $R^{1c}$, $R^{2c}$, $R^{3c}$, $R^{1d}$, $R^{2d}$, $R^{3d}$, $R^{1e}$, $R^{2e}$, $R^{1f}$, and $R^{2f}$ are each independently selected from the group consisting of hydrogen, halogen, hydroxy, mercapto, cyano, nitro, amino, carboxy, $C_{1-7}$ alkyl, $C_{2-7}$ alkenyl, $C_{2-7}$ alkynyl, hydroxy-$C_{1-7}$ alkyl, $C_{1-7}$ alkoxy, $C_{1-7}$ alkoxy-$C_{1-7}$ alkyl, $C_{2-7}$ alkenyl-$C_{1-7}$ alkyloxy, $C_{2-7}$ alkynyl-$C_{1-7}$ alkyloxy, $C_{3-10}$ cycloalkyl, $C_{5-10}$ cycloalkenyl, $C_{3-10}$ cycloalkyloxy, phenyl-$C_{1-7}$ alkoxy, mono- or di-$C_{1-7}$ alkylamino, $C_{1-7}$ alkanoyl, $C_{1-7}$ alkanoylamino, $C_{1-7}$ alkoxycarbonyl, carbamoyl, mono- or di-$C_{1-7}$ alkylcarbamoyl, $C_{1-7}$ alkylsulfonylamino, phenylsulfonylamino, $C_{1-7}$ alkylsulfanyl, $C_{1-7}$ alkylsulfinyl, $C_{1-7}$ alkylsulfonyl, $C_{6-14}$ arylsulfanyl, $C_{6-14}$ arylsulfonyl, $C_{6-14}$ aryl, 5 to 13-membered heteroaryl, and 5 to 10-membered heterocycloalkyl.

3. The compound of claim 1, wherein said ring B-1 is selected from the group consisting of:

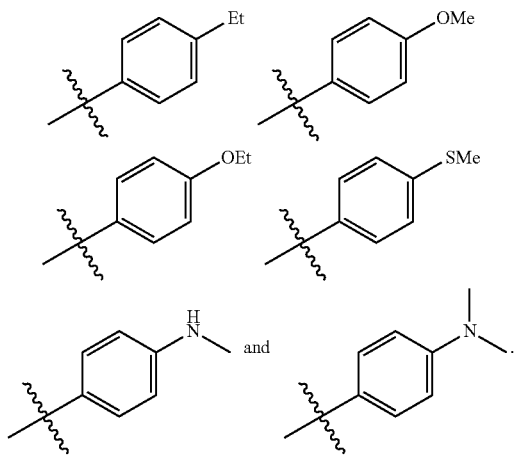

4. The compound of claim 1, wherein said ring B-2 is selected from the group consisting of:

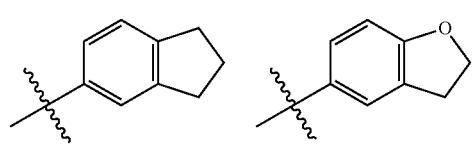

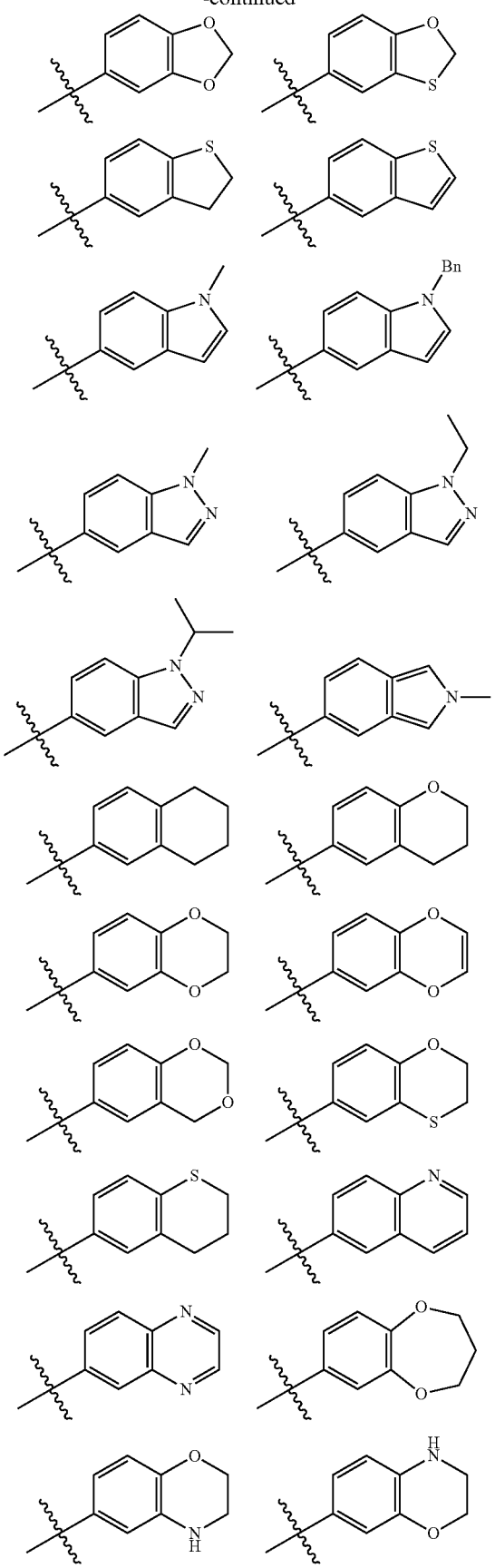

-continued

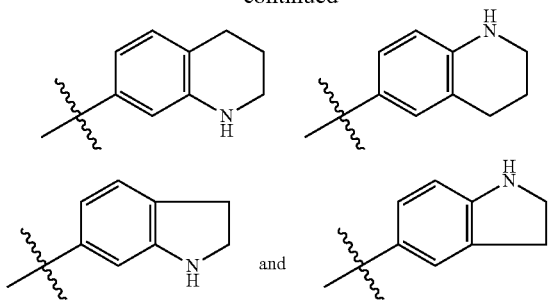

5. The compound of claim 1, which has the following structure:

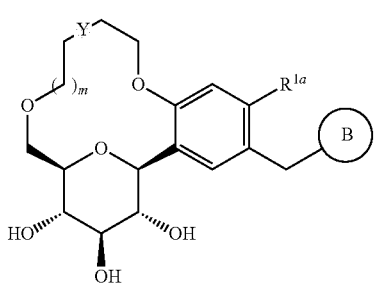

I-1 wherein,
Y is a single bond or double bond, or forms a cyclopropane ring together with the two adjacent carbon atoms;
m is an integer of 1 to 4;
$R^{1a}$ is halogen; and
ring B is

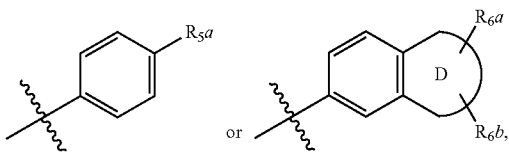

said $R_{5a}$, $R_{6a}$, and $R_{6b}$ being each independently selected from the group consisting of hydrogen, halogen, hydroxy, mercapto, cyano, nitro, amino, carboxy, $C_{1-7}$ alkyl, $C_{2-7}$ alkenyl, $C_{2-7}$ alkynyl, hydroxy-$C_{1-7}$ alkyl, $C_{1-7}$ alkoxy, $C_{1-7}$ alkoxy-$C_{1-7}$ alkyl, $C_{2-7}$ alkenyl-$C_{1-7}$ alkyloxy, $C_{2-7}$ alkynyl-$C_{1-7}$ alkyloxy, $C_{3-10}$ cycloalkyl, $C_{5-10}$ cycloalkenyl, $C_{3-10}$ cycloalkyloxy, phenyl-$C_{1-7}$ alkoxy, mono- or di-$C_{1-7}$ alkylamino, $C_{1-7}$ alkanoyl, $C_{1-7}$ alkanoylamino, $C_{1-7}$ alkoxycarbonyl, carbamoyl, mono- or di-$C_{1-7}$ alkylcarbamoyl, $C_{1-7}$ alkylsulfonylamino, phenylsulfonylamino, $C_{1-7}$ alkylsulfanyl, $C_{1-7}$ alkylsulfinyl, $C_{1-7}$ alkylsulfonyl, $C_{6-14}$ arylsulfanyl, $C_{6-14}$ arylsulfonyl, $C_{6-14}$ aryl, 5 to 13-membered heteroaryl, or 5 to 10-membered heterocycloalkyl, and
said ring D being dioxanyl.

6. The compound of claim 1, which is selected from the group consisting of:
(1) (8R,9S,10R,11R,12S)-15-Chloro-14-(4-ethoxybenzyl)-2,5,7,8,9,10,11,12-octahydro-2H-8,12-epoxybenzo[g][1,6]dioxacyclotetradecine-9,10,11-triol;
(2) (8R,9S,10R,11R,12S)-15-Chloro-14-(4-ethoxybenzyl)-2,3,4,5,7,8,9,10,11,12-decahydro-2H-8,12-epoxybenzo[g][1,6]dioxacyclotetradecine-9,10,11-triol;
(3) (9R,10S,11R,12R,13S)-16-Chloro-15-(4-ethoxybenzyl)-3,4,5,6,8,9,10,11,12,13-decahydro-2H-9,13-epoxybenzo[h][1,7]dioxacyclopentadecine-10,11,12-triol;
(4) (6R,7S,8R,9R,10S)-13-Chloro-12-(4-ethoxybenzyl)-2,3,5,6,7,8,9,10-octahydro-6,10-epoxybenzo[e][1,4]dioxacyclododecine-7,8,9-triol;
(5) (7R,8S,9R,10R,11S)-14-Chloro-13-(4-ethoxybenzyl)-3,4,6,7,8,9,10,11-octahydro-2H-7,11-epoxybenzo[f][1,5]dioxacyclotridecine-8,9,10-triol;
(6) (10R,11S,12R,13R,14S)-17-Chloro-16-(4-ethoxybenzyl)-2,3,4,5,6,7,9,10,11,12,13,14-dodecahydro-10,14-epoxybenzo[i][1,8]dioxacyclohexadecine-11,12,13-triol;
(7) (7R,8S,9R,10R,11S)-14-Chloro-13-(4-ethylbenzyl)-3,4,6,7,8,9,10,11-octahydro-2H-7,11-epoxybenzo[f][1,5]dioxacyclotridecine-8,9,10-triol;
(8) (8R,9S,10R,11R,12S)-15-Chloro-14-(4-ethylbenzyl)-2,3,4,5,7,8,9,10,11,12-decahydro-8,12-epoxybenzo[g][1,6]dioxacyclotetradecine-9,10,11-triol;
(9) (9R,10S,11R,12R,13S)-16-Chloro-15-(4-ethylbenzyl)-3,4,5,6,8,9,10,11,12,13-decahydro-2H-9,13-epoxybenzo[h][1,7]dioxacyclopentadecine-10,11,12-triol;
(10) (10R,11S,12R,13R,14S)-17-Chloro-16-(4-ethylbenzyl)-2,3,4,5,6,7,9,10,11,12,13,14-dodecahydro-10,14-epoxybenzo[i][1,8]dioxacyclohexadecine-11,12,13-triol;
(11) (8R,9S,10R,11R,12S)-15-Chloro-14-(4-(methylthio)benzyl)-2,3,4,5,7,8,9,10,11,12-decahydro-8,12-epoxybenzo[g][1,6]dioxacyclotetradecine-9,10,11-triol;
(12) (9R,10S,11R,12R,13S)-16-Chloro-15-(4-(methylthio)benzyl)-3,4,5,6,8,9,10,11,12,13-decahydro-2H-9,13-epoxybenzo[h][1,7]dioxacyclopentadecine-10,11,12-triol;
(13) (8R,9S,10R,11R,12S)-15-Chloro-14-((2,3-dihydrobenzo[b][1,4]dioxin-6-yl)-methyl)-2,3,4,5,7,8,9,10,11,12-decahydro-8,12-epoxybenzo[g][1,6]dioxacyclotetradecine-9,10,11-triol;
(14) (9R,10S,11R,12R,13S)-16-Chloro-15-((2,3-dihydrobenzo[b][1,4]dioxin-6-yl)-methyl)-3,4,5,6,8,9,10,11,12,13-decahydro-2H-9,13-epoxybenzo[h][1,7]dioxacyclopentadecine-10,11,12-triol;
(15) (4R,5S,6R,7R,8S)-11-Chloro-10-(4-ethoxybenzyl)-(1aR,14aS)-1a,2,4,5,6,7,8,9,10-octahydro-1H-4,8-epoxybenzo[g]cyclopropa[c][1,6]dioxacyclotetradecine-5,6,7-triol; and
(16) (4R,5S,6R,7R,8S)-11-Chloro-10-(4-ethoxybenzyl)-(1aS,14aR)-1a,2,4,5,6,7,8,9,10-octahydro-1H-4,8-epoxybenzo[g]cyclopropa[c][1,6]dioxacyclotetradecine-5,6,7-triol.

7. A method for preparing a compound of formula II-3, comprising:
a) subjecting a compound of formula II-1 to intramolecular alkylation to obtain a compound formula II-2; and
b) deprotecting the compound of formula II-2 to obtain a compound of formula II-3:

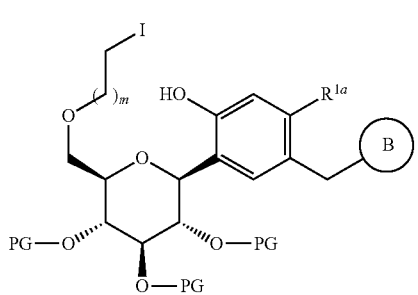

II-1

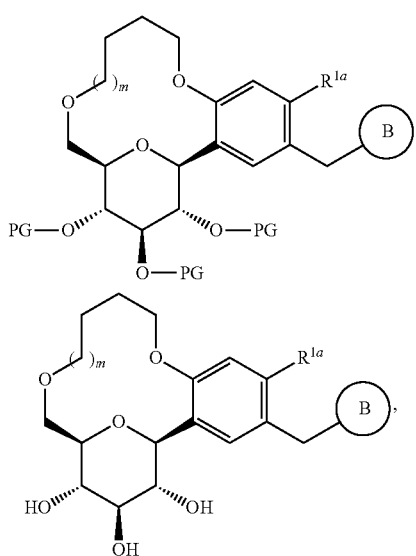

II-2

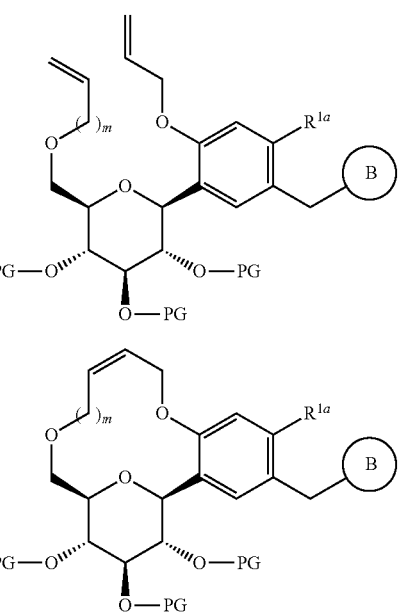

II-4

II-3

II-5

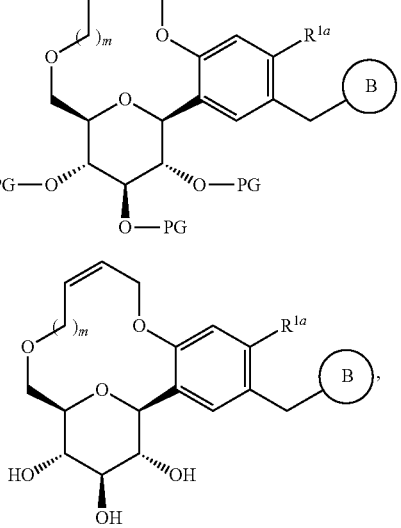

wherein
—PG is a protecting group;
m is an integer of 1 to 4;
$R^{1a}$ is halogen; and
ring B is

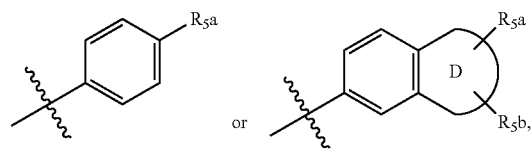

II-6 said $R_5$, $R_{6a}$, and $R_{6b}$ being each independently selected from the group consisting of hydrogen, halogen, hydroxy, mercapto, cyano, nitro, amino, carboxy, $C_{1-7}$ alkyl, $C_{2-7}$ alkenyl, $C_{2-7}$ alkenyl, hydroxy-$C_{1-7}$ alkyl, $C_{1-7}$ alkoxy, $C_{1-7}$ alkoxy-$C_{1-7}$ alkyl, $C_{2-7}$ alkenyl-$C_{1-7}$ alkyloxy, $C_{2-7}$ alkenyl-$C_{1-7}$ alkyloxy, $C_{3-10}$ cycloalkyl, $C_{5-10}$ cycloalkenyl, $C_{3-10}$ cycloalkyloxy, phenyl-$C_{1-7}$ alkoxy, mono- or di-$C_{1-7}$ alkylamino, $C_{1-7}$ alkanoyl, $C_{1-7}$ alkanoylamino, $C_{1-7}$ alkoxycarbonyl, carbamoyl, mono- or di-$C_{1-7}$ alkylcarbamoyl, $C_{1-7}$ alkylsulfonylamino, phenylsulfonylamino, $C_{1-7}$ alkylsulfanyl, $C_{1-7}$ alkylsulfinyl, $C_{1-7}$ alkylsulfonyl, $C_{6-14}$ arylsulfanyl, $C_{6-14}$ arylsulfonyl, $C_{6-14}$ aryl, 5 to 13-membered heteroaryl, or 5 to 10-membered heterocycloalkyl, and said ring D being dioxanyl.

8. A method for preparing a compound of formula II-6, comprising:
a) subjecting a compound of formula II-4 to ring-closing methathesis using Grubb's catalyst to obtain a compound formula II-5; and
b) deprotecting the compound of formula II-5 to obtain a compound of formula II-6:

wherein
—PG is a protecting group;
m is an integer of 1 to 4;
$R^{1a}$ is halogen; and
ring B is

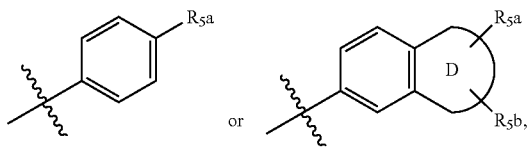

said $R_5$, $R_{6a}$, and $R_{6b}$ being each independently selected from the group consisting of hydrogen, halogen, hydroxy, mercapto, cyano, nitro, amino, carboxy, $C_{1-7}$ alkyl, $C_{2-7}$ alkenyl, $C_{2-7}$ alkenyl, hydroxy-$C_{1-7}$ alkyl, $C_{1-7}$ alkoxy, $C_{1-7}$ alkoxy-$C_{1-7}$ alkyl, $C_{2-7}$ alkenyl-$C_{1-7}$ alkyloxy, $C_{2-7}$ alkenyl-$C_{1-7}$ alkyloxy, $C_{3-10}$ cycloalkyl, $C_{5-10}$ cycloalkenyl, $C_{3-10}$ cycloalkyloxy, phenyl-$C_{1-7}$ alkoxy, mono- or di-$C_{1-7}$ alkylamino, $C_{1-7}$ alkanoyl, $C_{1-7}$ alkanoylamino, $C_{1-7}$ alkoxycarbonyl, carbamoyl, mono- or di-$C_{1-7}$ alkylcarbamoyl, $C_{1-7}$ alkylsulfonylamino, phenylsulfonylamino, $C_{1-7}$ alkylsulfanyl, $C_{1-7}$ alkylsulfinyl, $C_{1-7}$ alkylsulfonyl, $C_{6-14}$ arylsulfanyl, $C_{6-14}$ arylsulfonyl, $C_{6-14}$ aryl, 5 to 13-membered heteroaryl, or 5 to 10-membered heterocycloalkyl, and
said ring D being dioxanyl.

9. A pharmaceutical composition for preventing or treating a metabolic disorder, comprising as an active ingredient the compound of formula I of claim 1 or a pharmaceutically acceptable salt or a prodrug thereof, and a pharmaceutically acceptable carrier.

10. A method for preventing or treating a metabolic disorder in a mammal, which comprises administering the compound of formula I of claim 1 or a pharmaceutically acceptable salt or a prodrug thereof to the mammal.

11. A method for inhibiting sodium-dependent glucose cotransporter 2 (SGLT2) in a mammal, which comprises administering the compound of formula I of claim 1 or a pharmaceutically acceptable salt or a prodrug thereof to the mammal.

* * * * *